(12) United States Patent
Blankenstein et al.

(10) Patent No.: US 12,338,272 B2
(45) Date of Patent: Jun. 24, 2025

(54) HIGH AVIDITY ANTIGEN RECOGNIZING CONSTRUCTS

(71) Applicant: MAX-DELBRÜCK-CENTRUM FÜR MOLEKULARE MEDIZIN (MDC) BERLIN-BUCH, Berlin (DE)

(72) Inventors: Thomas Blankenstein, Berlin (DE); Matthias Obenaus, Berlin (DE); Catarina Leitão, Lisbon (PT)

(73) Assignee: Max-Delbrück-Centrum Für Molekulare Medizin (MDC) Berlin-Buch, Berlin (DE)

( * ) Notice: Subject to any disclaimer, the term of this patent is extended or adjusted under 35 U.S.C. 154(b) by 396 days.

(21) Appl. No.: 17/933,088

(22) Filed: Sep. 17, 2022

(65) Prior Publication Data

US 2023/0025572 A1     Jan. 26, 2023

Related U.S. Application Data

(62) Division of application No. 16/507,803, filed on Jul. 10, 2019, now Pat. No. 11,447,536, which is a division of application No. 14/763,421, filed as application No. PCT/EP2014/051726 on Jan. 29, 2014, now Pat. No. 10,377,808.

(30) Foreign Application Priority Data

Jan. 29, 2013   (EP) .................................. 13153081

(51) Int. Cl.
| | |
|---|---|
| C07K 14/725 | (2006.01) |
| C07K 14/705 | (2006.01) |
| C07K 16/28 | (2006.01) |
| C07K 16/30 | (2006.01) |
| G01N 33/574 | (2006.01) |
| C12N 15/62 | (2006.01) |

(52) U.S. Cl.
CPC .... C07K 14/7051 (2013.01); C07K 14/70503 (2013.01); C07K 16/2803 (2013.01); C07K 16/30 (2013.01); G01N 33/57484 (2013.01); C07K 2317/565 (2013.01); C07K 2317/76 (2013.01); C12N 15/62 (2013.01); G01N 2333/705 (2013.01)

(58) Field of Classification Search
CPC .......... C07K 14/70503; C07K 16/2803; C07K 16/30; C07K 14/7051; C07K 2317/565; C07K 2317/16; C12N 15/62; G01N 33/57484; G01N 2333/705; A61P 35/00
See application file for complete search history.

(56) References Cited

U.S. PATENT DOCUMENTS 8,519,100 B2    8/2013  Jakobsen et al.
2009/0304679 A1  12/2009  Weidanz

FOREIGN PATENT DOCUMENTS

WO      9523164 A1    8/1995

OTHER PUBLICATIONS

Farina et al., Conserved TCR usage by HLA-Cw*1601-restricted T cell clones recognizing melanoma antigens, International Immunology, 1996, 8(9):1463-1466.*
Chames, Patrick et al., "Direct selection of a human antibody fragment directed against the tumor T-cell epitope HLA-A1-MAGE-A1 from a nonimmunized phage-Fab library," PNAS, Jul. 5, 2000, 97(14):7969-7974.
Database Geneseq, "Human T-cell receptor beta-chain protein," XP002712966, retrieved from EBI accession No. GSP:AFS46936, Jun. 14, 2007.
Database Geneseq, "HIV Gag TCR alpha chain (optimized for expression in human T cells)," XP002699806, retrieved from EBI accession No. GSP: AEK68686, Nov. 30, 2006.
Deng, Lu et al., "Structural insights into the editing of germ-line-encoded interactions between T-cell receptor and MHC class IL by V alpha CDR3," PNAS 109(37):14960-14965, Sep. 11, 2012.
Engels, Boris et al., "Redirecting Human T Lymphocytes Toward Renal Cell Carcinoma Specificity by Retroviral Transfer of T Cell Receptor Genes," Human Gene Therapy, Jul. 2005, 16:799-810.
Garcia, K. Christopher, Adams, Erin J., "How the T Cell Receptor Sees Antigen—A Structural View," Cell 122:333-336, Aug. 12, 2005.
Goyarts, Earl C. et al., "Point mutations in the B chain CDR3 can alter the T cell receptor recognition pattern of an MHC class I/peptide complex over a broad interface area," Molecular Immunology 35:593-607, 1998.
Janeway, Jr., Charles A. et al., 5th Ed., Garland Science, 2001, pp. 106-108, 117-118 and 260-263.
Kessels, Helmut W. H. et al., "Changing T cell specificity by retroviral T cell receptor display", PNAS 97 (26):14578-14583, Dec. 19, 2000.
Li, Liang-Ping et al., "Transgenic mice with a diverse human T cell antigen receptor repertoire," Nature Medicine 16 (9):1029-1034, Sep. 2010.
Manning, Thomas C. et al., "Alanine Scanning Mutagenesis of an αβ T cell Receptor: Mapping the Energy of Antigen Recognition," Immunity 8:413-425, Apr. 1998.

(Continued)

*Primary Examiner* — Hong Sang
(74) *Attorney, Agent, or Firm* — SALIWANCHIK, LLOYD & EISENSCHENK

(57) ABSTRACT

The present invention pertains to novel high avidity antigen recognizing constructs, such as antibodies or T cell receptors, which specifically bind to the melanoma associated antigen (MAGE) A1. The constructs of the invention are particularly useful for the diagnosis, prevention or therapy of tumorous diseases which are characterized by the specific expression of the MAGE-A1 antigen. Furthermore provided are nucleic acids, vectors and host cells—such as CD4 or CD8 positive T cells—which encode, comprise or present the antigen recognizing constructs of the invention. The invention thus provides new approaches for immune therapy, specifically adoptive T cell therapy, for treating cancer.

2 Claims, 17 Drawing Sheets

Specification includes a Sequence Listing.

(56) References Cited

OTHER PUBLICATIONS

Matkovic, Bozica et al., "Expression of MAGE-A and NY-ESO-1 cancer/testis antigens in medullary breast cancer: retrospective immunohistochemical study," Croatian Medical Journal, 2011, 52(2):171-177.

Naklefski, Eric et al., "Functional Analysis of the Antigen Binding Site on the T Cell Receptor α Chain," J. Exp. Med. 175:1563-1563, Jun. 1992.

Orentas, Rimas J. et al., "Retroviral Transduction of a T Cell Receptor Specific for an Epstein-Barr Virus-Encoded Peptide," Clinical Immunology, Feb. 2001, 98(2):220-228.

Ottaviani, Sabrina et al., "A MAGE-1 antigenic peptide recognized by human cytolytic T lymphocytes on HLA-A2 tumor cells," Cancer Immunology: Immunotherapy: CII, 2005, 54(12):1214-1220.

Sharma, P., Kranz, D.M. "Subtle changes at the variable domain interface of the T-cell receptor can strongly increase affinity" Journal of Biological Chemistry 293(5):1820-1834, Dec. 2017.

Sommermeyer, Daniel et al., "Designer T cells by T cell receptor replacement," Eur. J. Immunol., 2006, 36:3052-3059.

Venturi, V. et al. "A Mechanism for TCR Sharing between T Cell Subsets and Individuals Revealed by Pyrosequencing," Journal of Immunology 186:4285-4294, prepublished on line on Mar. 7, 2011.

\* cited by examiner

HIGH AVIDITY ANTIGEN RECOGNIZING CONSTRUCTS

CROSS-REFERENCE TO RELATED APPLICATIONS

This application is a Divisional Application of U.S. Ser. No. 16/507,803, filed Jul. 10, 2019; which is a Divisional Application of U.S. Ser. No. 14/763,421, filed Jul. 24, 2015, now U.S. Pat. No. 10,377,808; which is a National Stage Application of International Application Number PCT/EP2014/051726, filed Jan. 29, 2014; which claims priority to European Application No. 13153081.8, filed Jan. 29, 2013; all of which are incorporated herein by reference in their entirety.

The Sequence Listing for this application is labeled BB.385D2-SeqList-asfiled.xml, which was created on Sep. 16, 2022, and is 131,510 bytes. The entire content is incorporated herein by reference in its entirety.

FIELD OF THE INVENTION

The present invention pertains to novel high avidity antigen recognizing constructs, such as antibodies or T cell receptors, which specifically bind to the melanoma associated antigen (MAGE) A1. The constructs of the invention are particularly useful for the diagnosis, prevention or therapy of tumorous diseases which are characterized by the specific expression of the MAGE-A1 antigen. Furthermore provided are nucleic acids, vectors and host cells—such as CD4 or CD8 positive T cells—which encode, comprise or present the antigen recognizing constructs of the invention. The invention thus provides new means for immune therapy, specifically adoptive T cell therapy, for treating cancer.

BACKGROUND OF INVENTION

Despite remarkable technological advancements in the diagnosis and treatment options available to patients diagnosed with cancer, the prognosis still often remains poor and many patients cannot be cured. Immunotherapy holds the promise of offering a potent, yet targeted, treatment to patients diagnosed with various tumors, with the potential to eradicate the malignant tumor cells without damaging normal tissues. In theory the T cells of the immune system are capable of recognizing protein patterns specific for tumor cells and to mediate their destruction through a variety of effector mechanisms. Adoptive T-cell therapy is an attempt to harness and amplify the tumor-eradicating capacity of a patient's own T cells and then return these effectors to the patient in such a state that they effectively eliminate residual tumor, however without damaging healthy tissue. Although this approach is not new to the field of tumor immunology, still many drawbacks in the clinical use of adoptive T cell therapy impair the full use of this approach in cancer treatments.

A TCR is a heterodimeric cell surface protein of the immunoglobulin super-family which is associated with invariant proteins of the CD3 complex involved in mediating signal transduction. TCRs exist in $\alpha\beta$ and $\gamma\delta$ forms, which are structurally similar but have quite distinct anatomical locations and probably functions. The extracellular portion of native heterodimeric $\alpha\beta$TCR consists of two polypeptides, each of which has a membrane-proximal constant domain, and a membrane-distal variable domain. Each of the constant and variable domains includes an intra-chain disulfide bond. The variable domains contain the highly polymorphic loops analogous to the complementarity determining regions (CDRs) of antibodies. The use of TCR gene therapy overcomes a number of current hurdles. It allows equipping patients' own T cells with desired specificities and generation of sufficient numbers of T cells in a short period of time, avoiding their exhaustion. The TCR will be transduced into central memory T cells or T cells with stem cell characteristics, which may ensure better persistence and function upon transfer. TCR-engineered T cells will be infused into cancer patients rendered lymphopenic by chemotherapy or irradiation, allowing efficient engraftment but inhibiting immune suppression. Transgenic mice expressing human MHC molecules and a diverse human TCR repertoire serve as a tool to rapidly analyze whether peptide antigens are immunogenic, i.e. are they efficiently processed and presented by MHC molecules, do they efficiently induce T cell responses following immunization (Li et al. 2010 Nat Med). The concept of adoptive T cell therapy using the ABabDII mouse published by Li et al is shown in FIG. 1.

In brief, CD8+ T cells in ABabDII mice harbor human T cell receptors (TCRs) which recognize antigens presented by human MHC class I molecules. As opposed to humans, ABabDII mice are not tolerant to human tumor associated antigens (TAAs). Therefore, when vaccinated with a human TAA, ABabDII mice generate an efficient adaptive immune response against those foreign antigens including the expansion of high avidity antigen specific T cells (FIG. 1, right side). After immunization with a suitable human TAA the genetic information coding for the high avidity TCRs of the ABabDII mice can be extracted (FIG. 1, center). These TCRs can subsequently be re-expressed in T cells from tumor patients through retroviral transduction. Those re-targeted T cells can be transferred back into the patient fighting the tumor (FIG. 1, left side).

Using the human TCR transgenic mouse, any human peptide sequence not encoded by the mouse genome is thus suitable for immunization and will yield TCRs with optimal affinity. Optimal affinity means that the T cells are restricted to human self-MHC molecules and recognize the peptide antigen as foreign, e.g. represent the non-tolerant repertoire. By using peptide/MHC multimers, specific T cells of the transgenic mice can be sorted, human TCRs isolated, e.g. by single cell PCR, the TCRs optimized for efficient expression while avoiding mispairing with endogenous TCR and used for transduction of patients' T cells with viral vectors (Uckert et al. 2008 Cancer Immunol Immunother; Kammertoens T et al. 2009 Eur J Immunol).

The melanoma antigen genes (MAGE-A) were found to be expressed in a variety of tumors of different histological origin. Proteins encoded by the MAGE genes are tumor rejection antigens, which can induce specific cytotoxic T-lymphocytes (CTL) having the ability to recognize and kill cancerous cells. MAGE genes and proteins are thus a preferential target for the development of novel drugs to fight cancer by immunotherapy. MAGE-A proteins constitute a sub-family of Cancer-Testis Antigens which are expressed mainly, but not exclusively, in the germ line. They are however also expressed in various human cancers where they are associated with, and may drive, malignancy. This specific expression of MAGE antigens in tumors and not the normal surrounding healthy tissue makes this family of antigens very interesting for targeted adoptive T cell transfer. However, to date no satisfactory immune therapy is known due to the lack of specific and highly avid antibodies or T cell receptors targeting the MAGE antigen.

BRIEF SUMMARY

In view of the above described major drawbacks in the background art, it is the objective of the present invention to provide new antigen recognizing constructs with high avidity and specificity against the MAGE-A antigen. Furthermore, the present invention intends to provide novel methods that allow for the production of such constructs. In more general terms the invention seeks to provide novel means for immuno cancer therapy.

The present invention will now be further described in the following examples with reference to the accompanying figures and sequences, nevertheless, without being limited thereto. For the purposes of the present invention, all references as cited herein are incorporated by reference in their entireties. In the Figures and Sequences:

BRIEF DESCRIPTION OF SEQUENCES

Figure 1:
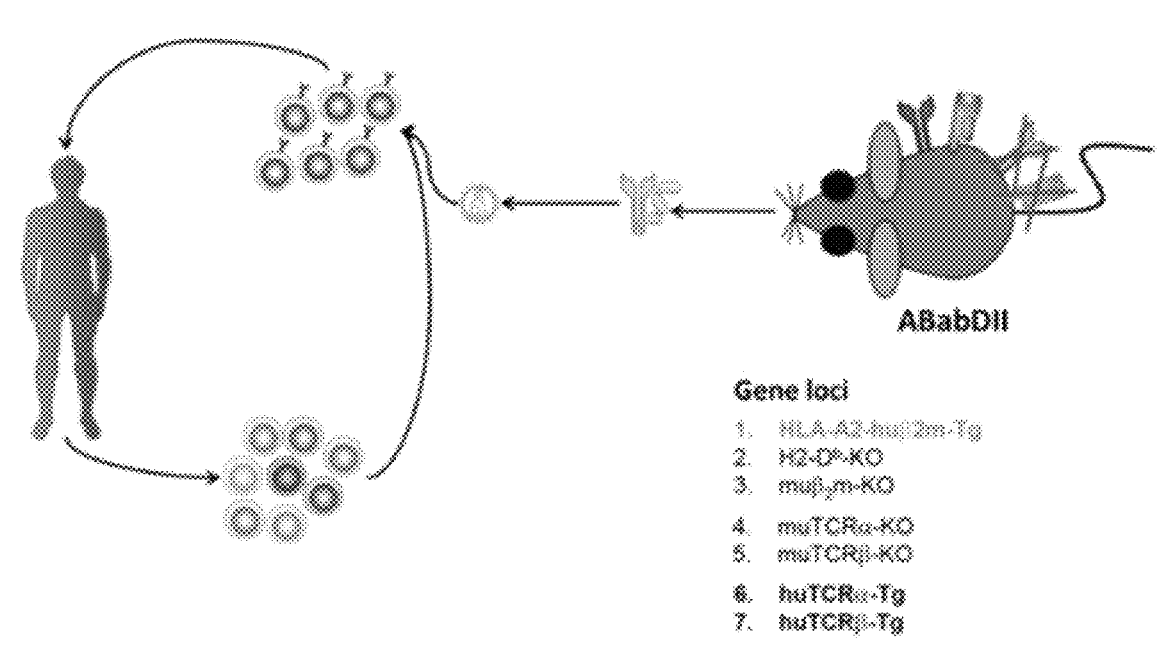
FIG. 1 shows the concept of adoptive T cell therapy.

SEQ ID NOs: 1 to 6 show alpha and beta CDR3 sequences of the TCRs of the invention.

SEQ ID NOs: 7 to 10 show alpha and beta chain CDR3 sequences of healthy humans.

SEQ ID NOs: 11 to 12 show the epitope sequences of human (11) and mouse (12) MAGE-A1.

SEQ ID NOs: 13 to 21 show the vector nucleotide sequences of FIGS. 8 to 16.

SEQ ID NOs: 22 to 39 show the complete amino acid sequences of the alpha and beta chains of the TCRs of the invention SEQ ID NOs: 40 to 51 show alpha and beta CDR1 and CDR2 sequences of Vα and Vβ genes.

DETAILED DISCLOSURE

The above problem is solved in a first aspect by an antigen recognizing construct comprising an amino acid sequence having at least 50%, 60%, 70%, 80%, 90%, 95%, 98%, 99% or 100% sequence identity to an amino acid sequence selected from SEQ ID Nos. 1 to 6. SEQ ID No 1 to 6 corresponds to CDR3 regions shown in FIG. 4 of this application. It was surprisingly discovered that the TCRs provided in the examples of the present invention are highly avid compared to state of the art TCRs directed at MAGE antigens. In one preferred embodiment of the present invention the antigen recognizing construct comprises a complementary determining region 3 (CDR3) having at least 50%, 60%, 70%, 80%, 90%, 95%, 98%, 99% or 100% sequence identity to an amino acid sequence selected from SEQ ID Nos. 1 to 6.

Preferred in the context of the invention is also that the antigen recognizing construct further comprises a V element selected from TRAV5, TRAV13-1, TRAV12-3, TRBV28, TRBV29-1, TRBV13, TRBV20, TRBV12, and/or a J element selected from TRAJ41, TRAJ29, TRAJ31, TRAJ49, TRAJ34, TRBJ2-7, TRBJ2-2, TRBJ2-6, TRBJ7, TRBJ1-2; preferably in the combination as depicted in table 1.

The antigen recognizing construct in accordance with the invention is specific for and/or binds specifically to an antigen of the melanoma associated antigen MAGE family. Various proteins are known to be part of the MAGE family which includes also some pseudo genes. One region of homology shared by all of the members of the MAGE family is a stretch of about 200 amino acids which has been named the MAGE conserved domain. The MAGE conserved domain is usually located close to the C-terminal, although it can also be found in a more central position in some proteins. The MAGE conserved domain is generally present as a single copy but it is duplicated in some proteins. MAGE genes which are detectable by the antigen recognizing constructs of the invention are selected from MAGE-B1, MAGE-A1, MAGE-A10, MAGE-A11, MAGE-A12, MAGE-A2B, MAGE-A3, MAGE-A4, MAGE-A6, MAGE-A8, MAGE-A9, MAGE-B1, MAGE-B10, MAGE-B16, MAGE-B18, MAGE-B2, MAGE-B3, MAGE-B4, MAGE-B5, MAGE-B6, MAGE-B6B, MAGE-C1, MAGE-C2, MAGE-C3, MAGE-D1, MAGE-D2, MAGE-D4, MAGE-E1, MAGE-E2, MAGE-F1, MAGE-H1, MAGE-L2, NDN, NDNL2. Preferred in the context of the present invention are the 12 homologous MAGE proteins selected from MAGE-A1, MAGE-A2, MAGE-A3, MAGE-A4, MAGE-A5, MAGE-A6, MAGE-A7, MAGE-A8, MAGE-A9, MAGE-A10, MAGE-A11, or MAGE-A12. Most preferred is an antigen recognizing construct having specificity for MAGE-A1.

The term "specificity" or "antigen specificity" or "specific for" a given antigen, as used herein means that the antigen recognizing construct can specifically bind to and immunologically recognize said antigen, preferably MAGE-A1, more preferably with high avidity. For example, a TCR may be considered to have "antigenic specificity" for MAGE-A1 if T cells expressing the TCR secrete at least about 200 pg/ml or more (e.g., 250 pg/ml or more, 300 pg/ml or more, 400 pg/ml or more, 500 pg/ml or more, 600 pg/ml or more, 700 pg/ml or more, 1000 pg ml or more, 2,000 pg/ml or more, 2,500 pg/ml or more, 5,000 pg/ml or more) of interferon γ (IFN-γ) upon co-culture with target cells pulsed with a low concentration of a MAGE peptide, such as the MAGE-A1 HLA-A02 restricted MAGE-A1$_{278-286}$ peptide (e.g., about $10^{-11}$ mol/l, $10^{-10}$ mol/l, $10^{-9}$ mol/l, $10^{-8}$ mol/l, $10^{-7}$ mol/l, $10^{-6}$ mol/l, $10^{-5}$ mol/l). Alternatively or additionally, a TCR may be considered to have "antigenic specificity" for MAGE-A1 if T cells expressing the TCR secrete at least twice as much IFN-γ as the untransduced background level of IFN-γ upon co-culture with target cells pulsed with a low concentration of HLA-A02 restricted MAGE-A1. Such a "specificity" as described above can—for example—be analyzed with an ELISA.

Preferred embodiments of the present invention disclose antigen recognizing constructs which are in the form of an antibody, or derivative or fragment thereof, or a T cell receptor (TCR), or derivative or fragment thereof. Fragments or derivatives of the herein disclosed antibodies or TCRs preferably still harbor the antigenic specificity (the binding function with respect to the antigen) as the original antibody or TCR, respectively.

Native alpha-beta heterodimeric TCRs have an alpha chain and a beta chain. Each chain comprises variable, joining and constant regions, and the beta chain also usually contains a short diversity region between the variable and joining regions, but this diversity region is often considered as part of the joining region. Each variable region comprises three CDRs (Complementarity Determining Regions) embedded in a framework sequence, one being the hypervariable region named CDR3. There are several types of alpha chain variable (Vα) regions and several types of beta chain variable (Vβ) regions distinguished by their framework, CDR1 and CDR2 sequences, and by a partly defined CDR3 sequence. The Vα types are referred to in IMGT nomenclature by a unique TRAV number.

Thus, a further embodiment of the present invention pertains to an ARC comprising an alpha chain variable region, wherein said alpha chain variable region comprises a CDR1, CDR2 and CDR3 that comprise an amino acid sequence that is at least 50%, 60%, 70%, 80%, 90%, 95%, 98%, 99% or preferably 100% identical to the amino acid sequence of the corresponding CDR1 and CDR2 of the Vα-type TRAV5 (according to IMGT nomenclature) and CDR3: CAESIGSNSGYALNF (SEQ ID NO:1); or a CDR1 and CDR2 of the Vα-type TRAV13-1 and CDR3: CAARPNSGNTPLVF (SEQ ID NO:2); or a CDR1 and CDR2 of the Vα-type TRAV12-3 and CAMSDTGNQFYF (SEQ ID NO:3).

Another embodiment of the present invention pertains to an ARC comprising a beta chain variable region, wherein said beta chain variable region comprises a CDR1, CDR2 and CDR3 that comprise an amino acid sequence that is at least 50%, 60%, 70%, 80%, 90%, 95%, 98%, 99% or preferably 100% identical to the respective amino acid sequence of a CDR1 and CDR2 of the Vβ-type TRBV28 (according to IMGT nomenclature) and CDR3: CASRGLAGYEQYF (SEQ ID NO:4); or a CDR1 and CDR2 of the Vβ-type TRBV29-1 and CDR3: CSVEQDTNTGELFF (SEQ ID NO:5); or a CDR1 and CDR2 of the Vβ-type TRBV13 and the CDR3: CASSFRGGGANVLTF (SEQ ID NO:6).

In one preferred embodiment the aforementioned ARC comprises an alpha chain and beta chain with the above referenced variable regions, preferably in the combination as indicated in table 1 below.

Preferred are ARCs of the invention which comprise at least one, preferably all three CDR sequences CDR1, CDR2 and CDR3. ARCs of the invention may comprise:

CDR 1 and CDR2 regions of the respective known Vα and Vβ types are according to the IMGT database:

```
TRAV5:
CDR1:
                                    (SEQ ID NO: 40)
    DSSSTY,

CDR2:
                                    (SEQ ID NO: 41)
    IFSNMDM

TRAV13-1:
CDR1:
                                    (SEQ ID NO: 42)
    DSASNY,

CDR2:
                                    (SEQ ID NO: 43)
    IRSNVGE

TRAV12-3:
CDR1:
                                    (SEQ ID NO: 44)
    NSAFQY,

CDR2:
                                    (SEQ ID NO: 45)
    TYSSGN
```

-continued

TRBV28:
CDR1:
(SEQ ID NO: 46)
MDHEN,

CDR2:
(SEQ ID NO: 47)
SYDVKM.

TRBV29-1:
CDR1:
(SEQ ID NO: 48)
SQVTM,

CDR2:
(SEQ ID NO: 49)
ANQGSEA

TRBV13:
CDR1:
(SEQ ID NO: 50)
PRHDT,

CDR2:
(SEQ ID NO: 51)
FYEKMQ.

Therefore, an ARC of the invention in a preferred embodiment comprises an alpha chain comprising the CDR sequences shown in SEQ ID NO: 40, 41 and 1; or SEQ ID NO: 42, 43, and 2; or SEQ ID NO: 44, 45, and 3. Alternatively or additionally the ARC of the invention comprises a beta chain having the sequences shown in SEQ ID NO: 46, 47, and 4; or SEQ OD NO: 48, 49, and 5; or SEQ ID NO: 50, 51, and 6.

Preferred according to the invention is a TCR or an antibody, or their respective antigenic binding fragments, with
 a. an alpha chain comprising the CDR sequences shown in SEQ ID NO: 40, 41, and 1; and a beta chain comprising the CDR sequences shown in SEQ ID NO: 46, 47, and 4; or
 b. an alpha chain comprising the CDR sequences shown in SEQ ID NO: 42, 43, and 2; and a beta chain comprising the CDR sequences shown in SEQ ID NO: 48, 49, and 5; or
 c. an alpha chain comprising the CDR sequences shown in SEQ ID NO: 44, 45, and 3; and a beta chain comprising the CDR sequences shown in SEQ ID NO: 50, 51, and 6.

The ARC is in preferred embodiments selected from an antibody or a TCR, but TCRs are preferred.

For the purposes of the present invention, a TCR is a moiety having at least one TCR alpha and/or TCR beta variable domain. Generally they comprise both a TCR alpha variable domain and a TCR beta variable domain. They may be αβ heterodimers or may be single chain format. For use in adoptive therapy, an αβ heterodimeric TCR may, for example, be transfected as full length chains having both cytoplasmic and transmembrane domains. If desired, an introduced disulfide bond between residues of the respective constant domains may be present.

In one preferred embodiment of the first aspect of the invention, the antigen recognizing construct is as described above a TCR. The TCR preferably comprises at least one alpha and/or beta TCR chain, wherein said TCR chain is encoded by at least one nucleic acid, the nucleic acid comprising a nucleotide sequence selected from (i) the TCR chain encoding sequences comprised in SEQ ID No. 13 to 21, or (ii) a sequence having at least 50%, 60%, 70%, 80%, 90%, 95%, 98%, 99% or 100% identity to a TCR encoding sequence comprised in SEQ ID No. 13 to 21, or (iii) a sequence that due to the degeneracy of the genetic code encodes for an identical TCR as any one of the TCR en-coding sequences comprised in SEQ ID No. 13 to 21, but has a different sequence.

SEQ ID Nos. 13 to 21 depict the nucleotide sequences of the vector maps of FIGS. 8 to 16. Each of these vectors comprise an alpha and a beta chain of a TCR of the present invention. In the figures the beta chain is located upstream of the alpha chain sequence. As also described below, the invention exemplary describes three isolated TCRs, which were to different degrees optimized by murinization of the original sequence of the constant domain of the TCR chains. The abbreviation in the vector designation "hc" stands for the complete human variant of the TCR, "mc" for a complete murinized constant domain in the TCR chain, whereas "mmc" depicts minimal murinization in the constant domain of the TCR chain. The exact location of the alpha and beta chains in the vector maps (and thus in the corresponding sequences) can be derived from the figure legend.

In one preferred embodiment of alternative (i) as described before, the TCR comprises the alpha and beta chain sequence as comprised together in any one of SEQ ID No. 13 to 21.

In one additional preferred embodiment of the first aspect of the invention, the antigen recognizing construct is as described above a TCR. The TCR preferably comprises at least one alpha and/or beta TCR chain, wherein said TCR chain comprises an amino acid sequence according to any one of the TCR chains shown in SEQ ID Nos. 22-39, or an amino acid sequence having at least 50%, 60%, 70%, 80%, 90%, 95%, 98%, 99% or 100% identity to an amino acid sequence shown in SEQ ID No. 22 to 39.

An scTCR can comprise a polypeptide of a variable region of a first TCR chain (e.g., an alpha chain) and a polypeptide of an entire (full-length) second TCR chain (e.g., a beta chain), or vice versa. Furthermore, the scTCR can optionally comprise one or more linkers which join the two or more polypeptides together. The linker can be, for instance, a peptide which joins together two single chains, as described herein.

Also provided is such a scTCR of the invention, which is fused to a human cytokine, such as IL-2, IL-7 or IL-15.

The antigen recognizing construct according to the invention can also be provided in the form of a multimeric complex, comprising at least two scTCR molecules, wherein said scTCR molecules are each fused to at least one biotin moiety, and wherein said scTCRs are interconnected by biotin-strepavidin interaction to allow the formation of said multimeric complex. Also provided are multimeric complexes of a higher order, comprising more than two scTCR of the invention.

In one embodiment the antigen recognizing construct according to the invention is an antibody, or a fragment thereof. The term "antibody" in its various grammatical forms is used herein to refer to immunoglobulin molecules and immunologically active portions of immunoglobulin molecules, i.e., molecules that contain an antibody combining site or a paratope. Such molecules are also referred to as "antigen binding fragments" of immunoglobulin molecules. The invention further provides an antibody, or antigen binding portion thereof, which specifically binds to the antigens described herein. The antibody can be any type of immunoglobulin that is known in the art. For instance, the antibody can be of any isotype, e.g., IgA, IgD, IgE, IgG, IgM, etc. The antibody can be monoclonal or polyclonal.

The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form.

The invention also provides antigen binding portions of any of the antibodies described herein. The antigen binding portion can be any portion that has at least one antigen binding site, such as Fab, F(ab')2, dsFv, sFv, diabodies, and triabodies. A single-chain variable region fragment (sFv) antibody fragment, which consists of a truncated Fab fragment comprising the variable (V) domain of an antibody heavy chain linked to a V domain of a light antibody chain via a synthetic peptide, can be generated using routine recombinant DNA technology techniques. Similarly, disulfide-stabilized variable region fragments (dsFv) can be prepared by recombinant DNA technology, antibody fragments of the invention, however, are not limited to these exemplary types of antibody fragments. Also, the antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

In an embodiment of the invention the antigen recognizing construct binds to a human leucocyte antigen (HLA) presented peptide, preferably by HLA-A02, of MAGE. In a preferred embodiment the antigen recognizing construct specifically binds to the human MAGE-A1$_{278\text{-}286}$ epitope.

In a preferred embodiment the antigen recognizing construct is a human TCR, or fragment or derivative thereof. A human TCR or fragment or derivative thereof is a TCR which comprises over 50% of the corresponding human TCR sequence. Preferably only a small part of the TCR sequence is of artificial origin or derived from other species. It is known however, that chimeric TCRs e.g. from human origin with murine sequences in the constant domains, are advantageous. Particularly preferred are therefore TCRs in accordance with the present invention, which contain murine sequences in the extracellular part of their constant domains.

Thus, it is also preferred that the inventive antigen recognizing construct is able to recognize its antigen in a human leucocyte antigen (HLA) dependent manner, preferably in a HLA-A02 dependent manner. The term "HLA dependent manner" in the context of the present invention means that the antigen recognizing construct binds to the antigen only in the event that the antigenic peptide is presented by HLA.

The antigen recognizing construct in accordance with the invention in one embodiment preferably induces an immune response, preferably wherein the immune response is characterized by the increase in interferon (IFN) γ levels.

Figure 4:
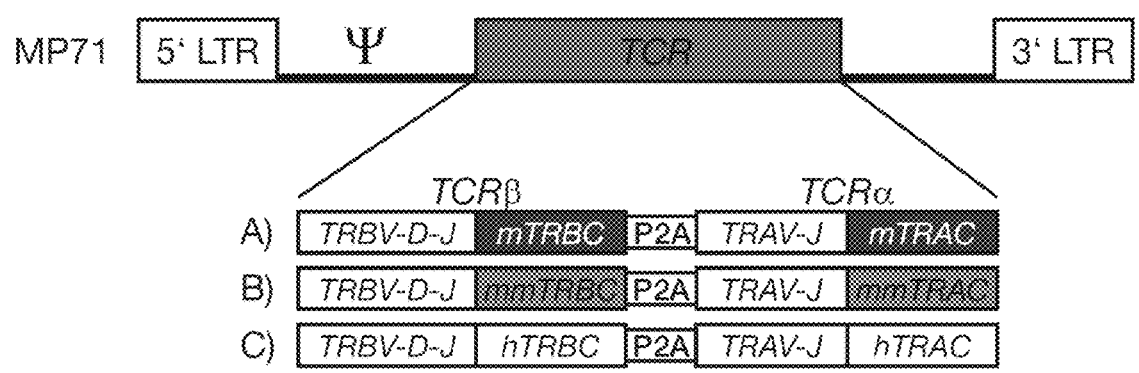
FIG. 4 shows a schematic representation of the TCR vectors.

A preferred embodiment of the invention pertains to the antigen recognizing construct which is a T cell receptor, and which comprises in its alpha chain a CDR3 having at least 50%, 60%, 70%, 80%, 90%, 95%, 98%, 99% or 100% sequence identity to an amino acid sequence selected from SEQ ID Nos. 1 to 3, and/or comprises in its beta chain an CDR3 having at least 50%, 60%, 70%, 80%, 90%, 95%, 98%, 99% or 100% sequence identity to an amino acid sequence selected from SEQ ID Nos. 4 to 6. Further preferred is a TCR wherein the alpha chain comprises an CDR3 having at least 50%, 60%, 70%, 80%, 90%, 95%, 98%, 99% or 100% sequence identity to SEQ ID No. 1, and the beta chain comprises an CDR3 having at least 50%, 60%, 70%, 80%, 90%, 95%, 98%, 99% or 100% sequence identity to SEQ ID No. 4; or wherein the alpha chain comprises an CDR3 having at least 50%, 60%, 70%, 80%, 90%, 95%, 98%, 99% or 100% sequence identity to SEQ ID No. 2, and the beta chain comprises an CDR3 having at least 50%, 60%, 70%, 80%, 90%, 95%, 98%, 99% or 100% sequence identity to SEQ ID No. 5; or wherein the alpha chain comprises an CDR3 having at least 50%, 60%, 70%, 80%, 90%, 95%, 98%, 99% or 100% sequence identity to SEQ ID No. 3, and the beta chain comprises an CDR3 having at least 50%, 60%, 70%, 80%, 90%, 95%, 98%, 99% or 100% sequence identity to SEQ ID No. 6. Preferably, the CDR3 regions are combined with a CDJ element as depicted in any of the figures, in particular in the combination as shown in FIG. 4.

Furthermore preferred is that the antigen recognizing construct of the invention, which is a T cell receptor, comprises an amino acid sequence having at least 50%, 60%, 70%, 80%, 90%, 95%, 98%, 99% or 100% sequence identity to an amino acid sequence shown in SEQ ID No. 22 to 39. Particularly preferred are TCRs having at least 50%, 60%, 70%, 80%, 90%, 95%, 98%, 99% or 100% sequence identity to a TCR selected from TCR1367hc, TCR1367mc, TCR1367mmc, TCR1405hc, TCR1405mc, TCR1405mmc, TCR1705hc, TCR1705mc an TCR1705mmc. Most preferred is a TCR selected from the group consisting of TCR1367hc, TCR1367mc, TCR1367mmc, TCR1405hc, TCR1405mc, TCR1405mmc, TCR1705hc, TCR1705mc an TCR1705mmc. The amino acid sequences of the above referenced TCRs of the invention are depicted in SEQ ID No. 22 to 39.

The antigen recognizing construct in accordance with the invention are high avidity TCRs.

The problem of the invention is solved in another aspect by providing a nucleic acid encoding for an antigen recognizing construct in accordance with the present invention. The nucleic acid preferably (a) has a strand encoding for an antigen recognizing construct according to the invention; (b) has a strand complementary to the strand in (a); or (c) has a strand that hybridizes under stringent conditions with a molecule as described in (a) or (b). Stringent conditions are known to the person of skill in the art, specifically from Sambrook et al, "Molecular Cloning". In addition to that, the nucleic acid optionally has further sequences which are necessary for expressing the nucleic acid sequence corresponding to the protein, specifically for expression in a mammalian/human cell. The nucleic acid used can be contained in a vector suitable for allowing expression of the nucleic acid sequence corresponding to the peptide in a cell. However, the nucleic acids can also be used to transform a presenting cell, which shall not be restricted to classical antigen-presenting cells such as dendritic cells, in such a way that they themselves produce the corresponding proteins on their cellular surface.

By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide.

Preferably, the nucleic acids of the invention are recombinant. As used herein, the term "recombinant" refers to (i)

molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication. The nucleic acid can comprise any nucleotide sequence which encodes any of the TCRs, polypeptides, or proteins, or functional portions or functional variants thereof described herein.

Furthermore, the invention provides a vector comprising a nucleic acid in accordance to the invention as described above. Desirably, the vector is an expression vector or a recombinant expression vector. The term "recombinant expression vector" refers in context of the present invention to a nucleic acid construct that allows for the expression of an mRNA, protein or polypeptide in a suitable host cell. The recombinant expression vector of the invention can be any suitable recombinant expression vector, and can be used to transform or transfect any suitable host. Suitable vectors include those designed for propagation and expansion or for expression or both, such as plasmids and viruses. Examples of animal expression vectors include pEUK-Cl, pMAM and pMAMneo. Preferably, the recombinant expression vector is a viral vector, e.g., a retroviral vector. The recombinant expression vector comprises regulatory sequences, such as transcription and translation initiation and termination codons, which are specific to the type of host cell (e.g., bacterium, fungus, plant, or animal) into which the vector is to be introduced and in which the expression of the nucleic acid of the invention shall be performed. Furthermore, the vector of the invention may include one or more marker genes, which allow for selection of transformed or transfected hosts. The recombinant expression vector can comprise a native or normative promoter operably linked to the nucleotide sequence encoding the constructs of the invention, or to the nucleotide sequence which is complementary to or which hybridizes to the nucleotide sequence encoding the constructs of the invention. The selection of promoters include, e.g., strong, weak, inducible, tissue-specific and developmental-specific promoters. The promoter can be a non-viral promoter or a viral promoter. The inventive recombinant expression vectors can be designed for either transient expression, for stable expression, or for both. Also, the recombinant expression vectors can be made for constitutive expression or for inducible expression.

The invention also pertains to a host cell comprising an antigen recognizing construct in accordance with the invention. Specifically the host cell of the invention comprises a nucleic acid, or a vector as described herein above. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. For purposes of producing a recombinant TCR, polypeptide, or protein, the host cell is preferably a mammalian cell. Most preferably, the host cell is a human cell. While the host cell can be of any cell type, can originate from any type of tissue, and can be of any developmental stage, the host cell preferably is a peripheral blood leukocyte (PBL) or a peripheral blood mononuclear cell (PBMC). More preferably, the host cell is a T cell. The T cell can be any T cell, such as a cultured T cell, e.g., a primary T cell, or a T cell from a cultured T cell line, e.g., Jurkat, SupT1, etc., or a T cell obtained from a mammal, preferably a T cell or T cell precurser from a human patient. If obtained from a mammal, the T cell can be obtained from numerous sources, including but not limited to blood, bone marrow, lymph node, the thymus, or other tissues or fluids. T cells can also be enriched for or purified. Preferably, the T cell is a human T cell. More preferably, the T cell is a T cell isolated from a human. The T cell can be any type of T cell and can be of any developmental stage, including but not limited to, CD4positive and/or CD8positive, CD4 positive helper T cells, e.g., Th1 and Th2 cells, CD8 positive T cells (e.g., cytotoxic T cells), tumor infiltrating cells (TILs), memory T cells, naive T cells, and the like. Preferably, the T cell is a CD8 positive T cell or a CD4 positive T cell.

Preferably, the host cell of the invention is a lymphocyte, preferably a T lymphocyte, such as a CD4 or CD8 positive T-cell. The host cell furthermore preferably is a tumor reactive T cell specific for MAGE-A1 expressing tumor cells.

One further aspect of the present invention relates to the herein disclosed antigen recognizing constructs, nucleic acids, vectors and/or host cell for use in medicine. The use in medicine in one preferred embodiment includes the use in the diagnosis, prevention and/or treatment of a proliferative disease, such as a malignant or benign tumor disease.

Thus also provided by the present invention is a method for treating a subject suffering from a tumor or tumor disease comprising the administration of the antigen recognizing constructs, nucleic acids, vectors and/or host cell as disclosed by the present invention. Preferably the subject is a subject in need of such a treatment. The subject in preferred embodiments is a mammalian subject, preferably a human patient, suffering from a tumor or tumor disease.

In one preferred aspect of the invention the tumor or tumor disease is a disease characterized by the expression of a MAGE antigen as described herein above. Most preferably the tumor or tumor disease expresses the MAGE-A1 antigen, even more preferably wherein the tumor or tumor disease presents via HLA the MAGE-A1$_{278-286}$ epitope. Further preferred is that the tumor or tumor disease is characterized by the differential expression of the MAGE-A1 antigen compared to healthy tissue. The MAGE-A1 antigen may be expressed to a low extend in normal (non-cancerous) cells, whereas the antigen is significantly stronger expressed in the tumor cells.

Also, in one preferred aspect of the invention the expression of MAGE-A1 in the tumor is induced or enhanced by prior pharmacologic treatment, e.g. with 5-aza-2-deoxycitabine.

The term "tumor" or "tumor disease" in the context of the present invention denotes a disease selected from melanomas, hepatocellular carcinomas, intra- and extrahepatic cholangiocellular carcinomas, squamous cell carcinomas, adenocarcinomas as well as undifferentiated carcinomas of the head, neck, lung or esophagus, colorectal carcinomas, chondrosarcomas, osteosarcomas, medulloblastomas, neuroblastomas, non-squamous cell carcinomas of the head or neck, ovarian tumors, lymphomas, acute and chronic lymphocytic leukemias, acute and chronic myeloid leukemia, bladder carcinomas, prostate carcinomas, pancreatic adenocarcinomas, mammary carcinomas and gastric carcinomas. Preferred diseases to be treated by the products and/or methods of the invention include melanoma, non-small-cell lung cancer, pancreatic adenocarcinoma and cholangiocellular carcinoma.

One preferred medicinal use of the invention relates to immune therapy, preferably adoptive T cell therapy. The product and methods of the invention are particularly useful in the context of adoptive T cell therapy. The administration of the compounds of the invention can for example involve the infusion of T cells of the invention into said patient. Preferably such T cells are autologous T cells of the patient which were in vitro transduced with a nucleic acid or antigen recognizing constructs of the present invention.

The invention in one further aspect discloses a method for the manufacturing of a MAGE-A1 specific antigen recognizing construct (ARC) expressing cell line, comprising
a. Providing a suitable host cell,
b. Providing a genetic construct encoding for an ARC, wherein said ARC comprises a CDR3 having an amino acid sequence with at least 50%, 60%, 70%, 80%, 90%, 95%, 98%, 99% or 100% sequence identity to an amino acid sequence selected from SEQ ID Nos. 1 to 6,
c. Introducing into said suitable host cell said genetic construct,
d. Expressing said genetic construct by said suitable host cell.

The above method may in one preferred embodiment further comprise the step of including a cell surface presentation of said ARC.

Of course it is also preferred that context of this aspect of the invention said ARC is an ARC according to the inventive aspects as described herein above. In this respect it is also additionally or alternatively preferred that said ARC is of mammalian origin, preferably of human origin.

The preferred suitable host cell for use in the method of the invention is a mammalian, in particular a human cell, such as a human T-cell. T cells for use in the invention are described in detail herein above.

The ARC produced according to the method of the invention is in one embodiment a TCR. For example also included are TCRs with additional (functional) domains or a TCR provided with alternative domains, e.g. a TCR provided with a foreign transmembrane-domain as membrane anchor. A TCR produced in accordance with the present invention is for example an alpha/beta TCR, gamma/delta TCR or a single chain TCR (scTCR). Also, TCR forms which are included by the present invention are generally any TCR known in the art, specifically those described herein above.

Desirably, the transfection system for use in the method in accordance with the invention is a retroviral vector system. Such systems are well known to the skilled artisan.

Also comprised by the present invention is in one embodiment the additional method step of purification of the ARC from the cell and, optionally, the reconstitution of the translated ARC-fragments in a T-cell.

In an alternative aspect of the invention a T-cell is provided obtained or obtainable by a method for the production of a T cell receptor (TCR), which is specific for tumorous cells and has high avidity as described herein above. Such a T cell is depending on the host cell used in the method of the invention for example a human or non-human T-cell, preferably a human TCR.

Thus also provided is a pharmaceutical composition, comprising any of the herein described products of the invention, specifically any proteins, nucleic acids or host cells. In a preferred embodiment the pharmaceutical composition is for immune therapy.

Examples of pharmaceutically acceptable carriers or diluents useful in the present invention include stabilizers such as SPGA, carbohydrates (e.g. sorbitol, mannitol, starch, sucrose, glucose, dextran), proteins such as albumin or casein, protein containing agents such as bovine serum or skimmed milk and buffers (e.g. phosphate buffer).

EXAMPLES

Example 1: Generation of T-Cells with a MAGE Epitope Using the ABabDII Mouse

Figure 2:
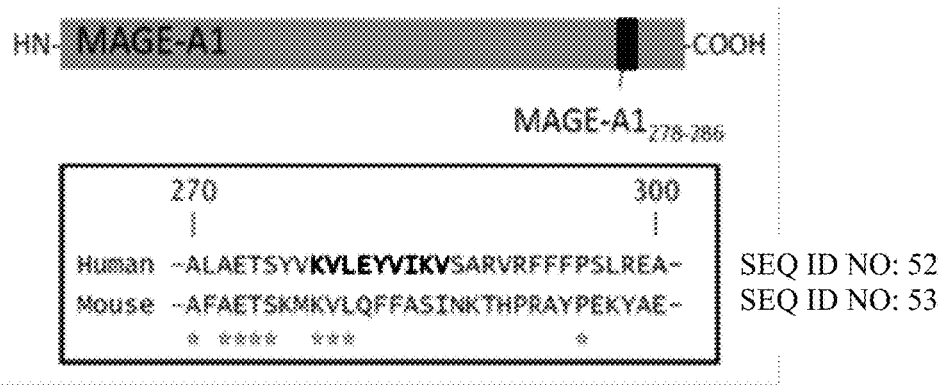
FIG. 2 shows MAGE-A1 and its epitope localization.

FIG. 2 shows the location of the HLA-A2 restricted epitope MAGE-A1$_{278-286}$ is shown in relation to the full-length MAGE-A1 protein (top). The human MAGE-A1$_{278-286}$ epitope is sufficiently different from its mouse homologue to prevent tolerance against human MAGE-A1$_{278-286}$ in ABabDII mice (bottom).

MAGE-A1 is expressed in a variety of human tumors, whereas its expression on normal human tissue is believed to be restricted to the testes. Therefore, specific targeting of MAGE-A1 expressing cells should limit toxicity to a minimum.

Figure 3:
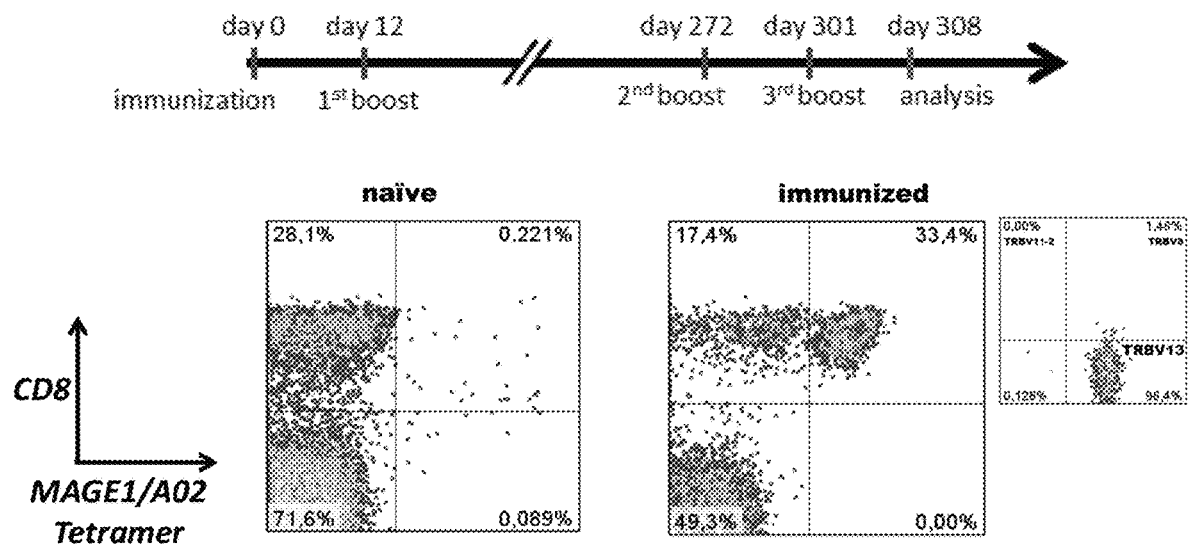
FIG. 3 shows the immune response against MAGE-A1 in ABabDII mice.

ABabDII mice were immunized with a 30mer peptide encompassing the nonamer MAGE-A1$_{278-286}$ plus CpG in incomplete Freund's adjuvant. Boosts were performed with the nonamer MAGE-A1$_{278-286}$ plus CpG in incomplete Freund's adjuvant. On the day of analysis, blood was taken and stained with a MAGE-A1/HLA-A2 specific tetramer and with antibodies for certain TRBV chains (IMGT nomenclature). After several boosts a monoclonal population of MAGE-A1 specific T cells is detectable in the blood of ABabDII mice. FIG. 3 shows the immune response of the immunized animal and the immunization scheme. A significant shift in FACS analysis of the immunized cells is observed with the tetramer staining indicating that MAGE specific T cells were generated.

Example 2: Isolation and Characterization of T Cell Receptors

The cDNA from MAGE-A1 specific T cell clones as generated in Example 1 was amplified by 5'-RACE and sequenced.

The table 1 shows the amino acid sequences of complementary determining region 3 (CDR3) of the alpha and beta chains for three different TCRs from ABabDII mice and two TCRs obtained from healthy humans (Ottaviani, S., Zhang, Y., Boon, T., & van der Bruggen, P. (2005). *A MAGE-1 antigenic peptide recognized by human cytolytic T lymphocytes on HLA- A2 tumor cells. Cancer Immunology, Immunotherapy: CII*, 54(12), 1214-1220).

TABLE 1

Amino acid sequences of the CDR3-regions for three different MAGE-A1 specific TCRs.

| TCR | alpha chain CDR3 | beta chain CDR3 |
| --- | --- | --- |
| 1367 | TRAV5-CAESIGSNSGYALNF-TRAJ41 (SEQ ID No. 1) | TRBV28-CASRGLAGYEQYF-TRBJ2-7 (SEQ ID No. 4) |
| 1405 | TRAV13-1-CAARPNSGNTPLVF-TRAJ29 (SEQ ID No. 2) | TRBV29-1-CSVEQDTNTGELFF-TRBJ2-2 (SEQ ID No. 5) |
| 1705 | TRAV12-3-CAMSDTGNQFYF-TRAJ49 (SEQ ID No. 3) | TRBV13-CASSFRGGGANVLTF-TRBJ2-6 (SEQ ID No. 6) |

TABLE 1-continued

Amino acid sequences of the CDR3-regions for three different MAGE-A1 specific TCRs.

| TCR | alpha chain CDR3 | beta chain CDR3 |
|---|---|---|
| CTL27* | TRAV5-CAESYNARLMF-TRAJ31 (SEQ ID No. 7) | TRBV20-CSAREPGQGPYEQYFG-TRBJ7 (SEQ ID No. 9) |
| CTL89* | TRAV5-CAGSGGGTDKLIF-TRAJ34 (SEQ ID No. 8) | TRBV12-CASLSGVYTFG-TRBJ1-2 (SEQ ID No. 10) |

*human repertoire see: Ottaviani et al. (2005). Cancer Immunology, Immunotherapy, 54(12), 1214-1220

The isolated TCR which comprise the above CDR3 sequences were then cloned. The retroviral vector MP71 is used for transduction of primary human peripheral blood lymphocytes (hPBLs). The alpha and beta genes of each TCR are linked with a P2A element which is cut by a cellular protease during translation of the transduced TCR ensuring equimolar expression of both chains (FIG. 4).

All genes are codon optimized for optimal expression. In order to further optimize expression in hPBLs additional modifications were introduced into the wild-type TCR constant regions. Complete (A) and minimal (B) murinization of the constant regions of the TCR chains usually result in higher expression levels in hPBLs than the unmodified human constant region (C).

Figure 5:
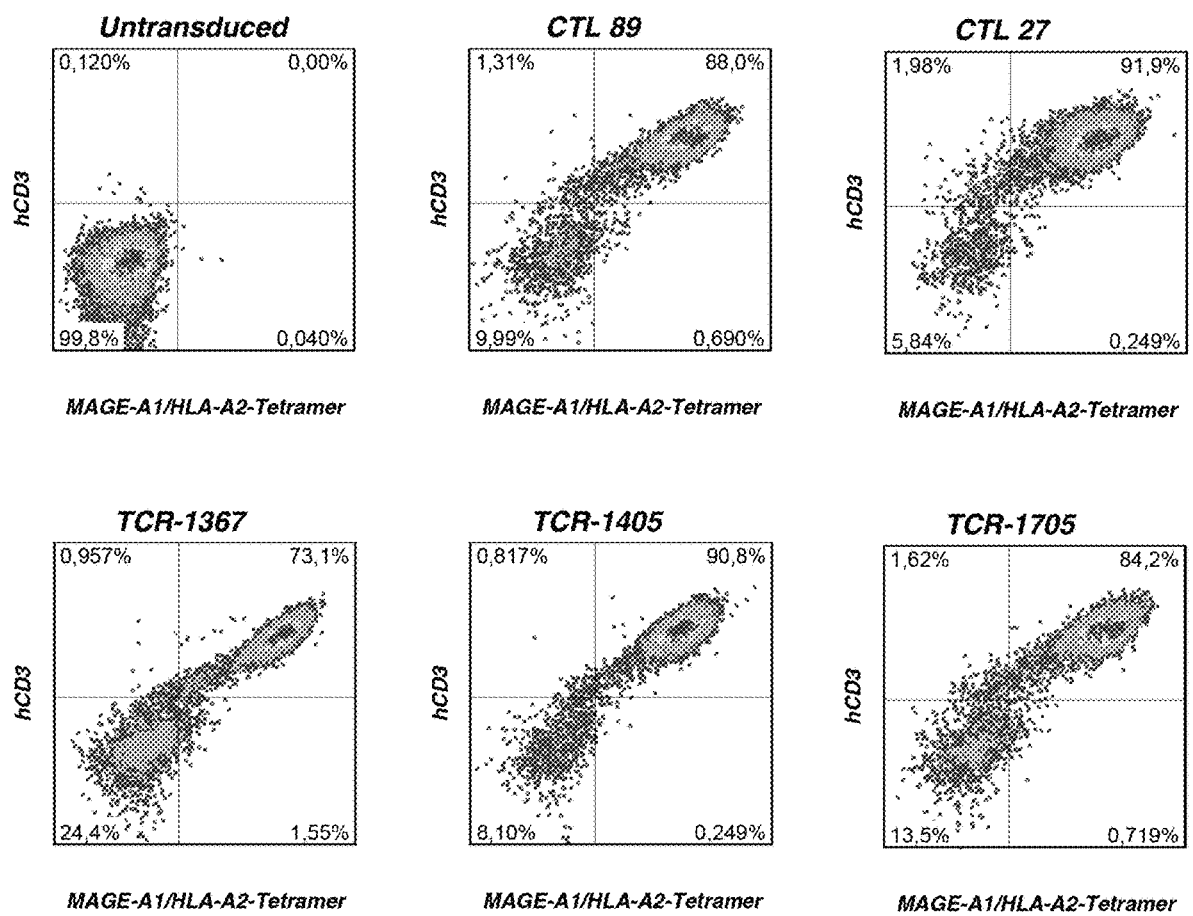
FIG. 5 shows FACS results of TCR transduced Jurkat 76 cells.

Then hCD8+ Jurkat 76 cells were transduced with different TCRs derived from ABabDII mice and human volunteers. Transduced cells stain positive for CD3. All transduced cells specifically bind the MAGE-A1/HLA-A2 tetramer (FIG. 5).

Surprisingly, the TCRs of the present invention provide an unusually high avidity compared to the TCRs of the state of the art. hPBLs were transduced with different MAGE-A1 specific TCRs. The transduced PBLs were then incubated with T2 cells, which had been pulsed with different concentrations of MAGE-A1$_{278-286}$ peptide. After overnight incubation IFNγ-production was measured by ELISA.

Figure 6:
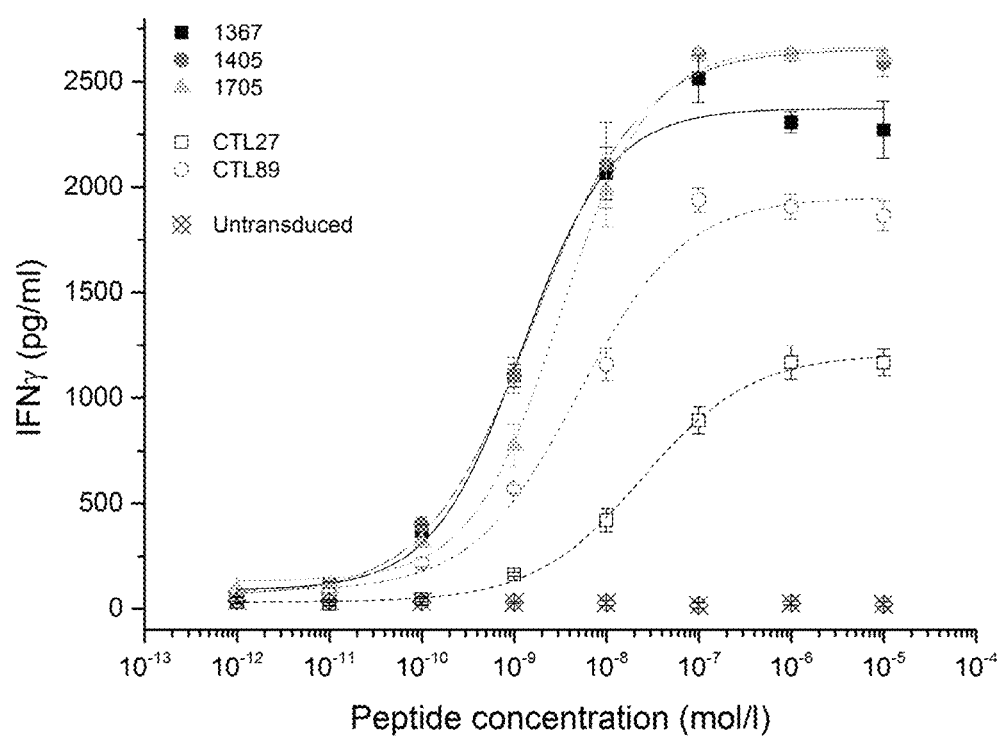
FIG. 6 shows the functional avidity of MAGE-A1 specific T cells.

In response to stimulation with peptide pulsed T2 cells the TCRs from ABabDII mice (FIG. 6, closed circles) show a response at lower peptide concentrations and a higher amount of IFNγ-production than the TCRs derived from the tolerant human system (FIG. 6, open circles).

Figure 7:
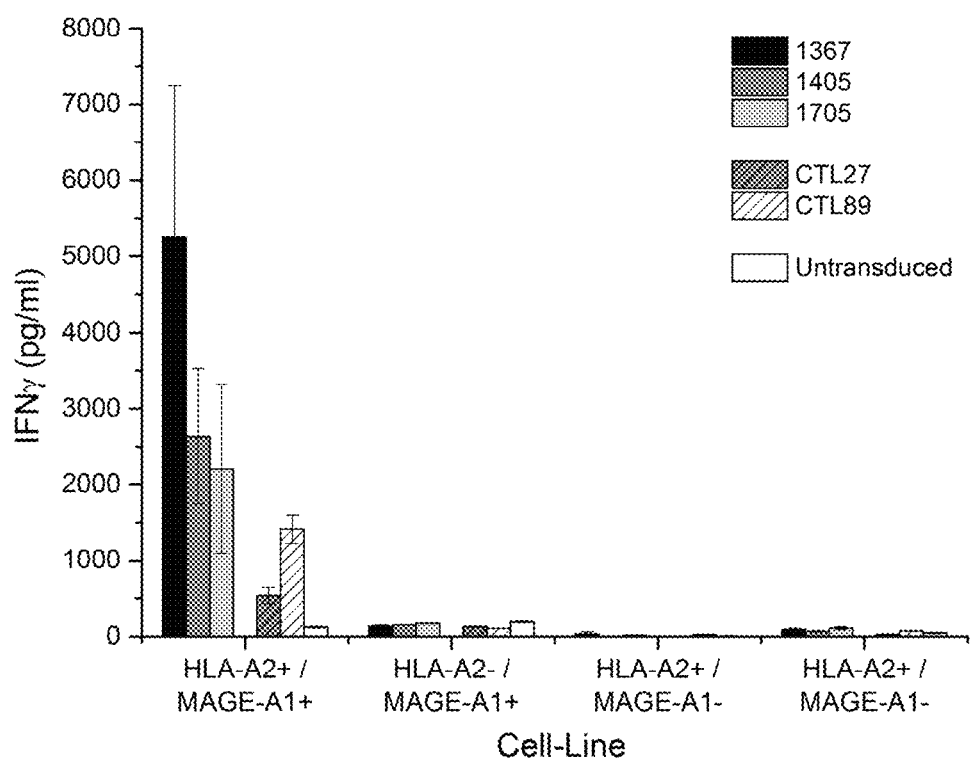
FIG. 7 shows the tumor cell recognition MAGE-A1 by T cells transduced with the MAGE-A1 specific TCRs of the invention.
Figure 8:
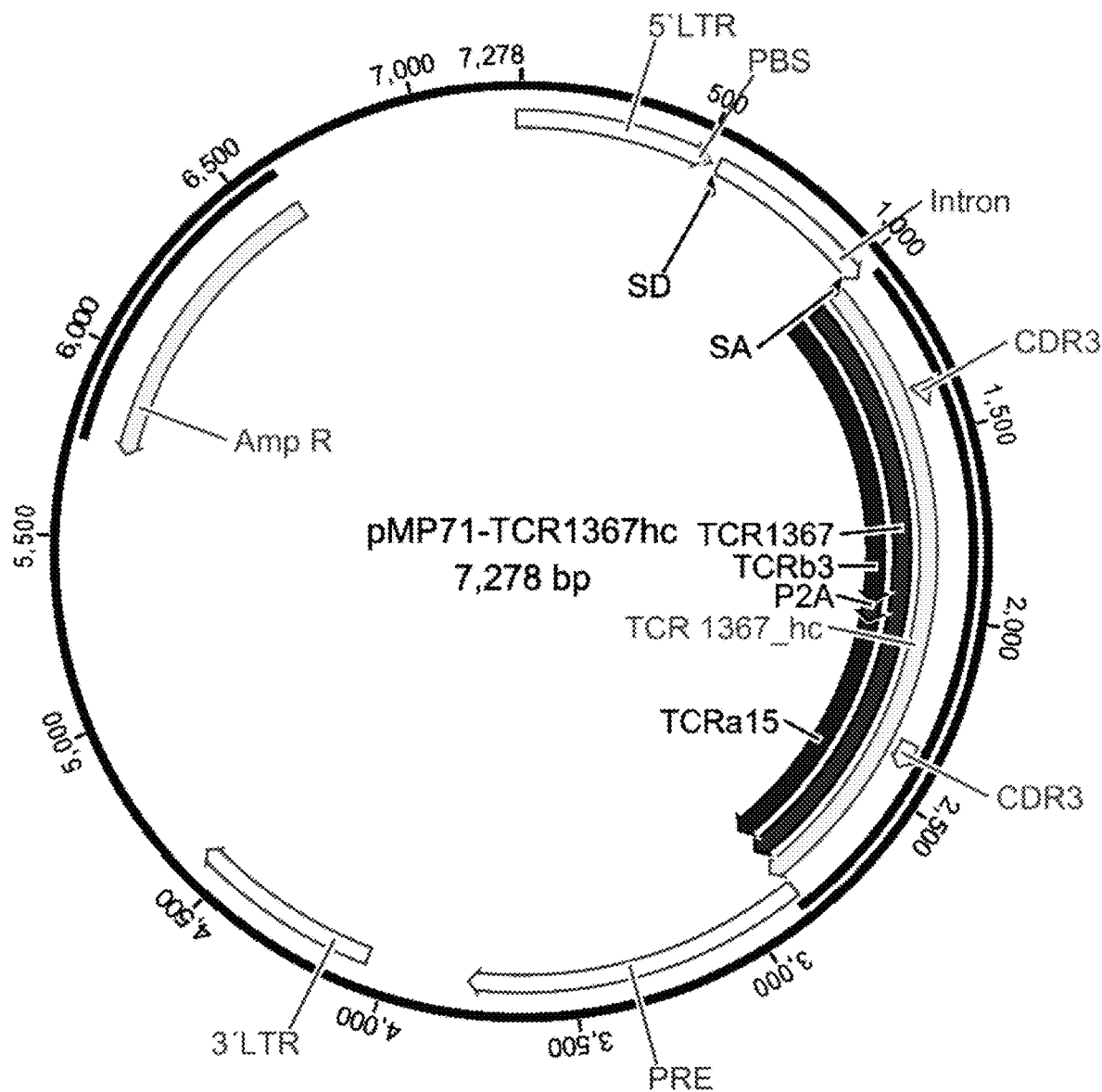
FIG. 8 Vector map of pMP71-TCR1367hc. The TCR encoding sequence is located between nucleotides 1041 and 2864 of SEQ ID NO: 13. The TCR beta chain is located between nucleotides 1041 and 1970, the alpha chain between 2037 and 2864.
Figure 9:
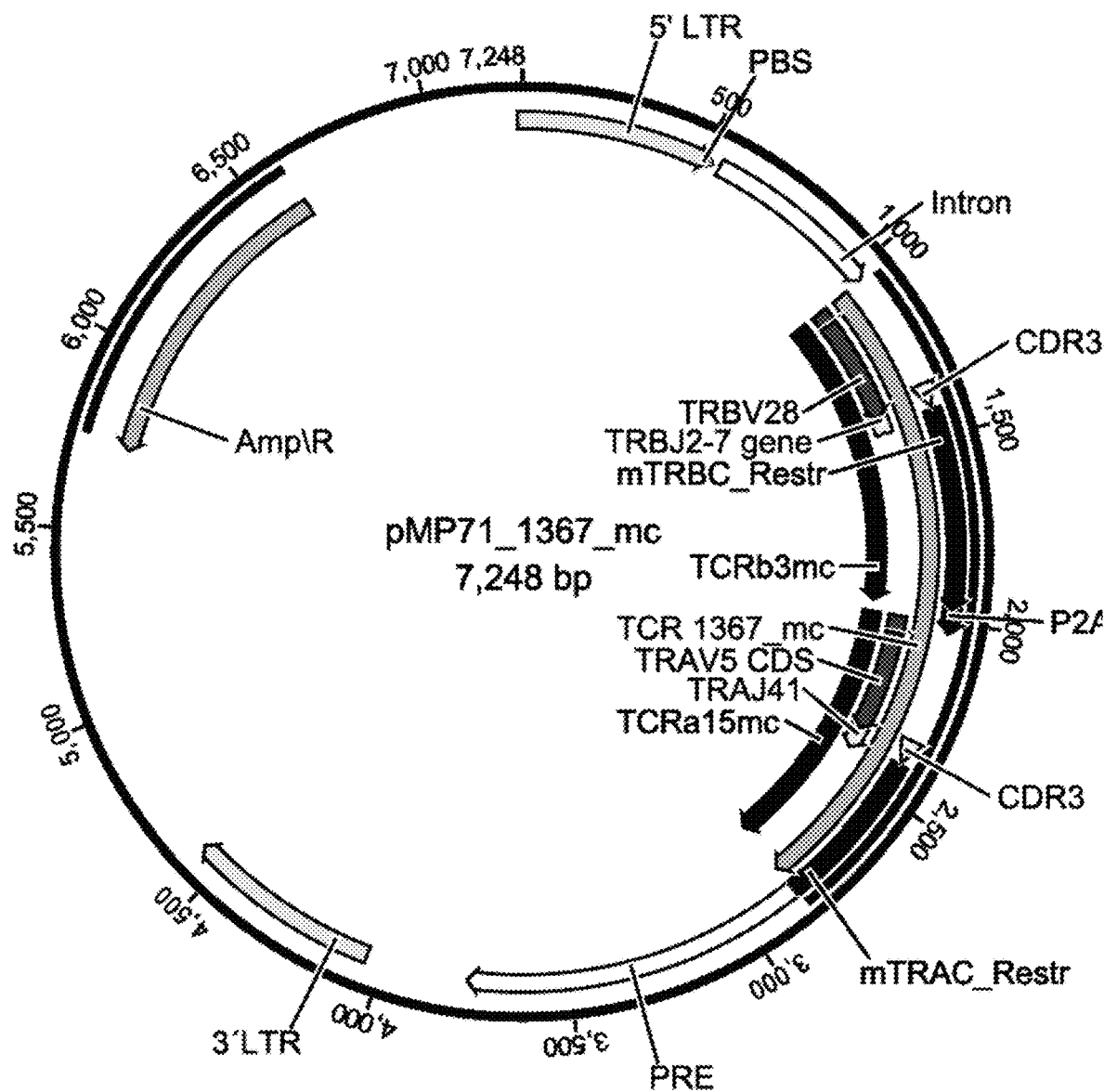
FIG. 9 Vector map of pMP71-TCR1367mc. The TCR encoding sequence is located between nucleotides 1041 and 2834 of SEQ ID NO: 14. The TCR beta chain is located between nucleotides 1041 and 1952, the alpha chain between 2019 and 2834.
Figure 10:
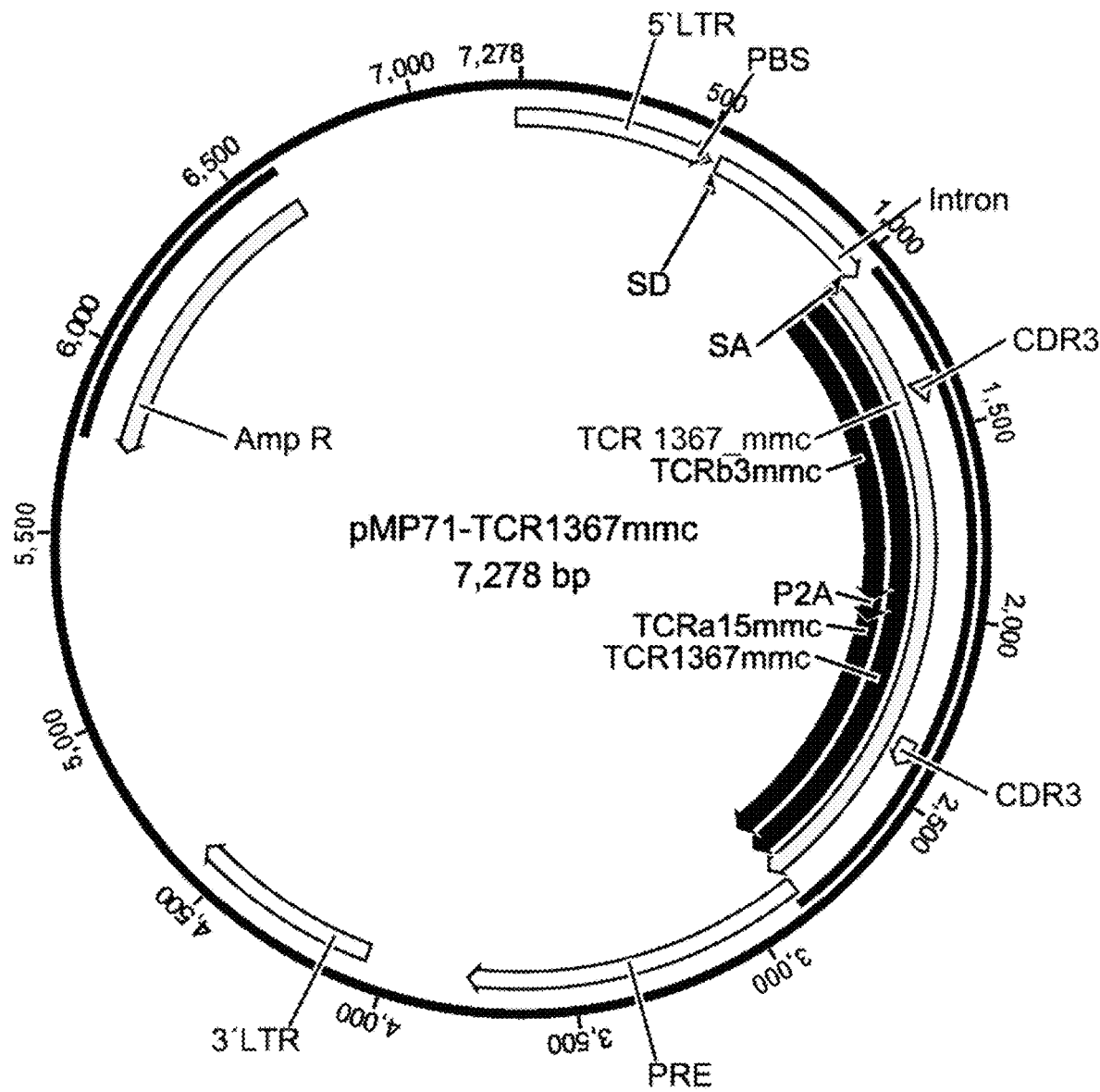
FIG. 10 Vector map of pMP71-TCR1367mmc. The TCR encoding sequence is located between nucleotides 1041 and 2864 of SEQ ID NO: 15. The TCR beta chain is located between nucleotides 1041 and 1970, the alpha chain between 2037 and 2864.
Figure 11:
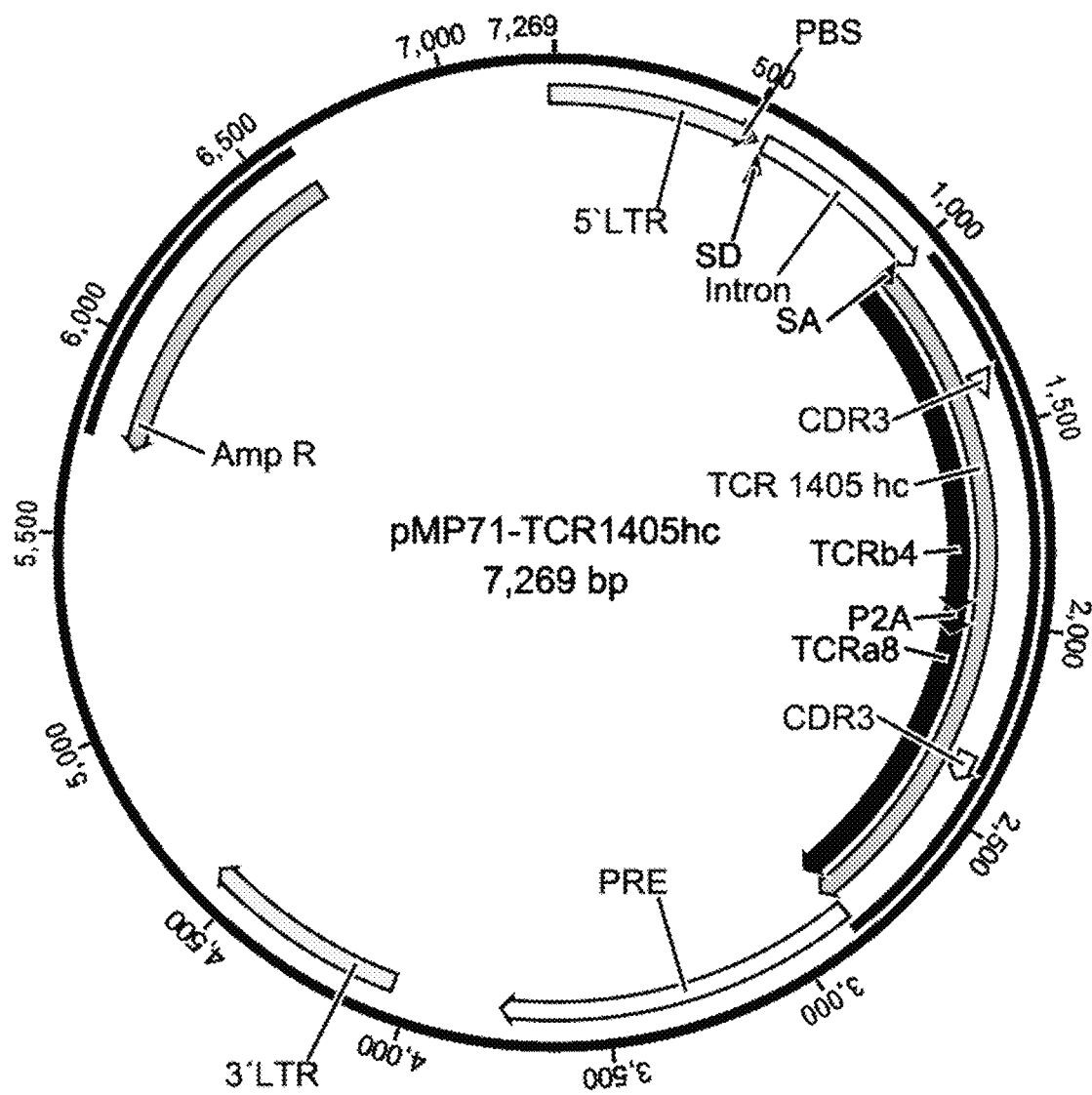
FIG. 11 Vector map of pMP71-TCR1405hc. The TCR encoding sequence is located between nucleotides 1041 and 2855 of SEQ ID NO: 16. The TCR beta chain is located between nucleotides 1041 and 1967, the alpha chain between 2034 and 2855.
Figure 12:
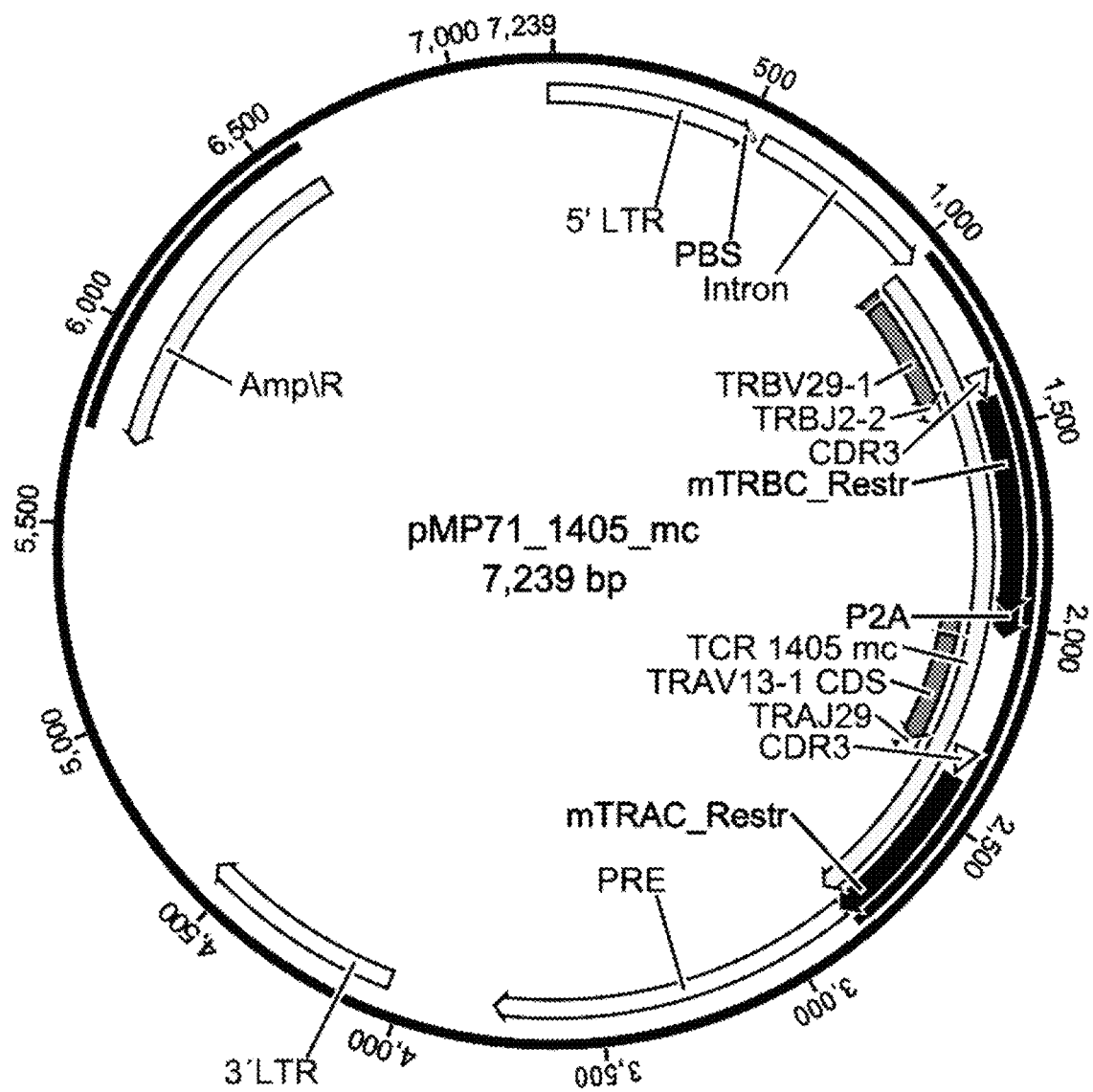
FIG. 12 Vector map of pMP71-TCR1405mc. The TCR encoding sequence is located between nucleotides 1041 and 2825 of SEQ ID NO: 17. The TCR beta chain is located between nucleotides 1041 and 1949, the alpha chain between 2016 and 2825.
Figure 13:
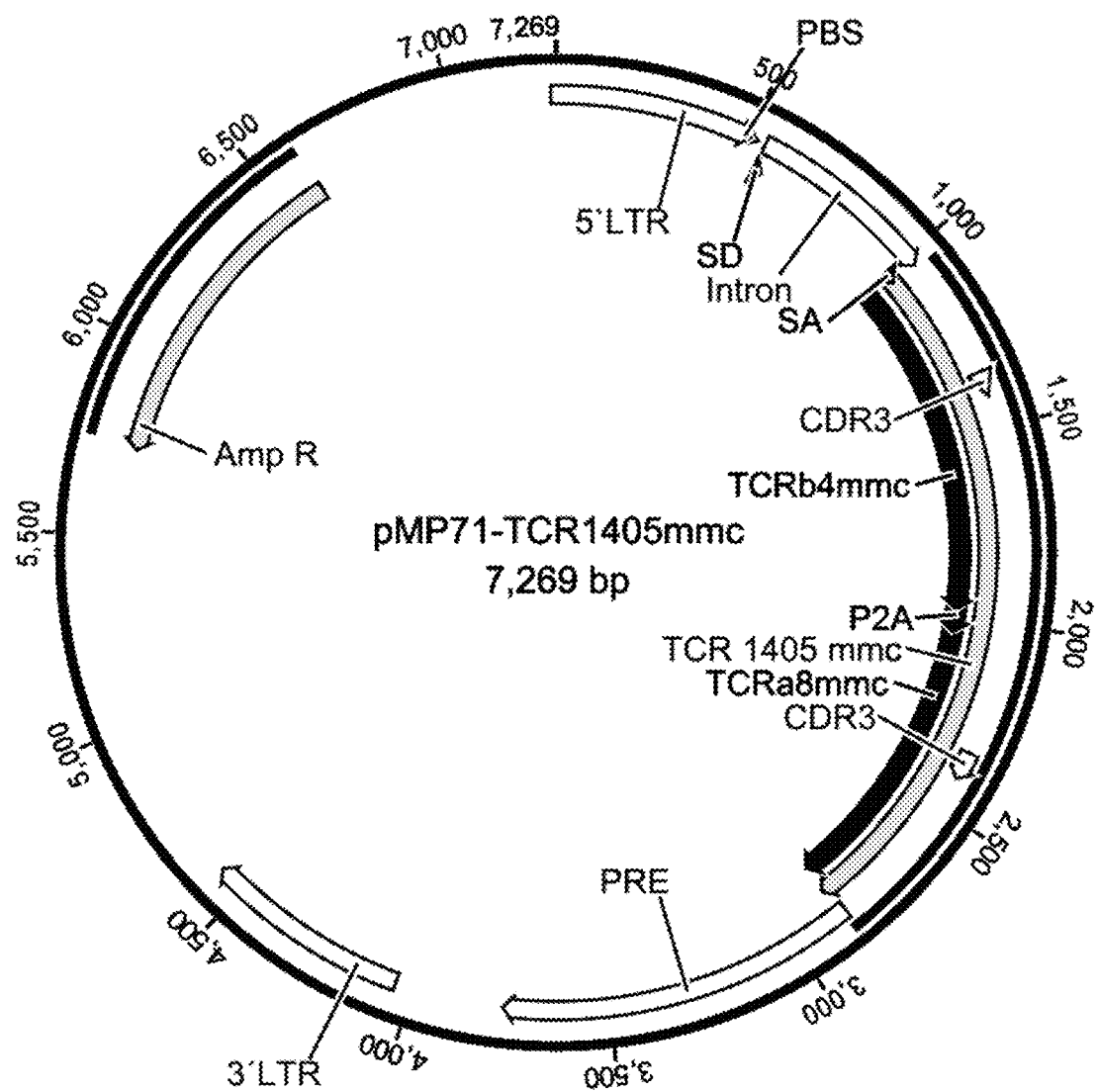
FIG. 13 Vector map of pMP71-TCR1405mmc. The TCR encoding sequence is located between nucleotides 1041 and 2854 of SEQ ID NO: 18. The TCR beta chain is located between nucleotides 1041 and 1967, the alpha chain between 2034 and 2854.
Figure 14:
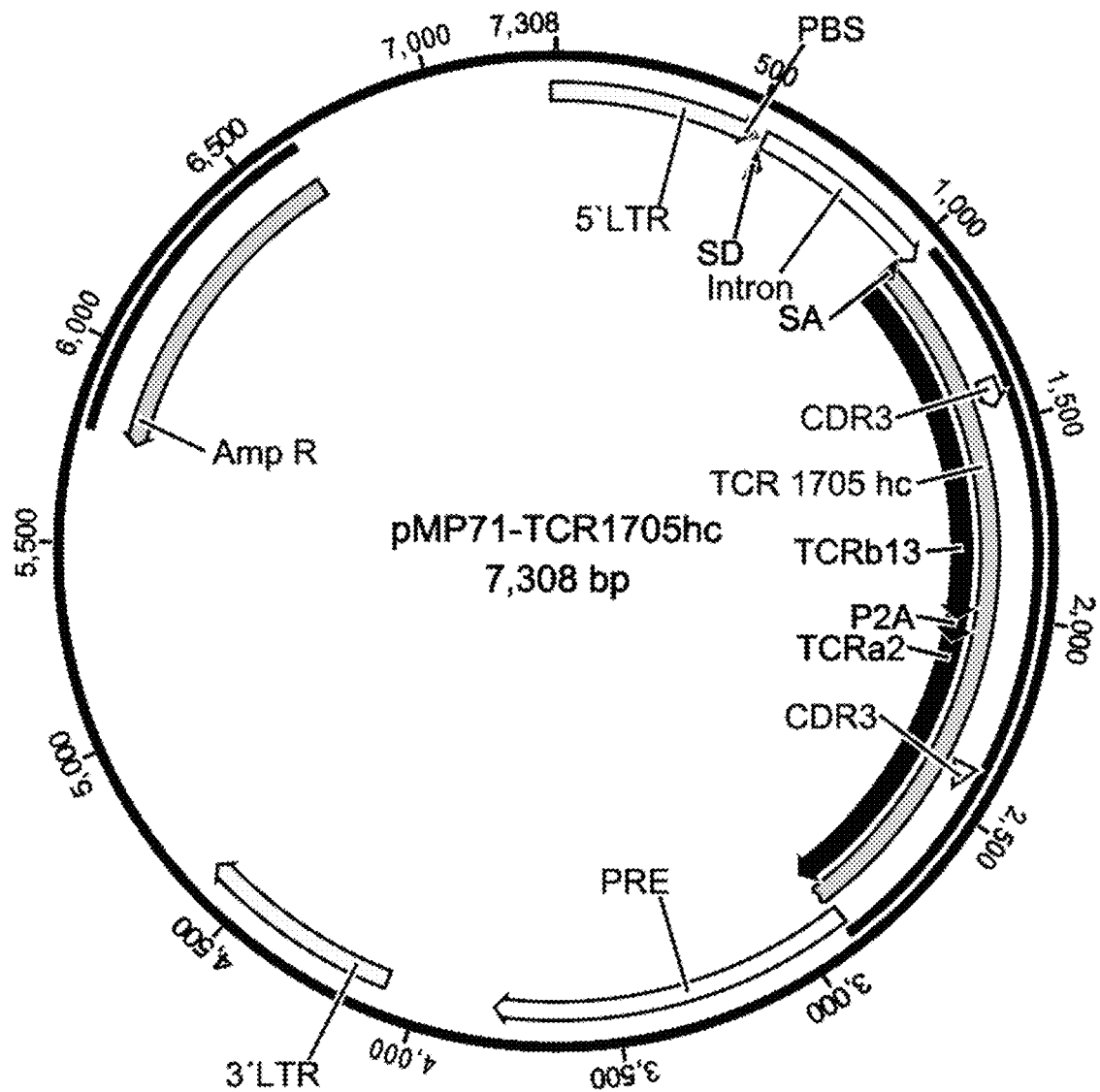
FIG. 14 Vector map of pMP71-TCR1705hc. The TCR encoding sequence is located between nucleotides 1041 and 2894 of SEQ ID NO: 19. The TCR beta chain is located between nucleotides 1041 and 2006, the alpha chain between 2073 and 2894.
Figure 15:
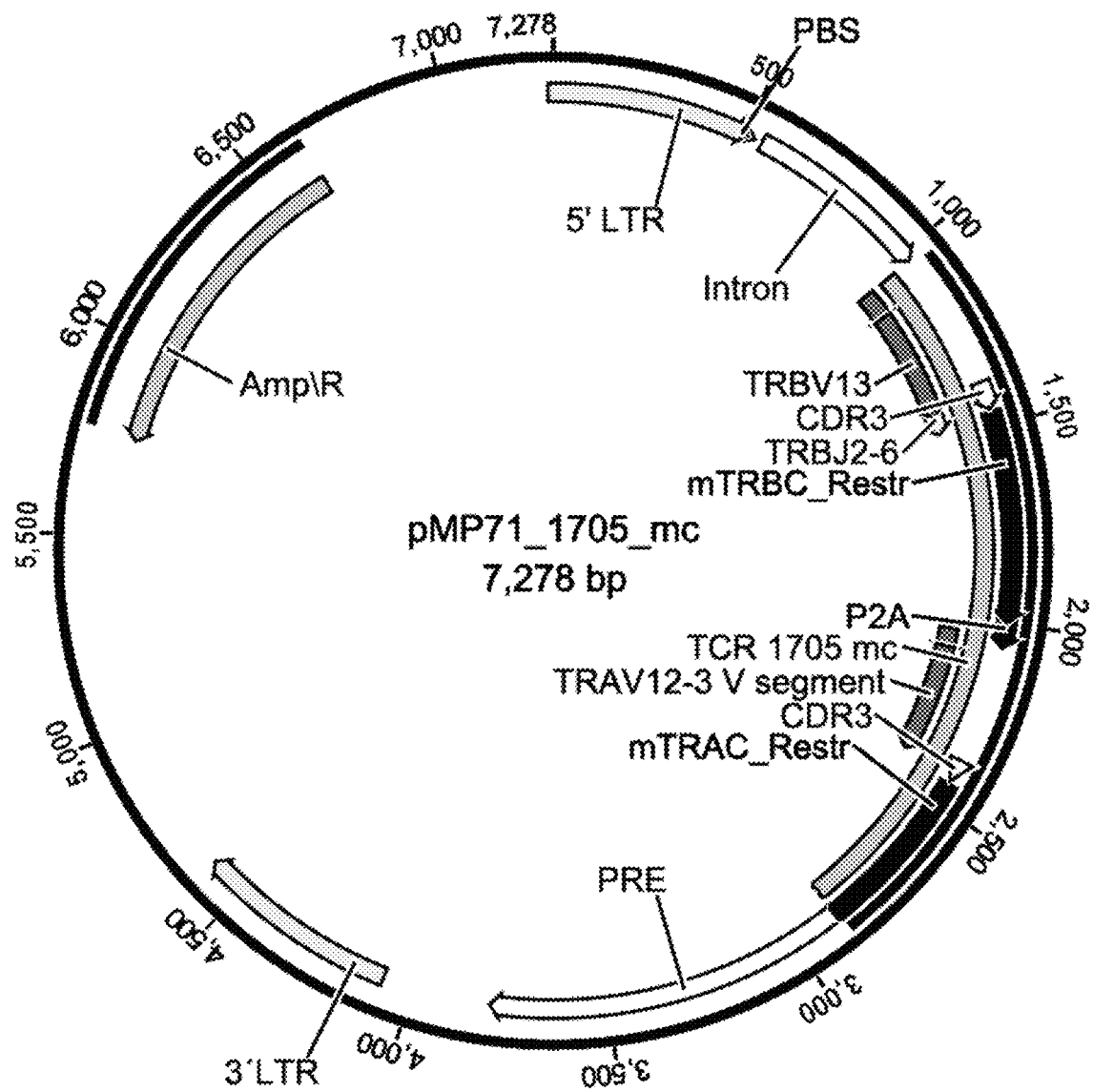
FIG. 15 Vector map of pMP71-TCR1705mc. The TCR encoding sequence is located between nucleotides 1041 and 2864 of SEQ ID NO: 20. The TCR beta chain is located between nucleotides 1041 and 1988, the alpha chain between 2055 and 2864.
Figure 16:
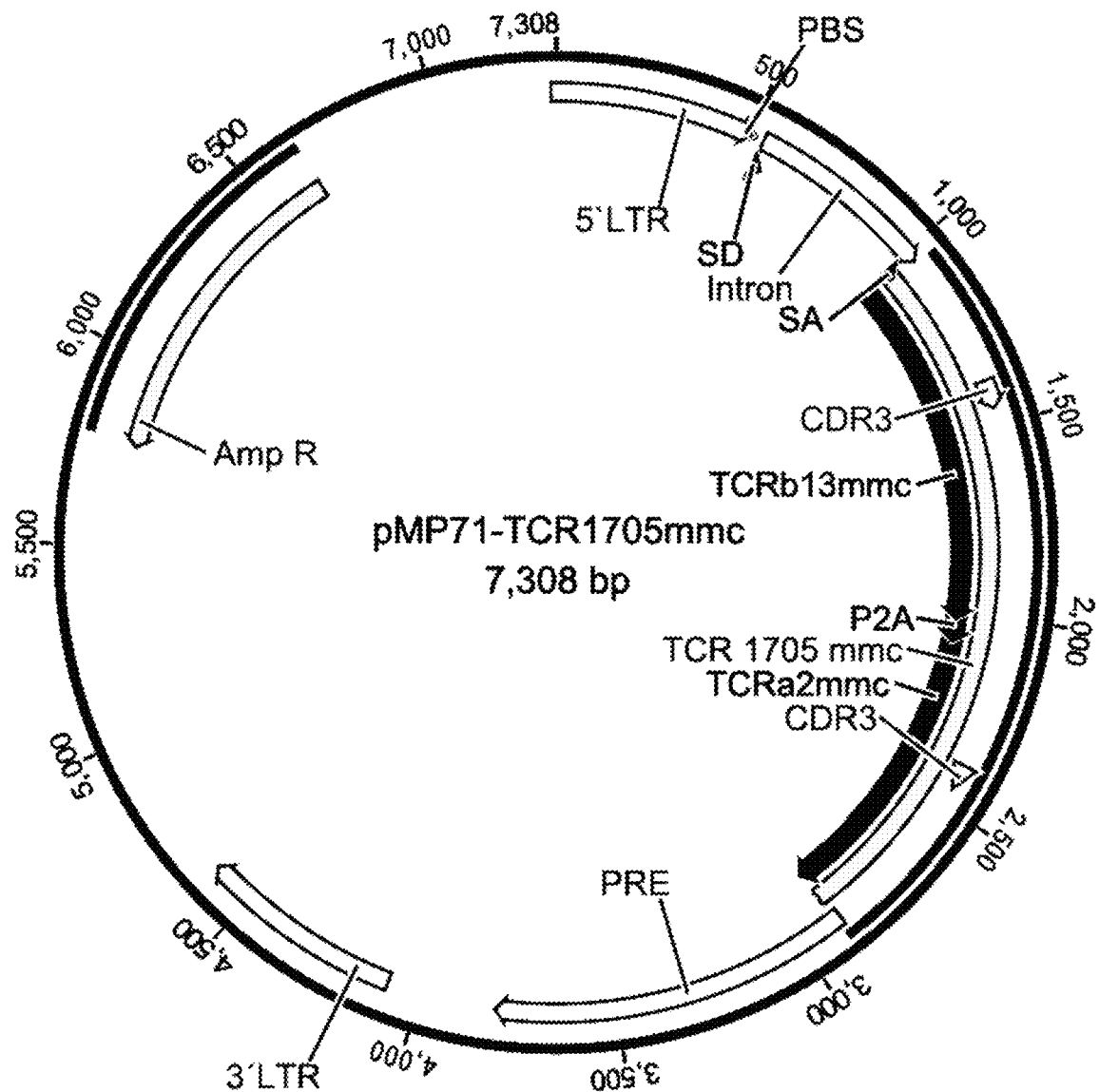
FIG. 16 Vector map of pMP71-TCR1705mmc. The TCR encoding sequence is located between nucleotides 1041 and 2894 of SEQ ID NO: 21. The TCR beta chain is located between nucleotides 1041 and 2006, the alpha chain between 2073 and 2894.

This was further confirmed by testing tumor cell recognition using the TCRs of the invention (FIG. 7). Transduced hBLs were incubated with different tumor cell lines. After overnight incubation IFNγ-production was measured by ELISA. The transduced hPBLs specifically recognize MAGE-A1 in the context of HLA-A2 restricted presentation. PBLs transduced with TCRs from ABabDII mice (full bars) produce higher amounts of IFNγ than those transduced with TCRs from the human repertoire (shaded bars) when incubated with MAGE-A1 expressing tumor cell lines.

Example 3: Sensitivity and Specificity of the TCR of the Invention

Figure 17:
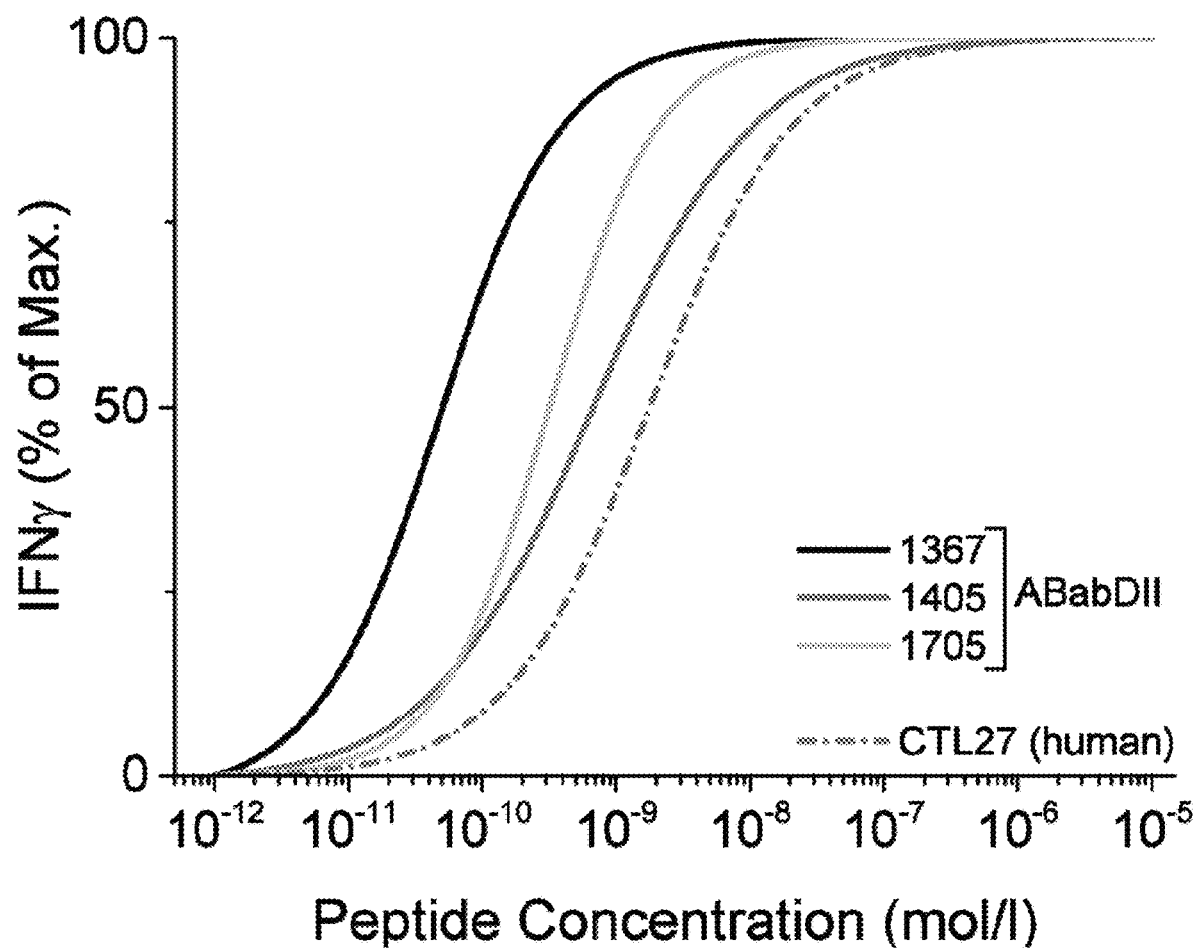
FIG. 17 T2 cells were incubated with increasing concentrations of MAGE-A1278 and cocultured with human T cells that had been transduced with different TCRs as indicated. After 12 hours, functional response was assessed by measuring IFNγ in the cultures.

MAGE-A1$_{278}$ antigen was presented on T2 cells. The antigen presenting T2 cells were co-cultured with T-cells expressing the TCR of the invention or a control TCR (CTL27). As shown in FIG. 17 T cells modified with inventive TCRs from ABabDII mice (solid lines) respond to lower amounts of antigen than those modified with a human TCR (dash-dotted line). (One representative example out of 3 independent experiments is shown). These results indicate the surprisingly improved (by at least one order of magnitude) sensitivity of the TCR of the invention compared to state of the art TCR.

Figure 18:
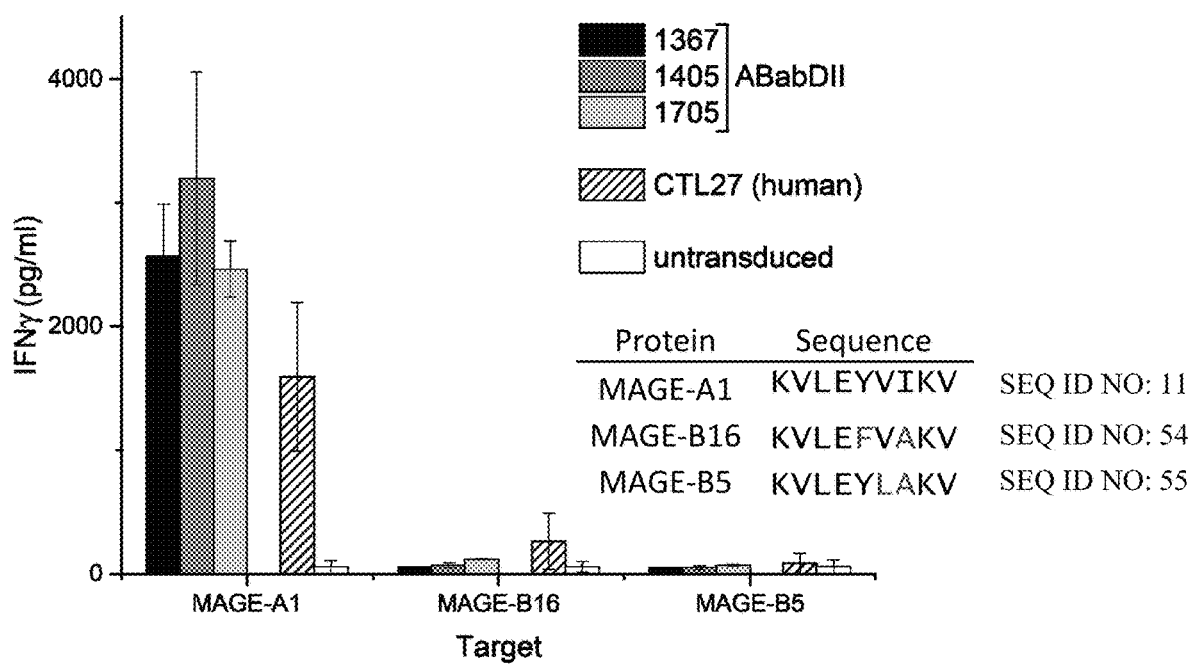
FIG. 18 T2 cells were loaded with 10-5 mol/l MAGE-A1278 (SEQ ID NO: 11) or the 2 most similar epitopes in the human proteome (MAGE-B16 and MAGE-B5, SEQ ID NOs: 54 and 55, respectively) differing in only 2 amino acids from MAGE-A1278 and co-cultured with TCR modified T cells. Functional response was assessed based on IFNγ production.

In order to test the specificity of the TCR of the invention over closely related MAGE antigenic epitopes, the TCRs were brought into contact with the MAGE antigens KVLEFVAKV (MAGE-B16) (SEQ ID NO:54) and KVLEYLAKV (MAGE-B5) (SEQ ID NO:55). The antigens were presented by T2 cells which were then co-cultured with T-cells expressing the TCR of the invention and a control. Interferon-γ release was measured. As can be seen from FIG. 18, the TCR of the invention significantly recognized the MAGE-A1$_{278}$ antigen and not the variants of the epitope. The specificity was much better compared to the control TCR.

Figure 19:
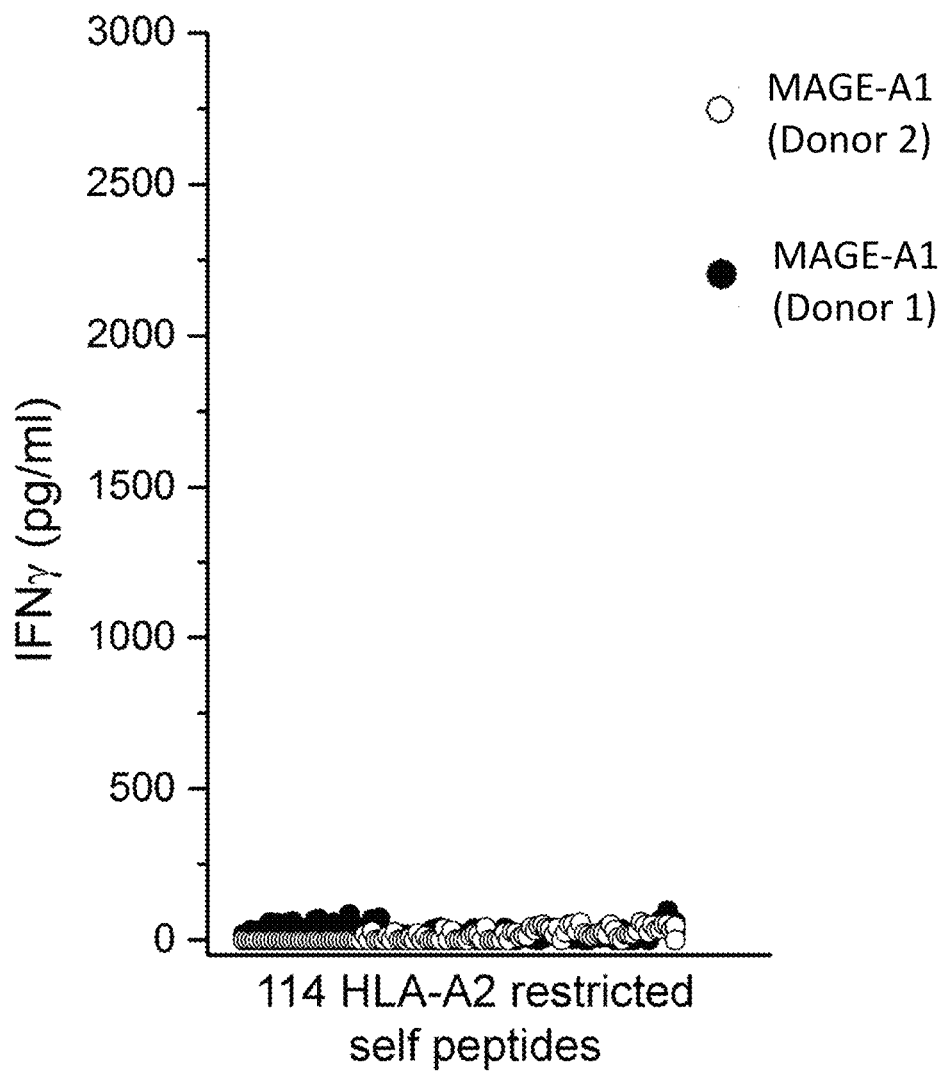
FIG. 19 T2 cells were loaded with one of 114 different HLA-A2 restricted self-peptides at a concentration of 10-5 mol/l and co-cultured with T cells from 2 different donors that were transduced with TCR 1367. The results of donor 1 are shown as black dots, the results of donor 2 by white dots.

The high specificity of the TCR of the invention was confirmed in an experiment testing 144 human HLA-A2 restricted self-antigens. FIG. 19 shows that donor T cells transfected with TCR 1367 specifically detected MAGE-A1 and not any other tested self-antigen, demonstrating the surprisingly high degree of specificity of the TCR of the invention.

Furthermore 10$^6$ murine MAGE-A1 expressing fibrosarcoma cells were injected into immunodeficient mice and grown to a clinically relevant size of approximately 500 mm$^3$ tumor volume. To treat the tumors 10$^6$ MAGE-A1 specific T cells bearing the either one of 2 TCRs from ABabDII mice (1367, 1405) or a human TCR (CTL27) were injected. In the control group, 10$^6$ T cells bearing an irrelevant TCR were injected.

Treatment response was assessed 14 days after T-cell injection based on tumor volume. The results are provided in table 2 below. In the groups treated with ABabDII TCRs 100% and 67% of the animals responded to treatment. On the contrary, none of the animals treated with T cells transduced with a human TCR or an irrelevant TCR responded.

TABLE 2

| Treatment group | Response rate |
|---|---|
| 1367 | 5/5 (100%) |
| 1405 | 4/6 (67%) |
| CTL27 (human) | 0/6 (0%) |
| Irrelevant TCR | 0/3 (0%) |

SEQUENCE LISTING

```
Sequence total quantity: 55
SEQ ID NO: 1                moltype = AA   length = 15
FEATURE                     Location/Qualifiers
REGION                      1..15
                            note = CDR3
source                      1..15
                            mol_type = protein
                            organism = synthetic construct
SEQUENCE: 1
CAESIGSNSG YALNF                                                    15

SEQ ID NO: 2                moltype = AA   length = 14
FEATURE                     Location/Qualifiers
REGION                      1..14
                            note = CDR3
source                      1..14
                            mol_type = protein
                            organism = synthetic construct
SEQUENCE: 2
CAARPNSGNT PLVF                                                     14

SEQ ID NO: 3                moltype = AA   length = 12
FEATURE                     Location/Qualifiers
REGION                      1..12
                            note = CDR3
source                      1..12
                            mol_type = protein
                            organism = synthetic construct
SEQUENCE: 3
CAMSDTGNQF YF                                                       12

SEQ ID NO: 4                moltype = AA   length = 13
FEATURE                     Location/Qualifiers
REGION                      1..13
                            note = CDR3
source                      1..13
                            mol_type = protein
                            organism = synthetic construct
SEQUENCE: 4
CASRGLAGYE QYF                                                      13

SEQ ID NO: 5                moltype = AA   length = 14
FEATURE                     Location/Qualifiers
REGION                      1..14
                            note = CDR3
source                      1..14
                            mol_type = protein
                            organism = synthetic construct
SEQUENCE: 5
CSVEQDTNTG ELFF                                                     14

SEQ ID NO: 6                moltype = AA   length = 15
FEATURE                     Location/Qualifiers
REGION                      1..15
                            note = CDR3
source                      1..15
                            mol_type = protein
                            organism = synthetic construct
SEQUENCE: 6
CASSFRGGGA NVLTF                                                    15

SEQ ID NO: 7                moltype = AA   length = 11
FEATURE                     Location/Qualifiers
source                      1..11
                            mol_type = protein
                            organism = Homo sapiens
SEQUENCE: 7
CAESYNARLM F                                                        11

SEQ ID NO: 8                moltype = AA   length = 13
FEATURE                     Location/Qualifiers
source                      1..13
                            mol_type = protein
                            organism = Homo sapiens
SEQUENCE: 8
CAGSGGGTDK LIF                                                      13

SEQ ID NO: 9                moltype = AA   length = 16
```

```
FEATURE                 Location/Qualifiers
source                  1..16
                        mol_type = protein
                        organism = Homo sapiens
SEQUENCE: 9
CSAREPGQGP YEQYFG                                                       16

SEQ ID NO: 10           moltype = AA  length = 11
FEATURE                 Location/Qualifiers
source                  1..11
                        mol_type = protein
                        organism = Homo sapiens
SEQUENCE: 10
CASLSGVYTF G                                                            11

SEQ ID NO: 11           moltype = AA  length = 9
FEATURE                 Location/Qualifiers
source                  1..9
                        mol_type = protein
                        organism = Homo sapiens
SEQUENCE: 11
KVLEYVIKV                                                                9

SEQ ID NO: 12           moltype = AA  length = 9
FEATURE                 Location/Qualifiers
source                  1..9
                        mol_type = protein
                        organism = Mus musculus
SEQUENCE: 12
KVLQFFASI                                                                9

SEQ ID NO: 13           moltype = DNA  length = 7278
FEATURE                 Location/Qualifiers
misc_feature            1..7278
                        note = pMP71-TCR1367hc
source                  1..7278
                        mol_type = other DNA
                        organism = synthetic construct
SEQUENCE: 13
tcaaggttag gaacagagag acagcagaat atgggccaaa caggatatct gtggtaagca        60
gttcctgccc cggctcaggg ccaagaacag ttgaacagc  agaatatggg ccaaacagga       120
tatctgtggt aagcagttcc tgccccggct cagggccaag aacagatggt ccccagatgc       180
ggtcccgccc tcagcagttt ctagagaacc atcagatgtt tccagggtgc ccaaggacc        240
tgaaatgacc ctgtgcctta tttgaactaa ccaatcagtt cgcttctcgc ttctgttcgc       300
gcgcttctgc tccccgagct caataaaaga gcccacaacc cctcactcgg cgcgccagtc       360
ctccgataga ctgcgtcgcc cgggtacccg tattcccaat aaagcctctt gctgtttgca       420
tccgaatcgt ggactcgctg atccttggga gggtctcatc agattgattg actgcccacc       480
tcggggggtct ttcatttgga ggttccaccg agatttggag accccctgcc agggaccacc     540
gacccccccg ccgggaggta agctggccag cggtcgtttc gtgtctgtct ctgtctttgt       600
gcgtgtttgt gccggcatct aatgtttgcg cctgcgtctg tactagttgg ctaactagat       660
ctgtatctgg cggtcccgcg gaagaactga cgagttcgta ttcccggccg cagccctcg        720
gagacgtccc agcggcctcg ggggcccgtt ttgtggccca ttctgtatca gttaacctac       780
ccgagtcgga ctttttggag ctccgccact gtccgagggg tacgtggctt tgttggggga      840
cgagagacag agacacttcc cgcccccgtc tgaattttg  ctttcggttt tacgccgaaa       900
ccgcgccgcg cgtcttgtct gctgcagcat cgttctgtgt tgtctctgtc tgactgtgtt      960
tctgtatttg tctgaaaatt agctcgacaa agttaagtaa tagtccctct ctccaagctc     1020
acttacaggc ggccgccacc atgggaatca gactgctgtg cagagtggcc ttctgcttcc     1080
tggccgtggg cctggtggac gtgaaagtga cccagagcag cagatacctc gtgaagcgga     1140
ccggcgagaa ggtgttcctg aatgcgtgc  aggacatgga ccacgagaat atgttctggt     1200
acagacagga ccccggcctg ggcctgcggc tgatctactt cagctacgac gtgaagatga     1260
aggaaaaggg cgacatcccc gagggctaca gcgtgtccag agagaagaaa gagcggttca     1320
gcctgatcct ggaaagcgcc agcaccaacc agaccagcat gtacctgtgc gccagcgag     1380
gcctggccgg ctacgagcag tattttggcc ctggcacccg gctgaccgtg accgaggacc     1440
tgaagaacgt gttcccccc  gaggtggccg tgttcgagcc cagcgaggcc gagatcagcc     1500
acacccagaa agcccccctg gtgtgcctgg ccaccggctt ctaccccgac cacgtggagc     1560
tgtcttggtg ggtgaacggc aaagaggtgc acagcggcgt cagcaccgac cccagcccc     1620
tgaaagagca gccccgcctg aacgacagcc ggtactgcct gagcagccgg ctgagagtga    1680
gcgccacctt ctggcagaac cccggaacc  acttccggtg ccaggtgcag ttctacggcc     1740
tgagcgagaa cgacgagtgg acccaggaca gagccaagcc cgtgacccag atcgtgagcg     1800
ccgaggcctg ggcagagcc  gactgcggct tcaccagcga gagctaccag cagggcgtgc     1860
tgtccgccac aatcctgtac gagatcctgc tgggcaaggc caccctgtac gccgtgctgg     1920
tgtccgccct ggtgctgatg gccatggtga gcggaagga  cagccggggc ggcagcggcg     1980
ccaccaactt tagcctgctg aaacaggcg  gcgacgtgga agagaaccct ggccccatga     2040
agacccttcg cggcttcagc ttcctgttcc tgtggctgca gctgagcggg 2100
gcgaggacgt ggaacagagc ctgtttctga gcgtgcgcga gggcgacagc agcgtgatca     2160
attgcaccta caccgacagc tccagcacct acctgtactg gtacaagcag gaacctggcg     2220
ccggactgca gctgctgacc tacatcttca gcaacatgga catgaagcag gaccagagac     2280
tgaccgtgct gctgaacaag aaggacaagc acctgagcct gcggatcgcc gataccaga     2340
caggcgacag cgccatctac ttttgcgccg agagcatcgg cagcaacagc ggctacgccc     2400
```

```
tgaacttcgg caagggcaca agcctgctcg tgacccctca catccagaac cccgaccccg    2460
ccgtgtacca gctgcgggac agcaagagca gcgacaagag cgtgtgcctg ttcaccgact    2520
tcgacagcca gaccaacgtg agccagagca aggactccga cgtgtacatc accgacaaga    2580
ccgtgctgga catgcggagc atggacttca agagcaactc cgccgtggcc tggtccaaca    2640
agagcgactt cgcctgcgcc aacgccttca acaacagcat catccccgag gacacctttt    2700
tccccagccc cgagagcagc tgcgacgtga aactggtgga gaagagcttc gagaccgaca    2760
ccaacctgaa cttccagaac ctgtccgtga tcggcttccg gatcctgctg ctgaaggtgg    2820
ccggcttcaa cctgctgatg accctgcggc tgtggagcag ctgaattcga gcatcttacc    2880
gccattttatt cccatatttg ttctgttttt cttgatttgg gtatacattt aaatgttaat    2940
aaaacaaaat ggtggggcaa tcatttacat tttatgggat atgtaattac tagttcaggt    3000
gtattgccac aagacaaaca tgttaagaaa ctttcccgtt atttacgctc tgttcctgtt    3060
aatcaacctc tggattacaa aatttgtgaa agattgactg atattcttaa ctatgttgct    3120
ccttttacgc tgtgtggata tgctgcttta atgcctctgt atcatgctat tgcttcccgt    3180
acggctttcg ttttctcctc cttgtataaa tcctggttgc tgtctctttta tgaggagttg    3240
tggcccgttg tccgtcaacg tggcgtggtg tgctctgtgt ttgctgacgc aacccccact    3300
ggctggggca ttgccaccac ctgtcaactc ctttctggga cttttcgcttt cccctcccg    3360
atcgccacgg cagaactcat cgccgcctgc cttgcccgct gctggacagg ggctaggttg    3420
ctgggcactg ataattccgt ggtgttgtcg gggaagctga cgtcctttcc atggctgctc    3480
gcctgtgttg ccaactggat cctgcgcggg acgtccttct gctacgtccc ttcggctctc    3540
aatccagcgg acctccctttc ccgaggcctt ctgccggttc tgcggcctct cccgcgtctt    3600
cgctttcggc ctccgacgag tcggatctcc ctttgggccg cctccccgcc tgtttcgcct    3660
cggcgtccgg tccgtgttgc ttggtcgtca cctgtgcaga attgcgaacc atggattcca    3720
ccgtgaactt tgtctcctgg catgcaaatc gtcaacttgg catgccaaga attaattcgg    3780
atccaagctt aggcctgctc gctttcttgc tgtcccattt ctattaaagg ttcctttgtt    3840
ccctaagtcc aactactaaa ctggggggata ttatgaaggg ccttgagcat ctggattctg    3900
cctagcgcta agcttaacac gagccataga tagaataaaa gattttattt agtctccaga    3960
aaaagggggg aatgaaagac cccacctgta ggtttggcaa gctagcttaa gtaacgccat    4020
tttgcaaggc atgaaaaata cataactgag aatagaagg ttcagatcaa ggttaggaac    4080
agagagacag cagaatatgg gccaaacagg atatctgtgg taagcagttc ctgccccggc    4140
tcagggccaa gaacagttgg aacagcagaa tatgggccaa acaggatatc tgtggtaagc    4200
agttcctgcc ccggctcagg gccaagaaca gatggtcccc agatgcggtc ccgccctcag    4260
cagtttctag agaaccatca gatgtttcca gggtgcccca aggacctgaa atgaccctgt    4320
gccttatttg aactaaccaa tcagttcgct ctcgcttct gttcgcgcgc ttctgctccc    4380
cgagctcaat aaaagagccc acaaccctc actcggcgcg ccagtcctcc gatagactgc    4440
gtcgccgggg tacccgtgtt ctcaataaac cctcttgcag ttgcatccga ctcgtggtct    4500
cgctgttcct tgggagggtc tcctctgagt gattgactgc ccactcgggg ggtctttcat    4560
tctcgagcag cttggcgtaa tcatggtcat agctgtttcc tgtgtgaaat tgttatccgc    4620
tcacaattcc acacaacata cgagccgaa gcataaagtg taaagcctgg ggtgcctaat    4680
gagtgagcta actcacatta ttgcgttgc gctcactgcc cgctttccag tcgggaaacc    4740
tgtcgtgcca gctgcattaa tgaatcggcc aacgcgcggg gagaggcggt ttgcgtattg    4800
ggcgctcttc cgcttcctcg ctcactgact cgctgcgctc ggtcgttcgg ctgcggcgag    4860
cggtatcagc tcactcaaag gcggtaatac ggttatccac agaatcaggg gataacgcag    4920
gaaagaacat gtgagcaaaa ggccagcaaa aggccaggaa ccgtaaaaag gccgcgttgc    4980
tggcgttttt ccataggctc cgcccccctg acgagcatca caaaaatcga cgctcaagtc    5040
agaggtggcg aaacccgaca ggactataaa gataccaggc gtttccccct ggaagctccc    5100
tcgtgcgctc tcctgttccg accctgccgc ttaccggata cctgtccgcc tttctccctt    5160
cgggaagcgt ggcgctttct catagctcac gctgtaggta tctcagttcg gtgtaggtcg    5220
ttcgctccaa gctgggctgt gtgcacgaac cccccgttca gcccgaccgc tgcgccttat    5280
ccggtaacta tcgtcttgag tccaacccgg taagacacga cttatcgcca ctggcagcag    5340
ccactggtaa caggattagc agagcgaggt atgtaggcgg tgctacagag ttcttgaagt    5400
ggtggcctaa ctacggctac actagaagaa cagtattttgg tatctgcgct ctgctgaagc    5460
cagttacctt cggaaaaaga gttggtagct cttgatccgg caaacaaacc accgctggta    5520
gcggtggttt ttttgtttgc aagcagcaga ttacgcgcag aaaaaaagga tctcaagaag    5580
atcctttgat cttttctacg ggtctgacgc tcagtggaa cgaaaactca cgttaaggga    5640
ttttgtcat gagattatca aaaaggatct cacctagat cctttttaaat taaaaatgaa    5700
gttttaaatc aatctaaagt atatatgagt aaacttggtc tgacagttac caatgcttaa    5760
tcagtgaggc acctatctca gcgatctgtc tatttcgttc atccatagtt gcctgactcc    5820
ccgtcgtgta gataactacg atacgggagg gcttaccatc tggccccagt gctgcaatga    5880
taccgcgaga cccacgctca ccggctccag atttatcagc aataaaccag ccagccggaa    5940
gggccgagcg cagaagtggt cctgcaactt tatccgcctc catccagtct attaattgtt    6000
gccgggaagc tagagtaagt agttcgccag ttaatagttt cgcaacgtt gttgccattg    6060
ctacaggcat cgtggtgtca cgctcgtcgt ttggtatggc ttcattcagc tccgttccc    6120
aacgatcaag gcgagttaca tgatccccca tgttgtgcaa aaaagcggtt agctccttcg    6180
gtcctccgat cgttgtcaga agtaagttgg ccgcagtgtt atcactcagg ttatggcag    6240
cactgcataa ttctcttact gtcatgccat ccgtaagatg cttttctgtg actggtgagt    6300
actcaaccaa gtcattctga gaatagtgta tgcggcgacc gagttgctct tgcccggcgt    6360
caatacggga taataccgcg ccacatagca gaactttaaa agtgctcatc attggaaaac    6420
gttcttcggg gcgaaaactc tcaaggatct taccgctgtt gagatccagt tcgatgtaac    6480
ccactcgtgc acccaactga tcttcagcat cttttacttt caccagcgtt tctgggtgag    6540
caaaaacagg aaggcaaaat gccgcaaaaa agggaataag ggcgacacgg aaatgttgaa    6600
tactcatact cttccttttt caatattatt gaagcattta tcaggttatt tgtctcatga    6660
gcggatacat atttgaatgt atttagaaaa ataaacaaat aggggttccg cgcacatttc    6720
cccgaaaagt gccacctgac gtctaagaaa ccattattat catgacatta acctataaaa    6780
ataggcgtat cacgaggccc tttcgtctcg cgcgtttcgg tgatgacggt gaaaacctct    6840
gacacatgca gctcccggag acggtcacag cttgtctgta agcggatgcc gggagcagac    6900
aagcccgtca gggcgcgtca gcgggtgttg gcgggtgtcg ggctggctt aactatgcgg    6960
catcagagca gattgtactg agagtgcacc atatgcggtg tgaaataccg cacagatgcg    7020
taaggagaaa ataccgcatc aggcgccatt cgccattcag gctgcgcaac tgttgggaag    7080
ggcgatcggt gcgggcctct tcgctattac gccagctggc gaaaggggga tgtgctgcaa    7140
```

-continued

```
ggcgattaag ttgggtaacg ccagggtttt cccagtcacg acgttgtaaa acgacggcca   7200
gtgaattagt actctagctt aagtaacgcc attttgcaag gcatggaaaa tacataactg   7260
agaatagaga agttcaga                                                 7278

SEQ ID NO: 14           moltype = DNA   length = 7248
FEATURE                 Location/Qualifiers
misc_feature            1..7248
                        note = pMP71_1367_mc
source                  1..7248
                        mol_type = other DNA
                        organism = synthetic construct
SEQUENCE: 14
tcaaggttag gaacagagag acagcagaat atgggccaaa caggatatct gtggtaagca     60
gttcctgccc cggctcaggg ccaagaacag ttggaacagc agaatatggg ccaaacagga    120
tatctgtggt aagcagttcc tgccccggct cagggccaag aacagatggt ccccagatgc    180
ggtcccgccc tcagcagttt ctagagaacc atcagatgtt tccagggtgc cccaaggacc    240
tgaaatgacc ctgtgcccta tttgaactaa ccaatcagtt cgcttctcgc ttctgttcgc    300
gcgcttctgc tcccccgagct caataaaaga gcccacaacc cctcactcgg cgcgccagtc    360
ctccgataga ctgcgtcgcc cgggtacccg tattcccaat aaagcctctt gctgtttgca    420
tccgaatcgt ggactcgctg atccttggga gggtctcctc agattgattg actgcccacc    480
tcgggggtct ttcatttgga ggttccaccg agatttggag accctgccc agggaccacc     540
gacccccccg ccgggaggta agctggccag cggtcgtttc gtgtctgtct ctgtctttgt    600
gcgtgtttgt gccggcatct aatgtttgcg cctgcgtctg tactagttgg ctaactagat    660
ctgtatctgg cggtcccgcg gaagaactga cgagttcgta ttcccggccg cagcccctgg    720
gagacgtccc agcggcctcg ggggcccgtt tgtggccca ttctgtatca gttaacctac      780
ccgagtcgga cttttggag ctccgccact gtccgaggg tacgtggctt tgttggggga      840
cgagagacag agacacttcc cgcccccgtc tgaattttg ctttcggttt tacgccgaaa     900
ccgcgccgcg cgtcttgtct gctgcagcat cgttctgtgt tgtctctgtc tgactgtgtt    960
tctgtatttg tctgaaaatt agctcgacaa agttaagtaa tagtccctct ctccaagctc   1020
acttacaggc ggccgccacc atgggaatca gactgctgta cagtgggctg ttctgcttcc   1080
tggccgtggg cctggtggac gtgaaagtga cccgagagca cagataccta gtgaagcgga   1140
ccggcgagaa ggtgttcctg gaatgcgtgc aggacatgga ccacgagaat atgttctggt   1200
acagacagga ccccggcctg ggcctgcggc tgatctactt cagctacgac gtgaagatga   1260
aggaaaaggg cgacatcccc gagggctaca gcgtgtccag agagaagaaa gagcggttca   1320
gcctgatcct ggaaagcgcc agcaccaacc agaccagcat gtacctgtgc gccagcagag   1380
gcctggccgg ctacgagcag tattttggcc ctggcaccg gctgaccgtg accgaggatc   1440
tgagaaacgt gaccccccc aaggtgtccc tgttcgagcc tagcaaggcc gagatcgcca    1500
acaaacagaa agccaccctc gtgtgcctgg ccagaggctt cttccccgac cacgtggaac    1560
tgtcttggtg ggtcaacggc aaagaggtgc acagcggcgt gtccaccgat cccaggcct     1620
acaaagagag caactacagc tactgcctga gcagcaggct gcgggtgtcc gccaccttct    1680
ggcacaaccc ccggaaccac ttcagatgcc aggtgcagtt tcacgcctg agcgaagagg     1740
acaagtggc cgagggaagc cccaagcccg tgacacagaa tatcagcgcc gaagcctggg    1800
gcagagccga ctgtggaatc gcagcgcca gctatcacca gggcgtgcca gtgccacaa      1860
tcctgtacga gatcctgctg ggcaaggcca ccctgtacgc cgtgctggtg tctggcctgg    1920
tgctgatggc catggtcaag aagaagaaca gcggcagcgg cgccaccaac tttagcctgc   1980
tgaaacaggc cggcgacgtg aagagaaccc tggcccat gaagaccttc gccggcttca     2040
gcttcctgtt cctgtggctg cagctggact gcatggaggc gggcgagagc gtggaacaga    2100
gcctgttct gagcgtgcgc gagggcgaca gcagcgtgat caattgcacc tacaccgaca    2160
gctccagcac ctacctgtac tggtacaagc aggaacctgg cgccgactg cagctgctga    2220
cctacatctt cagcaacatg gacatgaagc aggaccagag actgaccgtg ctgctgaaca    2280
agaaggacaa gcacctgagc ctgcggatcg ccgataccca gacaggcgac agcgccatct    2340
acttttgcgc cgagagcatc ggcagcaaca cgcgctacgc cctgaacttc ggcaagggca    2400
caagcctgct cgtgaccct cacatccaga accctgagcc agccgtgtac cagctgaagg    2460
accccagaag ccaggacagc accctgtgcc tgttcaccga cttcgacagc cagatcaacg    2520
tgcccaagac catggaaagc ggcaccttca tcaccgacaa gcagtgctg gatatgaagg    2580
ccatggacag caagagcaac ggcgccattg cctggtccaa tcagacaagc ttcacatgcc    2640
aggacatctt caaagagaca aacgccacct accccagcag cgacgtgccc tgtgatgcca    2700
ccctgaccga gaagtcctc gagacagaca tgaacctgaa tttccagaac ctgtccgtga    2760
tgggcctgag aatcctgctg ctgaaggtgg ccggcttcaa cctgctgatg acctgagac    2820
tgtggtccag ctgaattcga gcatcttacc gccatttatt cccatatttg ttctgttttt    2880
cttgatttgg gtatacattt aaatgttaat aaaacaaaat ggtgggcaa tcatttacat    2940
tttatgggat atgtaattac tagttcaggt gtattgccac aagacaaaca tgttaagaaa    3000
cttcccgtt atttacgctc tgttcctgtt aatcaacctc tggattacaa atttgtgaa    3060
agattgactg atattcttaa ctatgttgct cctttacgc tgtgtggata tgctgcttta    3120
atgcctctgt atcatgctat tgcttcccgt acgctttcg ttttctcctc cttgtataa    3180
tcctggttgc tgtctcttta tgaggagttg tggcccgttg tccgtcaacg tggcgtggtg    3240
tgctctgtgt ttgctgacgc aaccccccact ggctgggca ttgccaccac ctgtcaactc    3300
cttctctgga ctttcgcttt cccctcccg atcgccacgg cagaactcat cgccgcctgc    3360
cttgcccgct gctggacagg ggctaggttg ctgggcactg gtaattccat ggtgttgtcg    3420
gggaagctga cgtcctttcc atggctgctc gcctgtgttg ccaactggat cctgcgcggg    3480
acgtccttct gctacgtccc ttcggctctc aatccagcgg acctccctc cgaggcctt     3540
ctgccggttc tgcggcctct cccgcgtctt cgctttcggc ctcgacgag tcggatctcc    3600
ctttgggccg cctccccgcc tgtttcgcct cggcgtccgg tccgtgttgc ttggtcgtca    3660
cctgtcgaga attgcgaacc atggattcca ccgtgactt tgtctcctgg catgcaaatt    3720
gtcaacttgg catgccaaga attaattcgg atccaagtt aggcctgctc gctttcttgc    3780
tgtcccattt ctattaaagg ttcctttgtt ccctaagtcc aactactaaa ctggggata     3840
ttatgaaggg ccttgagcat ctggattctg cctagcgcta agcttaacac gagccataga    3900
tagaataaaa gattttattt agtctccaga aaaggggg aatgaaagac cccacctgta     3960
ggtttggcaa gctagcttaa gtaacgccat tttgcaaggc atggaaaata cataactgag    4020
```

-continued

```
aatagagaag ttcagatcaa ggttaggaac agagagacag cagaatatgg gccaaacagg    4080
atatctgtgg taagcagttc ctgccccggc tcagggccaa gaacagttgg aacagcagaa    4140
tatgggccaa acaggatatc tgtggtaagc agttcctgcc ccggctcagg gccaagaaca    4200
gatggtcccc agatgcggtc ccgccctcag cagtttctag agaaccatca gatgtttcca    4260
gggtgcccca aggacctgaa atgaccctgt gccttatttg aactaaccaa tcagttcgct    4320
tctcgcttct gttcgcgcgc ttctgctccc cgagctcaat aaaagagccc acaacccctc    4380
actcggcgcg ccagtcctcc gatagactgc gtcgcccggg tacccgtgtt ctcaataaac    4440
cctcttgcag ttgcatccga ctcgtggtct cgctgttcct tgggagggtc tcctctgagt    4500
gattgactgc ccacctcggg ggtctttcat tctcgagcag cttggcgtaa tcatggtcat    4560
agctgtttcc tgtgtgaaat tgttatccgc tcacaattcc acacaacata cgagccggaa    4620
gcataaagtg taaagcctgg ggtgcctaat gagtgagcta actcacatta attgcgttgc    4680
gctcactgcc cgctttccag tcgggaaacc tgtcgtgcca gctgcattaa tgaatcggcc    4740
aacgcgcggg gagaggcggt ttgcgtattg ggcgctcttc cgcttcctcg ctcactgact    4800
cgctgcgctc ggtcgttcgg ctgcggcgag cggtatcagc tcactcaaag gcggtaatac    4860
ggttatccac agaatcaggg gataacgcag gaaagaacat gtgagcaaaa ggccagcaaa    4920
aggccaggaa ccgtaaaaag gccgcgttgc tggcgttttt ccataggctc cgcccccctg    4980
acgagcatca caaaaatcga cgctcaagtc agaggtggcg aaacccgaca ggactataaa    5040
gataccaggc gtttccccct ggaagctccc tcgtgcgctc tcctgttccg accctgccgc    5100
ttaccggata cctgtccgcc tttctccctt cgggaagcgt ggcgctttct catagctcac    5160
gctgtaggta tctcagttcg gtgtaggtcg ttcgctccaa gctgggctgt gtgcacgaac    5220
ccccccgttca gcccgaccgc tgcgccttat ccggtaacta tcgtcttgag tccaacccgg    5280
taagacacga cttatcgcca ctggcagcag ccactggtaa caggattagc agagcgaggt    5340
atgtaggcgg tgctacagag ttcttgaagt ggtggcctaa ctacggctac actagaagaa    5400
cagtatttgg tatctgcgct ctgctgaagc cagttacctt cggaaaaaga gttggtagct    5460
cttgatccgg caaacaaacc accgctgtag cggtggtttt tttgtttgc aagcagcaga    5520
ttacgcgcag aaaaaaagga tctcaagaag atcctttgat cttttctacg gggtctgacg    5580
ctcagtggaa cgaaaactca cgttaaggga ttttggtcat gagattatca aaaaggatct    5640
tcacctagat ccttttaaat taaaaatgaa gttttaaatc aatctaaagt atatatgagt    5700
aaacttggtc tgacagttac caatgcttaa tcagtgaggc acctatctca gcgatctgtc    5760
tatttcgttc atccatagtt gcctgactcc ccgtcgtgta gataactacg atacgggagg    5820
gcttaccatc tggccccagt gctgcaatga taccgcgaga cccacgctca ccggctccag    5880
atttatcagc aataaaccag ccagccggaa gggccgagcg cagaagtggt cctgcaactt    5940
tatccgcctc catccagtct attaattgtt gccgggaagc tagagtaagt agttcgccag    6000
ttaatagttt gcgcaacgtt gttgccattg ctacaggcat cgtggtgtca cgctcgtcgt    6060
ttggtatggc ttcattcagc tccggttccc aacgatcaag gcgagttaca tgatccccca    6120
tgttgtgcaa aaaagcggtt agctccttcg gtcctccgat cgttgtcaga agtaagttgg    6180
ccgcagtgtt atcactcatg gttatggcag cactgcataa ttctcttact gtcatgccat    6240
ccgtaagatg cttttctgtg actggtgagt actcaaccaa gtcattctga atagtgta    6300
tgcggcgacc gagttgctct tgcccggcgt caatacggga taataccgcg ccacatagca    6360
gaactttaaa agtgctcatc attggaaaac gttcttcggg gcgaaaactc tcaaggatct    6420
taccgctgtt gagatccagt tcgatgtaac ccactcgtgc acccaactga tcttcagcat    6480
cttttacttt caccagcgtt tctgggtgag caaaaacagg aaggcaaaat gccgcaaaaa    6540
agggaataag ggcgacacgg aaatgttgaa tactcatact cttcctttt caatattatt    6600
gaagcattta tcagggttat tgtctcatga gcggatacat atttgaatgt atttagaaaa    6660
ataaacaaat agggggttccg cgcacatttc cccgaaaagt gccacctgac gtctaagaaa    6720
ccattattat catgacatta acctataaaa ataggcgtat cacgaggccc tttcgtctcg    6780
cgcgtttcgg tgatgacggt gaaaacctct gacacatgca gctcccggag acggtcacag    6840
cttgtctgta agcggatgcc gggagcagac aagcccgtca gggcgcgtca gcgggtgttg    6900
gcgggtgtcg ggctggctt aactatgcgg catcagagca gattgtactg agagtgcacc    6960
atatgcggtg tgaaataccg cacagatgcg taaggagaaa ataccgcatc aggcgccatt    7020
cgccattcag gctgcgcaac tgttgggaag ggcgatcggt gcgggcctct tcgctattac    7080
gccagctggc gaaaggggga tgtgctgcaa ggcgattaag ttgggtaacg ccagggtttt    7140
cccagtcacg acgttgtaaa acgacggcca gtgaattagt actctagctt aagtaacgcc    7200
attttgcaag gcatggaaaa tacataactg agaatagaga agttcaga              7248
```

| SEQ ID NO: 15 | moltype = DNA length = 7278 |
|---|---|
| FEATURE | Location/Qualifiers |
| misc_feature | 1..7278 |
| | note = pMP71-TCR1367mmc |
| source | 1..7278 |
| | mol_type = other DNA |
| | organism = synthetic construct |

SEQUENCE: 15
```
tcaaggttag gaacagagag acagcagaat atgggccaaa caggatatct gtggtaagca     60
gttcctgccc cggctcaggg ccaagaacag ttggaacagc agaatatggg ccaaacagga    120
tatctgtggt aagcagttcc tgccccggct cagggccaag aacagatggt ccccagatgc    180
ggtcccgccc tcagcagttt ctagagaacc atcagatgtt tccagggtgc ccaaggacc    240
tgaaatgacc ctgtgcctta tttgaactaa ccaatcagtt cgcttctcgc ttctgttcgc    300
gcgcttctgc tccccgagct caataaaaga gcccacaagt cctcactcgc gcgccagtc    360
ctccgataga ctgcgtcgcc cgggtacccg tattcccaat aaagcctctt gctgtttca    420
tccgaatcgt ggactcgctg atccttggga ggtctcctc agattgattg actgcccacc    480
tcgggggtct tcatttgga ggttccaccg agatttggag accctgccc agggaccacc    540
gacccccccg ccgggaggta agctggccag cggtcgtttc gtgtctgtct ctgtctttgt    600
gcgtgtttgt gccggcatct aatgtttgcg cctgcgtctg tactagttgg ctaactagat    660
ctgtatctgg cggtcccgcg gaagaactga cgagttcgta ttcccggccg cagccctgg    720
gagacgtccc agcggcctcg ggggcccgtt ttgtggccca ttctgtatca gttaacctac    780
ccgagtcgga cttttggag ctcgccact gtccgagggg tacgtggctt tgttggggga    840
cgagagacag agacacttcc cgccccgtc tgaattttgt ctttcggttt tacgccgaaa    900
ccgcgccgcg cgtcttgtct gctgcagcat cgttctgtgt tgtctctgtc tgactgtgtt    960
```

```
tctgtatttg tctgaaaatt agctcgacaa agttaagtaa tagtccctct ctccaagctc  1020
acttacaggc ggccgccacc atgggaatca gactgctgtg cagagtggcc ttctgcttcc  1080
tggccgtggg cctggtggac gtgaaagtga cccagagcag cagataccte gtgaagcgga  1140
ccggcgagaa ggtgttcctg gaatgcgtgc aggacatgga ccacgagaat atgttctggt  1200
acagacagga ccccggcctg ggcctgcggc tgatctactt cagctacgac gtgaagatga  1260
aggaaaaggg cgacatcccc gagggctaca gcgtgtccag agagaagaaa gagcggttca  1320
gcctgatcct ggaaagcgcc agcaccaacc agaccagcat gtacctgtgc gccagcagag  1380
gcctggccgc ctacgagcag tattttggcc ctggcacccg gctgaccgtg accgaggacc  1440
tgaagaacgt gttcccccc gaggtggccg tgttcgagcc cagcaaggcc gagatcgcca  1500
acacccagaa agccaccctg gtgtgcctgg ccaccggctt ctaccccgac cacgtggaac  1560
tgtcttggtg ggtgaacggc aaagaggtgc acagcggcgt gtgtaccgac ccccagcccc  1620
tgaaagagca gcctgccctg aacgactccc ggtactgcct gagcagccgg ctgagagtgt  1680
ccgccacctt ctggcagaac ccccggaacc acttcagatg ccaggtgcag ttctacggcc  1740
tgagcgagaa cgacgagtgg acccaggacc gggccaacgc cgtgacccag attgtgtctg  1800
ccgaggcctg gggcagagct gattgtggca tcaccagcgc cagctaccac cagggcgtgc  1860
tgagcgccac catcctgtac gagatcctgc tgggcaaggc caccctgtac gccgtgctgg  1920
tgtccgccct ggtgctgatg gccatggtga acggaagga cagcagaggc ggcagcggcg  1980
ccaccaactt tagcctgctg aaacaggccg gcgacgtgga agagaaccct ggccccatga  2040
agaccttcgc cggcttcagc ttcctgttcc tgtggctgca gctggactgc atgagcaggg  2100
gcgaggacgt ggaacagagc ctgtttctga gcgtgcgcga gggcgacagc agcgtgatca  2160
attgcaccta caccgacagc tccagcaccct acctgtactg gtacaagcag gaacctggcg  2220
ccggactgca gctgctgacc tacatcttca gcaacatgga catgaagcag gaccagagac  2280
tgaccgtgct gctgaacaag aaggacaagc acctgagcct gcggatcgcc gatacccaga  2340
caggcgacag cgccatctac ttttgcgccg agagcatcgg cagcaacagc ggctacgccc  2400
tgaacttcgc caagggcaca agcctgctcg tgacccctca catccagaac cccgaccccg  2460
ccgtgtacca gctgcgggac agcaagagca gcgacaagag cgtgtgcctg ttcaccgact  2520
tcgacagcca gaccaacgtg tcccagagca aggacagcga cgtgtacatc accgacaagt  2580
gcgtgctgga catgcggagc atggacttca gagcaactc cgccgtggcc tggtccaaca  2640
agagcgactt cgcctgcgcc aacgccttca acaacagcat catccccgag gacacattct  2700
tccccagctc cgacgtgccc tgcgacgtga agctggtgga aaagagcttc gagacagaca  2760
ccaacctgaa cttccagaac ctgagcgtga tcggcttccg gatcctgctg ctgaaggtgg  2820
ctggcttcaa cctgctgatg acccgcggc tgtggagcag ctgaattcga gcatcttacc  2880
gccatttatt cccatatttg ttctgttttt cttgatttgg gtatacattt aaatgttaat  2940
aaaacaaaat ggtgggcaa tcatttacat tttatgggat atgtaattac tagttcaggt  3000
gtattgccac aagacaaaca tgttaagaaa ctttcccgtt atttacgctc tgttcctgtt  3060
aatcaacctc tggattacaa aatttgtgaa agattgactg atattcttaa ctatgttgct  3120
ccttttacgc tgtgtggata tgctgcttta atgcctctgt atcatgctat tgcttcccgt  3180
acggctttgt ttttctcctc cttgtataaa tcctggttgc tgtctcttta tgaggagttg  3240
tggcccgttg tccgtcaacg tggcgtggtg tgctctgtga ttgctgacgc aacccccact  3300
ggctggggca ttgccaccac ctgtcaactc ctttctggga cttttgcttt cccctcccg  3360
atcgccacgg cagaactcat cgccgcctgc cttgcccgct gctggacagg gctaggttg  3420
ctgggcactg ataattccgt ggtgttgtcg ggaagctgac gtccttttcc atggctgctc  3480
gcctgtgttg ccaactggat cctgcgcggg acgtccttct gctacgtccc ttcggctctc  3540
aatccagcgg acctcccttc ccgaggcctt ctgccggttc tgcggcctct cccgcgtctt  3600
cgctttcggc ctccgacgag tcggatctcc ctttgggccg cctccccgcc tgtttcgcct  3660
cggcgtccgg tccgtgttgc ttggtcgtca cctgtgcaga attgcgaacc atggattcca  3720
ccgtgaactt tgtctcctgg catgcaaatc gtcaacttgg catgccaaga attaattcgg  3780
atccaagctt aggcctgctc gctttcttgc tgtcccattt ctattaaagg ttccttttgtt  3840
ccctaagtcc aactactaaa ctgggggata ttatgaaggg ccttgagcat ctggattctg  3900
cctagcgcta agcttaacac gagccataga tagaataaaa gatttatttt agtctccaga  3960
aaaagggggg aatgaaagac cccacctgta ggtttggcaa gctagcttaa gtaacgccat  4020
tttgcaaggc atgaaaaata cataactgag aatagagaag ttcagatcaa ggttaggaac  4080
agagagacag cagaatatgg gccaaacagg atatctgtgg taagcagttc ctgccccggc  4140
tcagggccaa gaacagttgg aacagcagaa tatgggccaa acaggatatc tgtgtaagc  4200
agttcctgcc ccggctcagg gccaagaaca ggtgtcccc agatgcggtc ccgccctcag  4260
cagtttctag agaaccatca gatgtttcca gggtgcccca aggacctgaa atgaccctgt  4320
gccttatttg aactaaccaa tcagttcgct tctcgcttct gttcgcgcgc ttctgctccc  4380
cgagctcaat aaaagagccc acaacccctc actcggcgcg ccagtcctcc gatagactgc  4440
gtcgcccggg tacccgtgtt ctcaataaac cctcttgcag ttgcatccga ctcgtggtct  4500
cgctgttcct gggagggtc tcctctgagt gattgactgc ccacctcggg ggtctttcat  4560
tctcgagcag cttggcgtaa tcatggtcat agctgtttcc tgtgtgaaat tgttatccgc  4620
tcacaattcc acacaacata cgagccgaa gcataaagtg taaagcctgg ggtgcctaat  4680
gagtgagcta actcacatta attgcgttgc gctcactgcc cgctttccag tcgggaaacc  4740
tgtcgtgcca gctgcattaa tgaatcggcc aacgcgcgga gaggcggtt ttgcgtattg  4800
ggcgctcttc cgcttcctcg ctcactgact cgctgcgctc ggtcgttcgg ctgcggcgag  4860
cggtatcagc tcactcaaag gcggtaatac ggttatccac agaatcaggg gataacgcag  4920
gaaagaacat gtgagcaaaa ggccagcaaa aggccaggaa ccgtaaaaag gccgcgttgc  4980
tggcgttttt ccataggctc cgcccccctg acgagcatca caaaaatcga cgctcaagtc  5040
agaggtggcg aaacccgaca ggactataaa gataccaggc gtttccccct ggaagctccc  5100
tcgtgcgctc tcctgttccg accctgccgc ttaccggata cctgtccgcc tttctccctt  5160
cgggaagcgt ggcgctttct catagctcac gctgtaggta tctcagttcg gtgtaggtcg  5220
ttcgctccaa gctgggctgt gtgcacgaac cccccgttca gcccgaccgc tgcgccttat  5280
ccggtaacta tcgtcttgag tccaacccgg taagacacga cttatcgcca ctggcagcag  5340
ccactggtaa caggattagc agagcgaggt atgtaggcgg tgctacagag ttcttgaagt  5400
ggtggcctaa ctacggctac actagaagaa cagtatttgg tatctgcgct ctgctgaagc  5460
cagttacctt cggaaaaaga gttggtagct cttgatccgg caaacaaacc accgctggta  5520
gcggtggttt ttttgtttgc aagcagcaga ttacgcgcag aaaaaaagga tctcaagaag  5580
atcctttgat cttttctacg gggtctgacg ctcagtggaa cgaaaactca cgttaaggga  5640
ttttggtcat gagattatca aaaaggatct tcacctagat ccttttaaat taaaaatgaa  5700
```

```
gttttaaatc aatctaaagt atatatgagt aaacttggtc tgacagttac caatgcttaa  5760
tcagtgaggc acctatctca gcgatctgtc tatttcgttc atccatagtt gcctgactcc  5820
ccgtcgtgta gataactacg atacgggagg gcttaccatc tggccccagt gctgcaatga  5880
taccgcgaga cccacgctca ccggctccag atttatcagc aataaaccag ccagccggaa  5940
gggccgagcg cagaagtggt cctgcaactt tatccgcctc catccagtct attaattgtt  6000
gccgggaagc tagagtaagt agttcgccag ttaatagttt cgcaacgtt gttgccattg  6060
ctacaggcat cgtggtgtca cgctcgtcgt ttggtatggc ttcattcagc tccggttccc  6120
aacgatcaag gcgagttaca tgatccccca tgttgtgcaa aaaagcggtt agctccttcg  6180
gtcctccgat cgttgtcaga agtaagttgg ccgcagtgtt atcactcatg gttatggcag  6240
cactgcataa ttctcttact gtcatgccat ccgtaagatg cttttctgtg actggtgagt  6300
actcaaccaa gtcattctga gaatagtgta tgcggcgacc gagttgctct tgcccggcgt  6360
caatacggga taataccgcg ccacatagca gaactttaaa agtgctcatc attggaaaac  6420
gttcttcggg gcgaaaactc tcaaggatct taccgctgtt gagatccagt tcgatgtaac  6480
ccactcgtgc acccaactga tcttcagcat cttttacttt caccagcgtt tctgggtgag  6540
caaaaacagg aaggcaaaat gccgcaaaaa agggaataag ggcgacacgg aaatgttgaa  6600
tactcatact cttcctttt caatattatt gaagcattta tcagggttat tgtctcatga  6660
gcggatacat atttgaatgt atttagaaaa ataaacaaat aggggttccg cgcacatttc  6720
cccgaaaagt gccacctgac gtctaagaaa ccattattat catgacatta acctataaaa  6780
ataggcgtat cacgaggccc tttcgtctcg cgcgtttcgg tgatgacggt gaaaacctct  6840
gacacatgca gctcccggag acggtcacag cttgtctgta gcggatgcc gggagcagac  6900
aagcccgtca gggcgcgtca gcgggtgttg gcgggtgtcg ggctggctt aactatgcgg  6960
catcagagca gattgtactg agagtgcacc atatgcggtg tgaaataccg cacagatgcg  7020
taaggagaaa ataccgcatc aggcgccatt cgccattcag gctgcgcaac tgttgggaag  7080
ggcgatcggt gcgggcctct tcgctattac gccagctggc gaaagggga tgtgctgcaa  7140
ggcgattaag ttgggtaacg ccagggtttt cccagtcacg acgttgtaaa acgacggcca  7200
gtgaattagt actctagctt aagtaacgcc attttgcaag catggaaaa tacataactg  7260
agaatagaga agttcaga                                                7278

SEQ ID NO: 16           moltype = DNA    length = 7269
FEATURE                 Location/Qualifiers
misc_feature            1..7269
                        note = pMP71-TCR1405hc
source                  1..7269
                        mol_type = other DNA
                        organism = synthetic construct
SEQUENCE: 16
tcaaggttag gaacagagag acagcagaat atgggccaaa caggatatct gtggtaagca    60
gttcctgccc cggctcaggg ccaagaacag ttggaacagc agaatatggg ccaaacagga   120
tatctgtggt aagcagttcc tgccccggct cagggccaag aacagttgga acagcagaat   180
atgggcccga gtcagcagtt tctagagaac atcagatgtt tccagggtgc cccaaggacc   240
tgaaatgacc ctgtgcctta tttgaactaa ccaatcagtt cgcttctcgc ttctgttcgc   300
gcgcttctgc tccccgagct caataaaaga gcccacaacc cctcactcgg cgcgccagtc   360
ctccgataga ctgcgtcgcc cgggtacccg tattcccaat aaagcctctt gctgtttgca   420
tccgaatcgt ggactcgctg atccttggga gggtctcctc agattgattg actgcccacc   480
tcgggggtct ttcatttgga ggttccaccg agatttggag acccctgccc agggaccacc   540
gacccccccg ccgggaggta agctggccag cggtcgtttc gtgtctgtct ctgtctttgt   600
gcgtgtttgt gccggcatct aatgtttgcg cctgcgtctg tactagttgg ctaactagat   660
ctgtatctgg cggtcccgcg gaagaactga cgagttcgta ttcccggccg cagccctgg   720
gagacgtccc agcggcctcg ggggcccgtt ttgtggccca ttctgtatca gttaacctac   780
ccgagtcgga cttttggag ctccgccact gtccagggg tacgtggctt tgttggggga   840
cgagacagag agacacttcc cgccccccgtc tgaattttg ctttcggttt tacgccgaaa   900
ccgcgccgcg cgtcttgtct gctgcagcat cgttctgtgt tgtctctgtc tgactgtgtt   960
tctgtatttg tctgaaaatt agctcgacaa agttaagtaa tagtccctct ctccaagctc  1020
acttacaggc ggccgccacc atgctgtctt tgttgctgct gctgctgggc ctgggcagcg  1080
tgttctctgc cgtgatcagc cagaagccca gccgggacat ctgccagaga ggcaccagcc  1140
tgaccatcca gtgccaggtg gacagccaag tgaccatgat gttctggtac agacagcagc  1200
ccggccagag cctgaccctg atcgccacag ccaatcaggg cagcgaggcc acatacgaga  1260
gcggcttcgt gatcgacaag ttccccatca gccgcccaa cctgacctcc agcacccctga  1320
ccgtgtccaa catgagcccc gaggacagca gcatctacct gtgcagcgtg gaacaggaca  1380
ccaacaccgg cgagctgttc ttcggcgagg gcagcagact gaccgtgctg gaagacctga  1440
agaacgtgtt ccccccgag gtggccgtgt cgagcccag cgaggccgag atcagccaca  1500
cccagaaagc caccctggtg tgcctggcca ccggcttcta ccccgaccac gtggagctgt  1560
cttggtgggt gaacggcaaa gaggtgcaca gcggcgtcag caccgacccc cagcccctga  1620
aagagcagcc cgccctgaac gacagccggt actgcctgag cagtagactg agagtgaccg  1680
ccaccttctg gcagaacccc cggaaccact ccggtgcca ggtgcagttc tacggcctga  1740
gcgagaacga cgagtggacc caggacagag ccaagcccgt gacccagatc gtgagcgccg  1800
aggcctgggg cagagccgac tgcggcttca ccagcgagag ctaccagcag ggcgtgctgt  1860
ccgccacaat cctgtacgag atcctgctgg gcaaggccaa cctgtacgcc gtgctggtgt  1920
ccgccctggt gctgatggcc atggtgaagc gaaaggacag ccgcggcgca gccgcggcca  1980
ccaactttag cctgctgaaa caggccggcg acgtggaaga gaaccctggc cctatgacca  2040
gcatccgggc cgtgttcatc ttcctgtggc tgcagctgga cctcgtgaac ggcgagaatg  2100
tggaacagca cccctccacc ctgagcgtgc aggaaggcga tagcgccgtg attaagtgca  2160
cctacagcga cagcgccagc aactacttcc cctggtacaa gcaggaactg ggaaagggcc  2220
cccagcgat catcgacatc cggtccaacg tgggcgagaa gaaagatcag cggatcgccg  2280
tgaccctgaa caagaccgcc aagcacttca gcctgcacat caccgagaca cagcccgagg  2340
actccgccgt gtactctgtg ccgccagac ccaacagcgg caacaccct ctggtgttcg  2400
gcaagggcac acggctgagc gtgatcgcca atatccagaa ccccgacccc gccgtgtacc  2460
agctgcggga cagcaagagc agcgacaaga gcgtgtgcct gttcaccgac ttcgacagcc  2520
agaccaacgt gagccagagc aaggactccg acgtgtacat caccgacaag accgtgctgg  2580
```

```
acatgcggag catggacttc aagagcaact ccgccgtggc ctggtccaac aagagcgact   2640
tcgcctgcgc caacgccttc aacaacagca tcatcccga ggacaccttt ttccccagcc   2700
ccgagagcag ctgcgacgtg aaactggtgg agaagagctt cgagaccgac accaacctga   2760
acttccagaa cctgtccgtg atcggcttcc ggatcctgct gctgaaggtg gccggcttca   2820
acctgctgat gaccctgcgg ctgtggagca gctgaattcg agcatccttac cgccatttat   2880
tcccatattt gttctgtttt tcttgatttg gtatacatt taaatgttaa taaaacaaaa   2940
tggtggggca atcatttaca ttttatggga tatgtaatta ctagttcagg tgtattgcca   3000
caagacaaac atgttaagaa actttcccgt tatttacgct ctgttcctgt taatcaacct   3060
ctggattaca aaatttgtga aagattgact gatattctta actatgttgc tccttttacg   3120
ctgtgtggat atgctgcttt aatgcctctg tatcatgcta ttgcttcccg tacggctttc   3180
gttttctcct ccttgtataa atccggttg ctgtctcttt atgaggagtt gtggcccgtt   3240
gtccgtcaac gtggcgtggt gtgctctgtg tttgctgacg caaccccac tggctggggc   3300
attgccacca cctgtcaact cctttctggg actttcgctt tcccctcccc gatcgccacg   3360
gcagaactca tcgccgcctg ccttgcccgc tgctggacag gggctaggtt gctgggcact   3420
gataattccg tggtgttgtc ggggaagctg acgtcctttc catggctgct cgcctgtgtt   3480
gccaactgga tcctgcgcgg gacgtccttc tgctacgtcc cttcggctct caatccagcg   3540
gacctcccctt cccgaggcct tctgccggtt ctgcggcctc tcccgcgtct tcgctttcgg   3600
cctccgacga gtcggatctc cctttgggcc gcctccccgc ctgtttcgcc tcggcgtccg   3660
gtccgtgttg cttggtcgtc acctgtgcag aattgcgaac catggattcc accgtgaact   3720
ttgtctcctg gcatgcaaat cgtcaacttg gcatgccaag aattaattcg gatccaagct   3780
taggcctgct cgctttcttg ctgtcccatt tctattaaag gttcctttgt tccctaagtc   3840
caactactaa actgggggat attatgaagg gcctgaacta tctggattct gcctagcgt   3900
aagcttaaca cgagccatag atagaataaa agatttatt tagtctccag aaaaaggggg   3960
gaatgaaaga ccccacctgt aggtttggca agctagctta agtaacgcca ttttgcaagg   4020
catggaaaat acataactga gaatagaaa gttcagatca aggttaggaa cagagagaca   4080
gcagaatatg ggccaaacag gatatctgtg gtaagcagtt cctgccccgg ctcagggcca   4140
agaacagttg gaacagcaga atatgggcca aacaggatat ctgtggtaag cagttcctgc   4200
cccggctcag ggccaagaac agatggtccc cagatgcggt cccgccctca gcagtttcta   4260
gagaaccatc agatgtttcc agggtgcccc aaggacctga aatgaccctg tgccttattt   4320
gaactaacca atcagttcgc ttctcgcttc tgttcgcgag cttctgctcc ccgagctcaa   4380
taaaagagcc cacaacccct cactcggcgc gccagtcctc cgatagactg cgtcgcccgg   4440
gtaccgtgt tctcaataaa ccctcttgca gttgcatccg actcgtggtc tcgctgttcc   4500
ttgggagggt ctcctctgag tgattgactg cccacctcgg gggtctttca ttctcgagca   4560
gcttggcgta atcatggtca tagctgtttc ctgtgtgaaa ttgttatccg ctcacaattc   4620
cacacaacat acgagccgga agcataaagt gtaaagcctg gggtgcctaa tgagtgagct   4680
aactcacatt aattgcgttg cgctcactgc ccgctttcca gtcgggaaac ctgtcgtgcc   4740
agctgcatta atgaatcggc caacgcgcgg ggagaggcgg tttgcgtatt gggcgctctt   4800
ccgcttcctc gctcactgac tcgctgcgct cggtcgttcg gctgcggcga gcggtatcag   4860
ctcactcaaa ggcggtaata cggttatcca cagaatcagg ggataacgca ggaaagaaca   4920
tgtgagcaaa aggccagcaa aaggccagga accgtaaaaa ggccgcgttg ctggcgtttt   4980
tccataggct ccgcccccct gacgagcatc acaaaaatcg acgctcaagt cagaggtggc   5040
gaaacccgac aggactataa agataccagg cgtttccccc tggaagctcc ctcgtgcgct   5100
ctcctgttcc gaccctgccg cttaccggat acctgtccgc ctttctccct tcgggaagcg   5160
tggcgctttc tcatagctca cgctgtaggt atctcagttc ggtgtaggtc gttcgctcca   5220
agctgggctg tgtgcacgaa ccccccgttc agcccgaccg ctgcgcctta tccggtaact   5280
atcgtcttga gtccaacccg gtaagacacg acttatcgcc actggcagca gccactggta   5340
acaggattag cagagcgagg tatgtaggcg gtgctacaga gttcttgaag tggtggccta   5400
actacggcta cactagaaga acagtatttg gtatctgcgc tctgctgaag ccagttacct   5460
tcggaaaaag agttggtagc tcttgatccg gcaaacaaac caccgctggt agcggtggtt   5520
tttttgtttg caagcagcag attacgcgca gaaaaaaagg atctcaagaa gatcctttga   5580
tcttttctac ggggtctgac gctcagtgga acgaaaactc acgttaaggg attttggtca   5640
tgagattatc aaaaaggatc ttcacctaga tccttttaaa ttaaaaatga agttttaaat   5700
caatctaaag tatatatgag taaacttggt ctgacagtta ccaatgctta atcagtgagg   5760
cacctatctc agcgatctgt ctatttcgtt catccatagt tgcctgactc cccgtcgtgt   5820
agataactac gatacgggag ggcttaccat ctggccccag tgctgcaatg ataccgcgag   5880
acccacgctc accggctcca gatttatcag caataaacca gccagccgga agggccgagc   5940
gcagaagtgg tcctgcaact ttatccgcct ccatccagtc tattaattgt tgccgggaag   6000
ctagagtaag tagttcgcca gttaatagtt tgcgcaacgt tgttgccatt gctacaggca   6060
tcgtggtgtc acgctcgtcg tttggtatgg cttcattcag ctccggttcc caacgatcaa   6120
ggcgagttac atgatccccc atgttgtgca aaaaagcggt tagctccttc ggtcctccga   6180
tcgttgtcag aagtaagttg gccgcagtgt tatcactcat ggttatggca gcactgcata   6240
attctcttac tgtcatgcca tccgtaagat gcttttctgt gactggtgag tactcaacca   6300
agtcattctg agaatagtgt atgcggcgac cgagttgctc ttgcccggcg tcaatacggg   6360
ataataccgc gccacatagc agaactttaa aagtgctcat cattggaaaa cgttcttcgg   6420
ggcgaaaact ctcaaggatc ttaccgctgt tgagatccag ttcgatgtaa cccactcgtg   6480
cacccaactg atcttcagca tcttttactt tcaccagcgt ttctgggtga gcaaaaacag   6540
gaaggcaaaa tgccgcaaaa aagggaataa gggcgacacg gaaatgttga atactcatac   6600
tcttcctttt tcaatattat tgaagcattt atcagggtta ttgtctcatg agcggataca   6660
tatttgaatg tatttagaaa aataaacaaa taggggttcc gcgcacattt ccccgaaaag   6720
tgccacctga cgtctaagaa accattatta tcatgacatt aacctataaa aataggcgta   6780
tcacgaggcc ctttcgtctc gcgcgtttcg gtgatgacgg tgaaaacctc tgacacatgc   6840
agctcccgga gacggtcaca gcttgtctgt aagcggatgc cggagcagac aagcccgtc   6900
agggcgcgtc agcgggtgtt ggcgggtgtc ggggctggct taactatgcg gcatcagagc   6960
agattgtact gagagtgcac catatgcggt gtgaaatacc gcacagatgc gtaaggagaa   7020
aataccgcat caggcgccat tcgccattca ggctgcgcaa ctgttgggaa gggcgatcgg   7080
tgcgggcctc ttcgctatta cgccagctgg cgaaagggg atgtgctgca aggcgattaa   7140
gttgggtaac gccagggttt tcccagtcac gacgttgtaa aacgacggcc agtgaattag   7200
tactctagct taagtaacgc catttgcaa ggcatggaaa atacataact gagaatagag   7260
aagttcaga                                                            7269
```

```
SEQ ID NO: 17           moltype = DNA  length = 7239
FEATURE                 Location/Qualifiers
misc_feature            1..7239
                        note = pMP71_1405_mc
source                  1..7239
                        mol_type = other DNA
                        organism = synthetic construct
SEQUENCE: 17
tcaaggttag gaacagagag acagcagaat atgggccaaa caggatatct gtggtaagca    60
gttcctgccc cggctcaggg ccaagaacag ttggaacagc agaatatggg ccaaacagga   120
tatctgtggt aagcagttcc tgccccggct cagggccaag aacagatggt ccccagatgc   180
ggtcccgccc tcagcagttt ctagagaacc atcagatgtt ccagggtgc cccaaggacc    240
tgaaatgacc ctgtgcctta tttgaactaa ccaatcagtt cgcttctgc ttctgttcgt    300
gcgcttctgc tccccgagct caataaaaga gcccacaacc cctcactcgg cgcgccagtc   360
ctccgataga ctgcgtcgcc cgggtacccg tattcccaat aaagcctctt gctgtttgca   420
tccgaatcgt ggactcgctg atccttggga gggtctcctc agattgattg actgcccacc   480
tcgggggtct ttcatttgga ggttccaccg agatttggaa acccctgccc agggaccacc   540
gacccccccg ccgggaggta agctggccag cggtcgtttc gtgtctgtct ctgtcttttgt   600
gcgtgtttgt gccggcatct aatgtttgcg cctgcgtctg tactagttgg ctaactagat   660
ctgtatctgc cggtcccgcg gaagaactga cgagttcgta ttcccggccg cagccctgg    720
gagacgtccc agcggcctcc gggcccgtt ttgtgcctca ttctgtatca gttaacctac    780
ccgagtcgga ctttttgag ctccgccact gtccgagggg tacgtggctt tgttggggga   840
cgagagacag agacacttcc cgccccgtc tgaattttg ctttcggtt tacgccgaaa     900
ccgcgccgcg cgtcttgtct gctgcagcat cgttctgtgt tgtctctgtc tgactgtgtt   960
tctgtatttg tctgaaaatt agctcgacaa agttaagtaa tagtccctct ctccaagctc  1020
acttacaggc ggccgccacc atgctgtctt tgttgctgct gctgctgggc ctgggcagca  1080
tgttctctgc cgtgatcagc cagaagccca gccgggacat ctgccagaga ggcaccagcc  1140
tgaccatcca gtgccaggtg gacagccaag tgaccatgat gttctggtac agacagcagc  1200
ccggccagag cctgaccctg atcgccacag ccaatcagac cagcgaggcc acatacgaga  1260
gcggcttcgt gatcgacaag ttccccatca gccggcccaa cctgaccttc agcaccctga  1320
ccgtgtccaa catgagcccc gaggacagca gcatctacct gtgcagcgtg aacaggaca   1380
ccaacaccg cgagctgttc ttcggcgagg cagcagact accgtgctg aagatctgc      1440
ggaacgtgac cccccccaag gtgtccctgt tcgagcctag caaggccgag atcgccaaca  1500
agcagaaagc caccctcgtg tgcctggcca gaggcttctt ccccgaccac gtgaactgt   1560
cttggtgggt caacgcaaa gaggtgcaca cggcgtgtc caccgatccc caggcctaca   1620
aagagagcaa ctacagctac tgcctgagca gcaggctgcg ggtgtccgcc accttctggc  1680
acaaccccg gaaccacttc agatgccagg tgcagtttca cggcctgagc gaagaggaca  1740
agtggccgga gggcaaccc aagcccgtga cccagaatat ttctgccgaa gcctggggca  1800
gagccgactg cggaatcaca agcgccagct accatcaggg cgtgctgagc gccacaatcc  1860
tgtacgagat cctgctgggc aaggccaccc tgtacgccgt gctggtgtct ggcctggtgc  1920
tgatggccat ggtcaagaag aagaactccg gcagcggcgc caccaacttt agcctgctga  1980
aacaggccgg cgacgtggaa gagaaccctg gccctatgac cagcatccgg gccgtgttca  2040
tcttcctgtg gctgcagctg gacctcgtga acgcgagaa tgtggaacag cacccctcca  2100
ccctgagcgt gcaggaaggc gatagcgccg tgattaagtg cacctacagc gacagcgcca  2160
gcaactactt ccctggtac aagcaggaac tgggaaaggg ccccagctg atcatcgaca   2220
tccggtccaa cgtgggcgag aagaaggacc agagaatcgc cgtgacctg aacaagaccg   2280
ccaagcactt cagcctgcac atcaccgaga cacagcccga ggactccgcc gtgtacttct  2340
gtgccgccag acccaacagc ggcaacaccc tctggtgtt cggcaagggc acacggctga  2400
gcgtgatcgc caatatccag aaccccgagc ctgccgtgta ccagctgaag gaccccaaa   2460
gccaggatag caccctgtgc ctgttcaccg acttcgacag ccagatcaac gtgccccaga  2520
ccatggaaag cggcaccttc atcaccgaca gacagtgct ggacatgaag gccatggaca  2580
gcaagagcaa cggcgccatt gcctggtcca accagaccag cttcacatgc caggacatct  2640
caaagagac aaacgccacc tacccagca gcgacgtgcc ctgtgatgcc accctgacag   2700
agaagtcctt cgagacagac atgaacctga acttccgtg atgggcctga                2760
gaatcctgct gctgaaagtg gccggattca acctgctgat gaccctgcgg ctgtggtcca  2820
gctgaattcg agcatcttac cgccatttat tcccatattt gttctgtttt tcttgatttg  2880
ggtatacatt taaatgttaa taaaacaaa tggtggggca atcatttaca ttttatggga   2940
tatgtaatta ctagttcagg tgtattgcca caagacaaac atgttaagaa actttcccgt  3000
tatttacgct ctgttcctgt taatcaacct ctggattaca aaatttgtga aagattgact  3060
gatattctta actatgttgc tccttttacg ctgtgtggat atgctgcttt aatgcctctg  3120
tatcatgcta ttgcttcccg tacggctttc gttttctcct ccttgtataa atcctggttg  3180
ctgtctcttt atgaggagtt gtggcccgtt gtccgtcaac gtggcgtggt gtgctctgtg  3240
tttgctgacg caaccccac tggctggggc attgccaca cctgtcaact cctttctgg   3300
actttcgctt tcccctccc gatcgccacg gcagaactca tcgccgcctg ccttgcccgc  3360
tgctggacag gggctaggtt gctgggcact gataattccg tggtgttgtc ggggaagctg  3420
acgtcctttc catggctgct cgcctgtgtt gccaactgga tcctgcgcgg acgtccttc   3480
tgctacgtcc cttcggctct caatccagcg gacctcccc ccgaggcct tctgccggtt   3540
ctgcggcctc tcccgcgtct tcgctttcgg cctccgacga tcgcgatctc ccttgggcgt  3600
gcctcccgc ctgtttcgcc tcggcgtccg tcgtgtttg cttggtcgtc acctgtgcag   3660
aattgcgaac catggattcc accgtgaact ttgtctcctg catgcaaat cgtcaactg    3720
gcatgccaag aattaattcg gatcaagct taggcctgct cgcttttctg ctgtcccatt  3780
tctattaaag gttcctttgt tccctaagtc aactactaa actgggggat attatgaagg   3840
gccttgagca tctgattct gcctagcgct aagctaaaca ggcccatag ataagataaa    3900
agattttatt tagtctccag aaaaggggg gaatgaaaga cccacctgt aggtttggca    3960
agctagctta agtaacgcca ttttgcaagg catggaaaat acataactga gaatagaaa   4020
gttcagatca aggttaggaa cagagagaca gcagaatatg ggccaaacag gatatctgtg  4080
gtaagcagtt cctgccccgg ctcagggcca agaacagttg aacagcaga atatgggcca   4140
aacaggatat ctgtggtaag cagttcctgc cccggctcag ggccaagaac agatggtccc  4200
```

```
cagatgcggt cccgcccctca gcagtttcta gagaaccatc agatgtttcc agggtgcccc  4260
aaggacctga aatgaccctg tgccttattt gaactaacca atcagttcgc ttctcgcttc  4320
tgttcgcgcg cttctgctcc ccgagctcaa taaaagagcc cacaaccct cactcggcgc   4380
gccagtcctc cgatagactg cgtcgcccgg gtacccgtgt tctcaataaa ccctcttgca  4440
gttgcatccg actcgtggtc tcgctgttcc ttgggaggtc ctcctctgag tgattgactg  4500
cccacctcgg gggtctttca ttctcgagca gcttggcgta atcatggtca tagctgtttc  4560
ctgtgtgaaa ttgttatccg ctcacaattc cacacaacat acgagccgga agcataaagt  4620
gtaaagcctg gggtgcctaa tgagtgagct aactcacatt aattgcgttg cgctcactgc  4680
ccgcttttcca gtcgggaaac ctgtcgtgcc agctgcatta atgaatcggc caacgcgcgg  4740
ggagaggcgg tttgcgtatt gggcgctctt ccgcttcctc gctcactgac tcgctgcgct  4800
cggtcgttcg gctgcggcga gcggtatcag ctcactcaaa ggcggtaata cggttatcca  4860
cagaatcagg ggataacgca ggaaagaaca tgtgagcaaa aggccagcaa aaggccagga  4920
accgtaaaaa ggccgcgttg ctggcgtttt tccataggct ccgcccccct gacgagcatc  4980
acaaaaatcg acgctcaagt cagaggtggc gaaacccgac aggactataa agataccagg  5040
cgtttccccc tggaagctcc ctcgtgcgct ctcctgttcc gaccctgccg cttaccggat  5100
acctgtccgc ctttctccct tcgggaagcg tggcgctttc tcatagctca cgctgtaggt  5160
atctcagttc ggtgtaggtc gttcgctcca agctgggctg tgtgcacgaa ccccccgttc  5220
agcccgaccg ctgcgcctta tccggtaact atcgtcttga gtccaacccg gtaagacacg  5280
acttatcgcc actggcagca gccactggta acaggattag cagagcgagg tatgtaggcg  5340
gtgctacaga gttcttgaag tggtggccta actacggcta cactagaaga acagtatttg  5400
gtatctgcgc tctgctgaag ccagttacct tcggaaaaag agttggtagc tcttgatccg  5460
gcaaacaaac caccgctggt agcggtggtt tttttgtttg caagcagcag attacgcgca  5520
gaaaaaaagg atctcaagaa gatcctttga tcttttctac ggggtctgac gctcagtgga  5580
acgaaaactc acgttaaggg attttggtca tgagattatc aaaaaggatc ttcacctaga  5640
tccttttaaa ttaaaaatga agttttaaat caatctaaag tatatatgag taaacttggt  5700
ctgacagtta ccaatgctta atcagtgagg cacctatctc agcgatctgt ctatttcgtt  5760
catccatagt tgcctgactc cccgtcgtgt agataactac gatacgggag ggcttaccat  5820
ctggccccag tgctgcaatg ataccgcgag acccacgctc accggctcca gatttatcag  5880
caataaacca gccagccgga agggccgagc gcagaagtgg tcctgcaact ttatccgcct  5940
ccatccagtc tattaattgt tgccgggaag ctagagtaag tagttcgcca gttaatagtt  6000
tgcgcaacgt tgttgccatt gctacaggca tcgtggtgtc acgctcgtcg tttggtatgg  6060
cttcattcag ctccggttcc caacgatcaa ggcgagttac atgatccccc atgttgtgca  6120
aaaaagcggt tagctccttc ggtcctccga tcgttgtcag aagtaagttg gccgcagtgt  6180
tatcactcat ggttatggca gcactgcata attctcttac tgtcatgcca tccgtaagat  6240
gcttttctgt gactggtgag tactcaacca agtcattctg agaatagtgt atgcggcgac  6300
cgagttgctc ttgcccggcg tcaatacggg ataataccgc gccacatagc agaactttaa  6360
aagtgctcat cattggaaaa cgttcttcgg ggcgaaaact ctcaaggatc ttaccgctgt  6420
tgagatccag ttcgatgtaa cccactcgtg cacccaactg atcttcagca tcttttactt  6480
tcaccagcgt ttctgggtga gcaaaaacag gaaggcaaaa tgccgcaaaa aagggaataa  6540
gggcgacacg gaaatgttga atactcatac tcttcctttt tcaatattat tgaagcattt  6600
atcagggtta ttgtctcatg agcggataca tatttgaatg tatttagaaa aataaacaaa  6660
taggggttcc gcgcacattt ccccgaaaag tgccacctga cgtctaagaa accattatta  6720
tcatgacatt aacctataaa aataggcgta tcacgaggcc ctttcgtctc gcgcgtttcg  6780
gtgatgacgg tgaaaacctc tgacacatgc agctcccgga gacggtcaca gcttgtctgt  6840
aagcggatgc cgggagcaga caagcccgtc agggcgcgtc agcgggtgtt ggcgggtgtc  6900
ggggctggct taactatgcg gcatcagagc agattgtact gagagtgcac catatgcggt  6960
gtgaaatacc gcacagatgc gtaaggagaa aataccgcat caggcgccat tcgccattca  7020
ggctgcgcaa ctgttgggaa gggcgatcgg tgcgggcctc ttcgctatta cgccagctgg  7080
cgaaaggggg atgtgctgca aggcgattaa gttgggtaac gccagggttt tcccagtcac  7140
gacgttgtaa aacgacggcc agtgaattag tactctagct taagtaacgc catttttgcaa  7200
ggcatggaaa atacataact gagaatagag aagttcaga                           7239

SEQ ID NO: 18           moltype = DNA   length = 7269
FEATURE                 Location/Qualifiers
misc_feature            1..7269
                        note = pMP71-TCR1405mmc
source                  1..7269
                        mol_type = other DNA
                        organism = synthetic construct
SEQUENCE: 18
tcaaggttag gaacagagag acagcagaat atgggccaaa caggatatct gtggtaagca   60
gttcctgccc cggctcaggg ccaagaacag ttggaacagc agaatatggg ccaaacagga  120
tatctgtggt aagcagttcc tgcccccggct cagggccaag aacagatggt ccccagatgc  180
ggtcccgccc tcagcagttt ctagagaacc atcagatgtt tccagggtgc cccaaggacc  240
tgaaatgacc ctgtgcctta tttgaactaa ccaatcagtt cgcttctcgc ttctgttcgc  300
gcgcttctgc tccccgagct caataaaaga gcccacaacc cctcactcgg cgcgccagtc  360
ctccgataga ctgcgtcgcc cgggtacccg tattcccaat aaagcctctt gctgtttgca  420
tccgaatcgt ggactcgctg atccttggga gggtctcctc agattgattg actgcccacc  480
tcggggggtct ttcatttgga ggttccaccg agatttgaag accccgccc aggaccaccc  540
gacccccccg ccgggaggta agctggccag cggtcgtttc gtgtctgtct ctgtctttgt  600
gcgtgttttgt gccggcatct aatgtttgcg cctgcgtctg tactagttgg ctaactagat  660
ctgtatctgg cggtcccgcg gaagaactga cgagttcgta ttcccggccg cagcccctgg  720
gagacgtccc agcggcctcg ggggcccgtt tgtggcccca ttctgtatca gttaacctac  780
ccgagtcgga ctttttggag ctccgccact gtccgaggtg tacgtgcctt tgttggggga  840
cgagagacag agacacttcc cgcccccgtc tgaattttg ctttcggttt tacgccgaaa  900
ccgcgccgcg cgtcttgtct gctgcagcat cgttctgtgt tgtctctgtc tgactgtgtt  960
tctgtatttg tctgaaaatt agctcgacaa agttaagtaa tagtccctct ctccaagctc  1020
acttacaggc ggccgccacc atgctgtctt tgttgctgct gctgctgggc ctgggcagcg  1080
tgttctctgc cgtgatcagc cagaagccca gccgggacat ctgccagaga ggcaccagcc  1140
```

```
tgaccatcca gtgccaggtg gacagccaag tgaccatgat gttctggtac agacagcagc   1200
ccggccagag cctgaccctg atcgccacag ccaatcaggg cagcgaggcc acatacgaga   1260
gcggcttcgt gatcgacaag ttccccatca gccggcccaa cctgaccttc agcaccctga   1320
ccgtgtccaa catgagcccc gaggacagca gcatctacct gtgcagcgtg aacaggaca    1380
ccaacaccgg cgagctgttc ttcggcgagg gcagcagact gaccgtgctg gaagacctga   1440
agaacgtgtt ccccccgag gtggccgtgt cgagcccag caaggccgag atcgcccaca    1500
cccagaaagc cacctggtg tgcctggcca ccggcttcta ccccgaccac gtggaactgt    1560
cttggtgggt gaacggcaaa gaggtgcaca gcggcgtgtg taccgacccc cagccctga    1620
aagagcagcc tgccctgaac gactcccggt actgcctgag cagccggctg agagtgtccg   1680
ccaccttctg gcagaacccc cggaaccact tcagatgcca ggtgcagttc tacggcctga   1740
gcgagaacga cgagtggacc caggaccggg ccaagcccgt gacccagatt gtgtctgccg   1800
aggcctgggg cagagctgat tgtggcatca ccagcgccag ctaccaccag ggcgtgctga   1860
gcgccaccat cctgtacgag atcctgctgg gcaaggccac cctgtacgcc gtgctggtgt   1920
ccgccctggt gctgatggcc atggtgaaac ggaaggacag cagggcggc acgcggcgca    1980
ccaactttag cctgctgaaa caggccggcg acgtggaaga gaaccctggc cctatgacca   2040
gcatccgggc cgtgttcatc ttcctgtggc tgcagctgga cctcgtgaac ggcgagaatg   2100
tggaacagca cccctccacc ctgagcgtgc aggaaggcga tagcgccgtg attaagtgca   2160
cctacagcga cagcgccagc aactacttcc cctggtacaa gcaggaactg ggaaagggcc   2220
cccagctgat catcgacatc cggtccaacg tgggcgagaa gaaggaccag agaatcgccg   2280
tgaccctgaa caagaccgcc aagcacttca gcctgcacat caccgagaca cagcccgagg   2340
actccgccgt gtacttctgt gccgccgac ccaacagcgg caacacccct ctggtgttcg    2400
gcaagggcac acggctgagc gtgatcgcca atatccgaaa ccccgaccc gccgtgtacc    2460
agctgcggga cagcaagagc agcgacaaga gcgtgtgcct gttcaccgac ttcgacagcc   2520
agaccaacgt gtcccagagc aaggacacgc acgtgtacat caccgacaag tgcgtgctgg   2580
acatgcggag catggacttc aagagcaact ccgccgtggc ctggtccaac aagagcgact   2640
tcgcctgcgc caacgccttc aacaacagca tcatccccga ggacacattc ttccccagct   2700
ccgacgtgcc ctgcgacgtg aagctggtgg aaaagagctt cgagacagac accaacctga   2760
acttccagaa cctgagcgtg atcggcttcc ggatcctgct gctgaaggtg ctggccttca   2820
acctgctgat gaccctgcgg ctgtggagca gctgaattcg agcatcttac cgccatttat   2880
tcccatattt gttctgtttt tcttgatttg ggtatacatt taaatgttaa taaaacaaaa   2940
tggtggggca atcatttaca ttttatggga tatgtaatta ctagttcagg tgtattgcca   3000
caagacaaac atgttaagaa actttcccgt tatttacgct ctgttcctgt taatcaacct   3060
ctggattaca aaatttgtga agattgact gatattctta actatgttgc tccttttacg    3120
ctgtgtggat atgctgcttt aatgcctctg tatcatgctg ttgcttcccg tacggctttc   3180
gttttctcct ccttgtataa atcctggttg ctgtctcttt atgaggagtt gtggccgtt    3240
gtccgtcaac gtggcgtggt gtgctctgtg tttgctgacg caaccccac tggctggggc    3300
attgccacca cctgtcaact cctttctggg actttgcgtt tccccctccc gatcgccacg   3360
gcagaactca tcgccgcctg ccttgcccgc tgctggacag gggctaggtt gctgggcact   3420
gataattccg tggtgttgtc ggggaagctg acgtccttc catggctgct gcctgtgtt    3480
gccaactgga tcctgcgcgg gacgtccttc tgctacgtcc cttcggctct caatccagcg   3540
gacctccctt cccgaggcct tctgccggtt ctgcggcctc tcccgcgtct tcgctttcgg   3600
cctccgacga gtcggatctc ccttgggcc gcctcccgc ctgtttcgcc tcggcgtccg     3660
gtccgtgttg cttggtcgtc acctgtgcag aattgcgaac catggattcc accgtgaact   3720
ttgtctcctg gcatgcaaat cgtcaacttg gcatgccaag aattaattcg gatccaagct   3780
taggcctgct cgctttcttg ctgtcccatt tctattaaag gttcctttgt tcctaagtc    3840
caactactaa actgggggat attatgaagg gccttgcagca tctggattct gcctagcgct   3900
aagcttaaca cgagccatag atagaataaa agatttttatt tagtctccag aaaaaggggg   3960
gaatgaaaga ccccacctgt aggtttggca agctagctta agtaacgcca ttttgcaagg   4020
catgaaaat acataactga gatagagaa gttcagatca aggttaggaa cagagagaca     4080
gcagaatatg ggccaaacag gatatctgtg gtaagcagtt cctgccccgg ctcagggcca   4140
agaacagttg gaacagcaga atatgggcca aacaggatat ctgtggtaag cagttcctgc   4200
cccggctcag ggccaagaac agatggtccc cagatgcggt cccgccctca gcagtttcta   4260
gagaaccatc agatgtttcc agggtgcccc aaggacctga aatgaccctg tgccttattt   4320
gaactaacca atcagttcgc ttctcgcttc tgttcgcgcg cttctgctcc ccgagctcaa   4380
taaaagagcc cacaaccct cactcgtcgc gccagtcctc cgatagactg gtcgcccgg     4440
gtacccgtgt tctcaataaa ccctcttgca gttgcatccg actcgtggtc tcgctgttcc   4500
ttgggagggt ctcctctgag tgattgactg cccacctcgg gggtctttca ttctcgagca   4560
gcttggcgta atcatggtca tagctgtttc ctgtgtgaaa ttgttatccg ctcacaattc   4620
cacacaacat acgagccgga agcataaagt gtaaagcctg gggtgcctaa tgagtgagct   4680
aactcacatt aattgcgttg cgctcactgc ccgctttcca gtcgggaaac ctgtcgtgcc   4740
agctgcatta atgaatcggc caacgcgcgg ggagaggcgg tttgcgtatt gggcgctctt   4800
ccgcttcctc gctcactgac tcgctgcgct cggtcgttcg gctgcggcga gcggtatcag   4860
ctcactcaaa ggcggtaata cggttatcca cagaatcagg ggataacgca ggaaagaaca   4920
tgtgagcaaa aggccagcaa aaggccagga accgtaaaaa ggccgcgttg ctggcgtttt   4980
tccataggct ccgccccct gacgagcatc acaaaaatcg acgctcaagt cagaggtggc    5040
gaaacccgac aggactataa agataccagg cgtttccccc tggaagctcc ctcgtgcgct   5100
ctcctgttcc gaccctgccg cttaccggat acctgtccgc ctttctccct tcgggaagcg   5160
tggcgctttc tcatagctca cgctgtaggt atctcagttc ggtgtaggtc gttcgctcca   5220
agctggactg tgtgcacgaa ccccccgttc agcccgaccg ctgcgcctta tccggtaact   5280
atcgtcttga gtccaacccg gtaagacacg acttatcgcc actggcagca gccactggta   5340
acaggattag cagagcgagg tatgtaggcg gtgctacaga gttcttgaag tggtggccta   5400
actacggcta cactagaaga acagtatttg gtatctgcgc tctgctgaag ccagttacct   5460
tcggaaaaag agttggtagc tcttgatccg gcaaacaaac caccgctggt agcggtggtt   5520
tttttgtttg caagcagcag attacgcgca gaaaaaaagg atctcaagaa gatccttttga  5580
tcttttctac ggggtctgac gctcagtgga acgaaaactc acgttaaggg attttggtca   5640
tgagattatc aaaaaggatc ttcacctaga tccttttaaa ttaaaaatga agttttaaat   5700
caatctaaag tatatatgag taaacttggt ctgacagtta ccaatgctta atcagtgagg   5760
cacctatctc agcgatctgt ctatttcgtt catccatagt tgcctgactc ccgtcgtgt    5820
agataactac gatacgggag ggcttaccat ctggccccag tgctgcaatg ataccgcgag   5880
```

-continued

```
acccacgctc accggctcca gatttatcag caataaacca gccagccgga agggccgagc    5940
gcagaagtgg tcctgcaact ttatccgcct ccatccagtc tattaattgt tgccgggaag    6000
ctagagtaag tagttcgcca gttaatagtt tgcgcaacgt tgttgccatt gctacaggca    6060
tcgtggtgtc acgctcgtcg tttggtatgg cttcattcag ctccggttcc caacgatcaa    6120
ggcgagttac atgatccccc atgttgtgca aaaaagcgtt agctccttc ggtcctccga     6180
tcgttgtcag aagtaagttg gccgcagtgt tatcactcat ggttatggca gcactgcata    6240
attctcttac tgtcatgcca tccgtaagat gcttttctgt gactggtgag tactcaacca    6300
agtcattctg agaatagtgt atgcggcgac cgagttgctc ttgcccggcg tcaatacggg    6360
ataataccgc gccacatagc agaactttaa aagtgctcat cattggaaaa cgttcttcgg    6420
ggcgaaaact ctcaaggatc ttaccgctgt tgagatccag ttcgatgtaa cccactcgtg    6480
cacccaactg atcttcagca tcttttactt tcaccagcgt ttctgggtga caaaaacag     6540
gaaggcaaaa tgccgcaaaa aagggaataa gggcgacacg gaaatgttga atactcatac    6600
tcttcctttt tcaatattat tgaagcattt atcagggtta ttgtctcatg agcggataca    6660
tatttgaatg tatttagaaa aataaacaaa tagggttcc gcgcacattt ccccgaaaag     6720
tgccacctga cgtctaagaa accattatta tcatgacatt aacctataaa aataggcgta    6780
tcacgaggcc ctttcgtctc gcgcgtttcg gtgatgacgg tgaaaacctc tgacacatgc    6840
agctcccgga gacggtcaca gcttgtctgt aagcggatgc cgggagcaga caagcccgtc    6900
agggcgcgtc agcgggtgtt ggcgggtgtc ggggctggct taactatgcg gcatcagagc    6960
agattgtact gagagtgcac catatgcggt gtgaaatacc gcacagatgc gtaaggagaa    7020
aataccgcat caggcgccat cgccattca ggctgcgcaa ctgttgggaa gggcgatcgg     7080
tgcgggcctc ttcgctatta cgccagctgg cgaaaggggg atgtgctgca aggcgattaa    7140
gttgggtaac gccagggttt tcccagtcac gacgttgtaa aacgacggcc agtgaattag    7200
tactctagct taagtaacgc cattttgcaa ggcatggaaa atacataact gagaatagag    7260
aagttcaga                                                            7269

SEQ ID NO: 19      moltype = DNA  length = 7308
FEATURE            Location/Qualifiers
misc_feature       1..7308
                   note = pMP71-TCR1705hc
source             1..7308
                   mol_type = other DNA
                   organism = synthetic construct
SEQUENCE: 19
tcaaggttag gaacagagag acagcagaat atgggccaaa caggatatct gtggtaagca      60
gttcctgccc cggctcaggg ccaagaacag ttggaacagc agaatatggg ccaaacagga    120
tatctgtggt aagcagttcc tgccccggct cagggccaag aacagatggt ccccagatgc    180
ggtcccgccc tcagcagttt ctagagaacc atcagatgtt tccagggtgc cccaaggacc    240
tgaaatgacc ctgtgcctta tttgaactaa ccaatcagtt cgcttctcgc ttctgttcgc    300
gcgcttctgc tccccgagct caataaaaga gcccacaacc cctcactcgg cgcgccagtc    360
ctccgataga ctgcgtcgcc cgggtacccg tattcccaat aaagcctctt gctgtttgca    420
tccgaatcgt ggactcgctg atccttggga gggtctcctc agattgattg actgcccacc    480
tcggggggtc ttcatttgga ggttccaccg agatttggag acccctgccc agggaccacc    540
gacccccccg ccgggaggta agctggccag cggtcgtttc gtgtctgtct tgtgtctttg    600
gcgtgtttgt gccggcatct aatgtttgcg cctgcgtctg tactagttgg ctaactagat    660
ctgtatctgg cggtcccgcg gaagaactga cgagttcgta ttcccggccg cagccctgg     720
gagacgtccc agcggcctcg ggggcccgtt tgtggccca ttctgtatca gttaacctac      780
cgagtcgga cttttggag ctccgccact gtccggagtg tacgtggctt tgttgggga       840
cgagagacag agacacttcc cgccccgtc tgaattttg cttcggttt tacgccgaaa        900
ccgcgccgcg cgtcttgtct gctgcagcat cgttctgtgt tgtctctgtc tgactgtgtt    960
tctgtatttg tctgaaaatt agctcgacaa agttaagtaa tagtccctct ctccaagctc    1020
acttacaggc ggccgccacc atgctgtctc cagatctgtc tgacagccgc tggaacacca    1080
gactgctgtg ccacgtgatg ctgtgcctgc tgggagccgt gtctgtggct gctggcgtga    1140
tccagagccc cagacacctg atcaaagaga gagagagac agccaccctg aagtgctacc      1200
ccatccccag gcacgacacc gtgtactggt atcagcaggg cccaggccag gaccccagt      1260
tcctgatcag cttctacgag aagatgcaga gcgacaaggg cagcatcccc gacagattca    1320
gcgcccagca gttcagcgac taccacagcg agctgaacat gagcagcctg gaactggcgg    1380
acagcgccct gtactctgcc gccagctcct ttagaggcgg cggagccaac gtgctgacct    1440
ttggcgctgg cagcagactg accgtgctgg aagacctgaa gaacgtgttc ccccccgagg    1500
tggccgtgtt cgagcccagc gaggccgaga tcagccacac ccagaaagcc accctggtgt    1560
gcctggccac cggcttctac cccgaccacg tggagctgtc ttggtgggtg aacggcaaag    1620
aggtgcacag cggcgtcagc accgaccccc agccctgaa agagcagccc gccctgaacg     1680
acagccggta ctgcctgagc agccggctga gagtgagcgc caccttctgg cagaacccc     1740
ggaaccactt ccgtgccag gtgcagttct acggcctgag cgagaacgac gagtggaccc      1800
aggacagagc caagcccgtg acccagatcg tgagcgccga gacctggggc agagccgact    1860
gcggcttcac cagcgagagc taccagcagg gcgtgctgtc cgccacaatc ctgtacgaga    1920
tcctgctggg caaggccacc ctgtacgccg tgctggtgtc cgccctggtg ctgatggcca    1980
tggtgaagcg gaaggacagc cggggcggca gcggcgccac caactttagc ctgctgaaac    2040
aggcggcgg cgtggaagag aaccctggcc ccatgatgaa gtccctgcgg gtgctgctcg      2100
tgatcctgtg gctgcagctg agctgggtgt ggtcccagca gaaagaggtg gaacaggacc    2160
caggccctct gagcgtgcca gagggcgcta tcgtgtccct gaattgcacc tacagcaaca    2220
gcgccttcca gtacttcatg tggtacagac agtacagccg gaagggcccc gagctgctga    2280
tgtacaccta ctccagcggc aacaagaggg acggccggtt cacagcccag gtggacaaga    2340
gcagcaagta catctcccctg ttcatccggg acagccagcc cagcgactct gccacatacc   2400
tgtgcgccat gagcgaccac ggcaaccagt tctacttcgg caccggcacc tccctgaccgt   2460
tgatccccaa catccagaac cccgacccg ccgtgtacca gctgcgggac agcaagagca      2520
gcgacaagag cgtgtgcctg ttcaccgact cgacagcca gaccaacgtg agccagagca      2580
aggactccga cgtgtacatc accgacaaga ccgtgctgga catgcggagc atggacttca    2640
agagcaactc cgccgtggcc tggtccaaca agagcgactt cgcctgcgcc aacgccttca    2700
acaacagcat catccccgag gacaccttt tccccagccc cgagagcagc tgcgacgtga    2760
```

```
aactggtgga gaagagcttc gagaccgaca ccaacctgaa cttccagaac ctgtccgtga 2820
tcggcttccg gatcctgctg ctgaaggtgg ccggcttcaa cctgctgatg acccctgcggc 2880
tgtggagcag ctgaattcga gcatcttacc gccatttatt cccatatttg ttctgttttt 2940
cttgatttgg gtatacattt aaatgttaat aaaacaaaat ggtggggcaa tcatttacat 3000
tttatgggat atgtaattac tagttcaggt gtattgccaa aagacaaaca tgttaagaaa 3060
ctttcccgtt atttacgctc tgttcctgtt aatcaacctc tggattacaa aatttgtgaa 3120
agattgactg atattcttaa ctatgttgct ccttttacgc tgtgtggata tgctgcttta 3180
atgcctctgt atcatgctat tgcttcccgt acggctttcg ttttctcctc cttgtataaa 3240
tcctggttgc tgtctcttta tgaggagttg tggcccgttg tccgtcaacg tggcgtggtg 3300
tgctctgtgt ttgctgacgc aaccccccact ggctgggggca ttgccaccac ctgtcaactc 3360
cttttctggga ctttcgcttt cccctcccg atcgccacgg cagaactcat cgccgcctgc 3420
cttgcccgct gctggacagg ggctaggttg ctgggcactg ataattccgt ggtgttgtcg 3480
gggaagctga cgtcctttcc atggctgctc gcctgtgttg ccaactggat cctgcgcggg 3540
acgtccttct gctacgtccc ttcggctctc aatccacgag acctccctcc ccgaggcctt 3600
ctgccggttc tgcggcctct cccgcgtctt cgctttcggc ctccgacgag tcggatctcc 3660
ctttgggccg cctcccgcc tgtttcgcct cggcgtccgg tccgtgttgc ttggtcgtca 3720
cctgtgcaga attgcgaacc atggattcca ccgtgaactt tgtctcctgg catgcaaatc 3780
gtcaacttgg catgccaaga attaattcgg atccaagctt aggcctgctc gctttcttgc 3840
tgtcccattt ctattaaagg ttcctttgtt ccctaagtcc aactactaaa ctggggggata 3900
ttatgaaggg ccttgagcat ctggattctg cctagcgcta agcttaacac gagccataga 3960
tagaataaaa gattttattt agtctccaga aaaggggggg aatgaaagac cccacctgta 4020
ggtttggcaa gctagcttaa gtaacgccat tttgcaaggc atggaaaata cataactgag 4080
aatagagaag ttcagatcaa ggttaggaac agagagacag cagaatatgg gccaaacagg 4140
atatctgtgg taagcagttc ctgccccggc tcagggccaa gaacagttgg aacagcagaa 4200
tatgggccaa acaggatatc tgtggtaagc agttcctgcc ccggctcagg gccaagaaca 4260
gatggtcccc agatgcggtc ccgccctcag cagtttctag agaaccatca gatgtttcca 4320
gggtgcccca aggacctgaa atgaccctgt gccttatttg aactaaccaa tcagttcgct 4380
tctcgcttct gttcgcgcgc ttctgctccc cgagctcaat aaaagagccc acaacccctc 4440
actcggcgcg ccagtcctcc gatagactgc gtcgcccggg tacccgtgtt ctcaataaac 4500
cctcttgcag ttgcatccga tcgtggtct cgctgttcct tgggaggtc tcctctgagt 4560
gattgactgc ccaccctcggg ggtctttcat tctcgagcag cttggcgtaa tcatggtcat 4620
agctgtttcc tgtgtgaaat tgttatccgc tcacaattcc acacaacata cgagccggaa 4680
gcataaagtg taaagcctgg ggtgcctaat gagtgagcta actcacatta ttgcgttgc 4740
gctcactgcc cgctttccag tcgggaaacc tgtcgtgcca gctgcattaa tgaatcggcc 4800
aacgcgcggg gagaggcggt ttgcgtattg ggcgctcttc cgcttcctcg ctcactgact 4860
cgctgcgctc ggtcgttcgg ctgcggcgag cggtatcagc tcactcaaag gcggtaatac 4920
ggttatccac agaatcaggg gataacgcag gaaagaacat gtgagcaaaa ggccagcaaa 4980
aggccaggaa ccgtaaaaag gccgcgttgc tggcgttttt ccataggctc cgcccccctg 5040
acgagcatca caaaatcga cgctcaagtc agaggtggcg aaacccgaca ggactataaa 5100
gataccaggc gtttccccct ggaagctccc tcgtgcgctc tcctgttccg acctctgcgc 5160
ttaccggata cctgtccgcc tttctccctt cgggaagcgt ggcgctttct catagctcac 5220
gctgtaggta tctcagttcg gtgtaggtcg ttcgctccaa gctgggctgt gtgcacgaac 5280
cccccgttca gcccgaccgc tgcgccttat ccggtaacta tcgtcttgag tccaacccgg 5340
taagacacga cttatcgcca ctggcagcag ccactggtaa caggattagc agagcgaggt 5400
atgtaggcgg tgctacagag ttcttgaagt ggtggcctaa ctacggctac actagaagaa 5460
cagtatttgg tatctgcgct ctgctgaagc cagttacctt cggaaaaaga gttggtagct 5520
cttgatccgg caaacaaacc accgctggta gcggtggttt ttttgtttgc aagcagcaga 5580
ttacgcgcag aaaaaaagga tctcaagaag atccttgat cttttctacg ggtctgacgc 5640
tcagtggaa cgaaaactca cgttaaggga ttttggtcat gagattatca aaaaggatct 5700
tcacctagat ccttttaaat taaaaatgaa gttttaaatc aatctaaagt atatatgagt 5760
aaacttggtc tgacagttac caatgcttaa tcagtgaggc acctatctca gcgatctgtt 5820
tatttcgttc atccatagtt gcctgactcc ccgtcgtgta gataactacg atacgggagg 5880
gcttaccatc tggccccagt gctgcaatga taccgcgaga cccacgctca ccggctccag 5940
atttatcagc aataaaccag ccagccgaa gggccgagcg cagaagtggt cctgcaactt 6000
tatccgcctc catccagtct attaattgtt gccgggaagc tagagtaagt agttcgccag 6060
ttaatagttt gcgcaacgtt gttgccattg ctacaggcat cgtggtgtca cgctcgtcgt 6120
ttggtatggc ttcattcagc tccggttccc aacgatcaag gcgagttaca tgatcccca 6180
tgttgtgcaa aaaagcggtt agctccttcg gtcctccgat cgttgtcaga agtaagttgg 6240
ccgcagtgtt atcactcatg gttatggcag cactgcataa ttctcttact gtcatgccat 6300
ccgtaagatg cttttctgtg actggtgagt actcaaccaa gtcattctga gaatagtgta 6360
tgcggcgacc gagttgctct tgcccggcgt caatacggga taataccgcg ccacatagca 6420
gaactttaaa agtgctcatc attggaaaac gttcttcggg gcgaaaactc tcaaggatct 6480
taccgctgtt gagatccagt tcgatgtaac ccactcgtgc acccaactga tcttcagcat 6540
cttttacttt caccagcgtt tctgggtgag caaaaacagg aaggcaaaat gccgcaaaaa 6600
agggaataag ggcgacacgg aaatgttgaa tactcatact cttccttttt caatattatt 6660
gaagcattta tcagggttat tgtctcatga gcggatacat atttgaatgt atttagaaaa 6720
ataaacaaat aggggttccg cgcacatttc cccgaaaagt gccacctgac gtctaagaaa 6780
ccattattat catgacatta acctataaaa ataggcgtat cacgaggccc tttcgtctcg 6840
cgcgtttcgg tgatgacggt gaaaacctct gacacatgca gctcccggag acggtcacag 6900
cttgtctgta agcggatgcc gggagcagac aagcccgtca gggcgcgtca gcgggtgttg 6960
gcgggtgtcg ggctggctt aactatgcgg catcagagca gattgtactg agagtgcacc 7020
atatgcggtg tgaaataccg cacagatgcg taaggagaaa ataccgcatc aggcgccatt 7080
cgccattcag gctgcgcaac tgttgggaag ggcgatcggt gcgggcctct tcgctattac 7140
gccagctggc gaaagggga tgtgctgcaa ggcgattaag ttgggtaacg ccagggtttt 7200
cccagtcacg acgttgtaaa acgacggcca gtgaattagt actctagctt aagtaacgcc 7260
attttgcaag gcatggaaaa tacataactg agaatagaga agttcaga 7308

SEQ ID NO: 20        moltype = DNA   length = 7278
FEATURE              Location/Qualifiers
```

| misc_feature | 1..7278 |
| | note = pMP71_1705_mc |
| source | 1..7278 |
| | mol_type = other DNA |
| | organism = synthetic construct |

SEQUENCE: 20

```
tcaaggttag gaacagagag acagcagaat atgggccaaa caggatatct gtggtaagca   60
gttcctgccc cggctcaggg ccaagaacag ttggaacagc agaatatggg ccaaacagga  120
tatctgtggt aagcagttcc tgccccggct cagggccaag aacagatggt ccccagatgc  180
ggtcccgccc tcagcagttt ctagagaacc atcagatgtt tccagggtgc cccaaggacc  240
tgaaatgacc ctgtgcccta tttgaactaa ccaatcagtt cgcttctcgc ttctgttcgc  300
gcgcttctgc tccccgagct caataaaaga gcccacaacc cctcactcgg cgcgccagtc  360
ctccgataga ctgcgtcgcc cgggtacccg tattcccaat aaagcctctt gctgtttgca  420
tccgaatcgt ggactcgctg atccttggga gggtctcctc agattgattg actgcccacc  480
tcgggggtct ttcatttgga ggttccaccg agatttggag accctgccc agggaccacc  540
gacccccccg ccgggaggta agctggccag cggtcgtttc gtgtctgtct ctgtctttgt  600
gcgtgtttgt gccggcatct aatgtttgcg cctgcgtctg tactagttgg ctaactagat  660
ctgtatctgg cggtcccgcg gaagaactga cgagttcgta ttcccggccg cagcccctgg  720
gagacgtccc agcggcctcg ggggcccgtt ttgtgggcca ttctgtatca gttaacctac  780
ccgagtcgga cttttggag ctcgccact gtccgagggg tacgtggctt tgttggggga  840
cgagagacag agacacttcc cgcccccgtc tgaattttg cttcggttt tacgccgaaa  900
ccgcgccgcg cgtcttgtct gctgcagcat cgttctgtgt tgtctctgtc tgactgtgtt  960
tctgtatttg tctgaaaatt agctcgacaa agttaagtaa tagtccctct ctccaagctc 1020
acttacaggc ggccgccacc atgctgtctc cagatctgcc tgacagcgcc tggaacacca 1080
gactgctgtg ccacgtgatg ctgtgcctgc tgggagccgt gtctgtggct gctggcgtga 1140
tccagaccc cagacacctg atcaaagaga agagagagac agccaccctg aagtgctacc 1200
ccatccccag gcacgacacc gtgtactggt atcagcaggg cccaggccag gaccccagt 1260
tcctgatcag cttctacgag aagatgcaga gcgacaaggg cagcatcccc gacagattca 1320
gcgcccagca gttcagcgac taccacacgc agctgaacat gagcagcctg gaactgggcg 1380
acagcgccct gtacttctgc gccagctcct ttagagcag cggagccaac gtgctgacct 1440
ttggcgctgg cagcagactg accgtgctgg aagatctgcg gaacgtgacc cccccccaagg 1500
tgtccctgtt cgagcctagc aaggccgaga tcgccaacaa gcagaaagcc acactcgtgt 1560
gcctggccag aggcttcttc cccgaccacg tggaactgtc ttggtgggtc aacggcaaag 1620
aggtgcacag cggcgtgtcc accgtcctc aggcctacaa agagacaac tacagctact 1680
gcctgagcag caggctgcgg gtgtccgcca ccttctggca caaccccgg aaccacttca 1740
gatgccaggt gcagtttcac ggcctgagcg aagaggacaa gtgcccgag ggcagcccta 1800
agcccgtgac ccagaatatc tctgccgagg cctggggcag agcgactgt ggaattacca 1860
gcgccagcta ccaccagggc gtgctgtctg ccaccatcct gtacgagatc ctgctgggca 1920
aggccaccct gtacgccgtg ctggtctctg cctggtgct gatggccatg gtcaagaaga 1980
agaacagcgg cagcggcgcc accaaccttta gcctgctgaa acaggccggc gacgtggaag 2040
agaaccctgg ccccatgatg aagtccctgc gggtgctgct cgtgatcctg tggctgcagc 2100
tgagctgggt gtggtcccag cagaaagagg tggaacagga cccaggccct ctgagcgtgc 2160
cagagggcgc tatcgtgtcc ctgaattgca cctacagcaa cagcgccttc cagtacttca 2220
tgtggtacag acagtacagc cggaagggcc ccgagctgct gatgtacacc tactccagcg 2280
gcaacaaaga ggacggccgg ttcacagccc aggtggacaa gagcagcaag tacatctccc 2340
tgttcatccg ggacagccag cccagcgact ctgccacata cctgtgcgcc atgagcgaca 2400
ccggcaacca gttctacttc ggcaccggca cctgatccc acgtgatccc aacatccaga 2460
acccccgagcc cgccgtgtac cagctgaagg acctagaag ccaggacagc acctgtgcc 2520
tgttcaccga cttcgacagc cagatcaacg tgcccaagac catggaaagc ggcaccttca 2580
tcaccgacaa gacagtgctg gacatgaagg ccatggacag caagagcaac ggcgccattg 2640
cctggtccaa ccagaccagc ttcacatgcc aggacatctt caaagagaca acgccacct 2700
accccagcag cgacgtgccc tgtgatgcca cactgaccga gaagtccttc gagacagaca 2760
tgaacctgaa cttccagaac ctgagcgtga tgggcctgag aatcctgctg ctgaaggtgg 2820
ccggcttcaa cctgctgatg accctgagac tgtggtccag ctgaattcga gcatcttacc 2880
gccatttatt cccatatttg ttctgttttt cttgatttgg gtatacattt aaatgttaat 2940
aaaacaaaat ggtggggcaa tcatttacat tttatgggat atgtaattac tagttcaggt 3000
gtattgccac aagacaaaca tgttaagaaa ctttcccgtt atttacgctc tgttcctgtt 3060
aatcaacctc tggattacaa aatttgtgaa agattgactg atattcttaa ctatgttgct 3120
ccttttacgc tgtgtggata tgctgcttta atcatgctat tgcttcccgt 3180
acggctttcg ttttctcctc cttgtataaa tcctggttgc tgtctcttta tgaggagttg 3240
tggcccgttg tccgtcaacg tggcgtggtg tgctctgtgt ttgctgacgc aaccccact 3300
ggctgggca ttgccaccac ctgtcaactc ctttctggga cttcgcttt ccccctcccg 3360
atcgccacgg cagaactcat cgccgcctgc cttgcccgct gctggacagg ggtaggttg 3420
ctgggcacta ataattcgt ggtgtttgtcg gggaagctga cgtccttttc atggctgctg 3480
gcctgtgttg ccaactggat cctgcgcggg acgtcctct gctacgtccc ttcggctctc 3540
aatccagcgg acctccttc cgaggcctt ctgccggttc tgcggcctct cccgcgtctt 3600
cgctttcggc ctcgacgag tcggatcctc cttgggccg cctccccgcc tgttcgcct 3660
cggcgtccgg tccgtgttgc ttggtcgtca cctgtgcaga attgcgaacc atggattcca 3720
ccgtgaactt tgtctcctgg catgcaaatc gtcaacttgg catgcaagaa attaattcga 3780
atccaagctt aggcctgctc gctttcttgc tgtcccattt ctattaaagg ttcctttgtt 3840
ccctaagtcc aactactaaa ctgggggata ttatgaaggg ccttgagcat ctggattctg 3900
cctagcgcta agcttaacac gagccataga tagaataaaa gatttatttt agtctccaga 3960
aaaaggggggg aatgaaagac cccacctgta ggtttggcaa gctagcttaa gtaacgccat 4020
tttgcaaggc atggaaaata cataactgag aataagaaat ttcagatcaa ggttaggaac 4080
agagagacag cagaatatgg gccaaacagg atatctgtgg taagcagttc ctgccccggc 4140
tcagggccaa gaacagttgg aacagcagaa tatgggccaa acaggatatc tgtggtaagc 4200
agttcctgcc ccggctcagg gccaagaaca gatggtcccc agatgcggtc ccgccctcag 4260
cagtttctag agaaccatca gatgtttcca gggtgcccca aggacctgaa atgacccgt 4320
gccttatttg aactaaccaa tcagttcgct tctcgcttct gttcgcgcgc ttctgctccc 4380
```

```
cgagctcaat aaaagagccc acaacccctc actcggcgcg ccagtcctcc gatagactgc 4440
gtcgcccggg tacccgtgtt ctcaataaac cctcttgcag ttgcatccga ctcgtggtct 4500
cgctgttcct tgggagggtc tcctctgagt gattgactgc ccacctcggg ggtctttcat 4560
tctcgagcag cttggcgtaa tcatggtcat agctgtttcc tgtgtgaaat tgttatccgc 4620
tcacaattcc acacaacata cgagccggaa gcataaagtg taaagcctgg ggtgcctaat 4680
gagtgagcta actcacatta ttgcgttgc gctcactgcc cgctttccag tcgggaaacc 4740
tgtcgtgcca gctgcattaa tgaatcggcc aacgcgcggg gagaggcggt ttgcgtattg 4800
ggcgctcttc cgcttcctcg ctcactgact cgctgcgctc ggtcgttcgg ctgcggcgag 4860
cggtatcagc tcactcaaag gcggtaatac ggttatccac agaatcaggg gataacgcag 4920
gaaagaacat gtgagcaaaa ggccagcaaa aggccaggaa ccgtaaaaag gccgcgttgc 4980
tggcgttttt ccataggctc cgcccccctg acgagcatca caaaaatcga cgctcaagtc 5040
agaggtggcg aaacccgaca ggactataaa gataccaggc gtttccccct ggaagctccc 5100
tcgtgcgctc tcctgttccg accctgccgc ttaccggata cctgtccgcc tttctccctt 5160
cgggaagcgt ggcgctttct catagctcac gctgtaggta tctcagttcg gtgtaggtcg 5220
ttcgctccaa gctgggctgt gtgcacgaac cccccgttca gcccgaccgc tgcgccttat 5280
ccggtaacta tcgtcttgag tccaacccgg taagacacga cttatcgcca ctggcagcag 5340
ccactggtaa caggattagc agagcgaggt atgtaggcgg tgctacagag ttcttgaagt 5400
ggtggcctaa ctacggctac actagaagaa cagtatttgg tatctgcgct ctgctgaagc 5460
cagttacctt cggaaaaaga gttggtagct cttgatccgg caaacaaacc accgctggta 5520
gcggtggttt ttttgtttgc aagcagcaga ttacgcgcag aaaaaaagga tctcaagaag 5580
atcctttgat cttttctacg gggtctgacg ctcagtggaa cgaaaactca cgttaaggga 5640
ttttggtcat gagattatca aaaaggatct tcacctagat ccttttaaat taaaaatgaa 5700
gttttaaatc aatctaaagt atatatgagt aaacttggtc tgacagttac caatgcttaa 5760
tcagtgaggc acctatctca gcgatctgtc tatttcgttc atccatagtt gcctgactcc 5820
ccgtcgtgta gataactacg atacgggagg gcttaccatc tggccccagt gctgcaatga 5880
taccgcgaga cccacgctca ccggctccag atttatcagc aataaaccag ccagccggaa 5940
gggccgagcg cagaagtggt cctgcaactt tatccgcctc catccagtct attaattgtt 6000
gccgggaagc tagagtaagt agttcgccag ttaatagttt cgcaacgtt gttgccattg 6060
ctacaggcat cgtggtgtca cgctcgtcgt ttggtatggc ttcattcagc tccggttccc 6120
aacgatcaag gcgagttaca tgatccccca tgttgtgcaa aaaagcggtt agctccttcg 6180
gtcctccgat cgttgtcaga agtaagttgg ccgcagtgtt atcactcatg gttatggcag 6240
cactgcataa ttctcttact gtcatgccat ccgtaagatg cttttctgtg actggtgagt 6300
actcaaccaa gtcattctga atagtgta tgcggcgacc gagttgctct tgcccggcgt 6360
caatacggga taataccgcg ccacatagca gaactttaaa agtgctcatc attggaaaac 6420
gttcttcggg gcgaaaactc tcaaggatct taccgctgtt gagatccagt tcgatgtaac 6480
ccactcgtgc acccaactga tcttcagcat cttttacttt caccagcgtt tctgggtgag 6540
caaaaacagg aaggcaaaat gccgcaaaaa agggaataag ggcgacacgg aaatgttgaa 6600
tactcatact cttccttttt caatattatt gaagcattta tcagggttat tgtctcatga 6660
gcggatacat atttgaatgt atttagaaaa ataaacaaat aggggttccg cgcacatttc 6720
cccgaaaagt gccacctgac gtctaagaaa ccattattat catgacatta acctataaaa 6780
ataggcgtat cacgaggccc tttcgtctcg cgcgtttcgg tgatgacggt gaaaacctct 6840
gacacatgca gctcccggag acggtcacag cttgtctgta agcggatgcc gggagcagac 6900
aagcccgtca gggcgcgtca gcgggtgttg gcgggtgtcg gggctggctt aactatgcgg 6960
catcagagca gattgtactg agagtgcacc atatgcggtg tgaaataccg cacagatgcg 7020
taaggagaaa ataccgcatc aggcgccatt cgccattcag gctgcgcaac tgttgggaag 7080
ggcgatcggt gcgggcctct tcgctattac gccagctggc gaaagggga tgtgctgcaa 7140
ggcgattaag ttgggtaacg ccagggtttt cccagtcacg acgttgtaaa acgacggcca 7200
gtgaattagt actctagctt aagtaacgcc attttgcaag gcatggaaaa tacataactg 7260
agaatagaga agttcaga                                               7278

SEQ ID NO: 21           moltype = DNA  length = 7308
FEATURE                 Location/Qualifiers
misc_feature            1..7308
                        note = pMP71-TCR1705mmc
source                  1..7308
                        mol_type = other DNA
                        organism = synthetic construct
SEQUENCE: 21
tcaaggttag gaacagagag acagcagaat atgggccaaa caggatatct gtggtaagca 60
gttcctgccc cggctcaggg ccaagaacag ttggaacagc agaatatggg ccaaacagga 120
tatctgtggt aagcagttcc tgccccggct cagggccaag aacagatggt ccccagatgc 180
ggtcccgccc tcagcagttt ctagagaacc atcagatgtt tccagggtgc cccaaggacc 240
tgaaatgacc ctgtgcctta tttgaactaa ccaatcagtt cgcttctcgc ttctgttcgc 300
gcgcttctgc tccccgagct caataaaaga gcccacaacc cctcactcgg cgcgccagtc 360
ctccgataga ctgcgtcgcc cgggtacccg tattcccaat aaagcctctt gctgtttgca 420
tccgaatcgt ggactcgctg atccttggga ggtctcctc agattgattg actgcccacc 480
tcgggggtct ttcatttgga ggttccaccg agatttggag accctgccc agggaccacc 540
gacccccccg ccgggaggta agctggccag cggtcgtttc gtgtctgtct ctgtctttgt 600
gcgtgtttgt gccggcatct aatgtttgcg cctgcgtctg tactagttgg ctaactagat 660
ctgtatctgg cggtcccgcg gaagaactga cgagttcgta ttcccggccg cagccctgg 720
gagacgtccc agcggcctcg ggcgccgtt ttgtggccca ttctgtatca gttaacctac 780
ccgagtcgga cttttggag ctccgccact gtccgagggg tacgtggctt tgttggggga 840
cgagagacag agacacttcc cgccccgtc tgaattttttg ctttcggttt tacgccgaaa 900
ccgcgcgcgg cgtcttgtct gctgcagcat cgttctgtgt tgtctgtctgtc tgactgtgtt 960
tctgtatttg tctgaaaatt agctcgacaa agttaagtaa tagtccctct ctccaagctc 1020
acttacaggc ggccgccacc atgctgtctc cagatctgcc tgacagcgcc tggaacacca 1080
gactgctgtg ccacgtgatg ctgtgcctgc tgggagccgt gtctgtggct gctggctgga 1140
tccagagccc cagacacctg atcaaagaga agagagagac agccacctg aagtgctacc 1200
ccatcccccag gcacgacacc gtgtactggt atcagcaggg cccaggccag gacccccagt 1260
```

```
tcctgatcag cttctacgag aagatgcaga gcgacaaggg cagcatcccc gacagattca  1320
gcgcccagca gttcagcgac taccacagcg agctgaacat gagcagcctg gaactgggcg  1380
acagcgccct gtacttctgc gccagctcct ttagaggcgg cggagccaac gtgctgacct  1440
ttggcgctgg cagcagactg accgtgctgg aagacctgaa gaacgtgttc ccccccgagg  1500
tggccgtgtt cgagcccagc aaggccgaga tcgcccacac ccagaaagcc accctggtgt  1560
gcctggccac cggcttctac cccgaccacg tggaactgtc ttggtgggtg aacggcaaag  1620
aggtgcacag cggcgtgtgt accgaccccc agccctgaaa agagcagcct gccctgaacg  1680
actcccggta ctgcctgagc agccggctga gagtgtccgc caccttctgg cagaaccccc  1740
ggaaccactt cagatgccag gtgcagttct acggcctgag cgaaacgac gagtggaccc  1800
aggaccgggc caagcccgtg acccagattg tgtctgccga ggcctggggc agctgcaatg  1860
gtggcatcac cagcgccagc taccaccagg gcgtgctgag cgccaccatc ctgtacgaga  1920
tcctgctggg caaggccacc ctgtacgccg tgctggtgtc cgcccggatg ctgatggcca  1980
tggtgaaacg gaaggacagc agaggcggca gcggcgccac caactttagc ctgctgaaac  2040
aggccggcga cgtggaagag aaccctggcc ccatgatgaa gtccctgcgg gtgctgctcg  2100
tgatcctgtg gctgcagctg agctgggtgt ggtcccagca gaaagaggtg gaacaggacc  2160
caggccctct gagcgtgcca gagggcgcta tcgtgtccct gaattgcacc tacagcaaca  2220
gcgccttcca gtacttcatg tggtacagac agtacagccg gaagggcccc gagctgctga  2280
tgtacaccct ctccagcggc aacaaagagg acggccggtt cacagcccag gtggacaaga  2340
gcagcaagta catctccctg ttcatccggg acagccagcc cagcgactct gccacatacc  2400
tgtgcgccat gagcgacacc ggcaaccagt tctacttcgg caccggcacc tccctgaccg  2460
tgatccccaa catccagaac cccgaccccg ccgtgtacca gctgcgggac agcaagagca  2520
gcgacaagag cgtgtgcctg ttcaccgact tcgacagcca gaccaacgtg tcccagagca  2580
aggacagcga cgtgtacatc accgacaagt cgctgctgga catgcggagc atggacttca  2640
agagcaactc cgccgtggcc tggtccaaca gagcgacttc cgcctgcgcc aacgccttca  2700
acaacagcat catccccgag gacacattct cccccagctc cgacgtgccc tgcgacgtga  2760
agctggtgga aaagagcttc gagacagaca ccaacctgaa cttccagaac ctgagcgtga  2820
tcggcttccg gatcctgctg ctgaaggtgg ctggcttcaa cctgctgatg accctgcgcg  2880
tgtgagcag ctgaattcga gcatcttacc gccatttatt cccatatttg ttctgttttt  2940
cttgatttgg gtatacattt aaatgttaat aaaacaaaat ggtggggcaa tcatttacat  3000
tttatgggat atgtaattac tagttcaggt gtattgccaa aagacaaaca tgttaagaaa  3060
ctttcccgtt atttacgctc tgttcctgtt aatcaacctc tggattacaa aatttgtgaa  3120
agattgactg atattcttaa ctatgttgct ccttttacgc tgtgtggata tgctgcttta  3180
atgcctctgt atcatgctat tgcttcccgt acggctttcg ttttctcctc cttgtataaa  3240
tcctggttgc tgtctcttta tgaggagttg tggcccgttg tccgtcaacg tggcgtggtg  3300
tgctctgtgt ttgctgacgc aaccccact ggctgggga ttgccaccac ctgtcaactc  3360
cttttctggga ctttcgcttt cccctcccg atcgccacgg cagaactcat cgccgcctgc  3420
cttgcccgct gctggacagg gctaggttg ctgggcactg ataattccgt ggtgttgtcg  3480
gggaagctga cgtcctttcc atggctgctc gcctgtgttg ccaactggat cctgcgcggg  3540
acgtccttct gctacgtccc ttcggctctc aatccagcgg agcctccctt ccgaggcctt  3600
ctgccggttc tgcggcctct cccgcgtctt cgctttcggc ctccgacgag tcggatctcc  3660
ctttgggccg cctccccgcc tgtttcgcct cggcgtccgg tccgtgttgc ttggtcgtca  3720
cctgtgcaga attgcgaacc atggattcca ccgtgaactt tgtctcctgg catgcaaatc  3780
gtcaacttgg catgccaaga attaattcgg atccaagctt aggcctgctc gcttttcttg  3840
tgtcccattt ctattaaagg ttcctttgtt ccctaagtcc aactactaaa ctgggggata  3900
ttatgaaggg ccttgagcat ctggattctg cctagcgcta agcttaacac gagccataga  3960
tagaataaaa gattttattt agtctccaga aaaaggggg aatgaaagac cccacctgta  4020
ggtttggcaa gctagcttaa gtaacgccat tttgcaaggc atggaaaata cataactgag  4080
aatagagaag ttcagatcaa ggttaggaac agagagacag cagaatatgg gccaaacagg  4140
atatctgtgg taagcagttc ctgccccggc tcagggccaa gaacagttgg aacagcagaa  4200
tatgggccaa acaggatatc tgtggtaagc agttcctgcc ccggctcagg gccaagaaca  4260
gatgtcccc agatgcggtc ccgccctcag cagtttctag agaaccatca gatgtttcca  4320
gggtgcccca aggacctgaa atgaccctgt gccttatttg aactaaccaa tcagttcgct  4380
tctcgcttct gttcgcgcgc ttctgctccc gagctcaat aaaagagccc acaaccctc  4440
actcggcgcg ccagtcctcc gatagactgc gtcgcccggg tacccgtgtt ctcaataaac  4500
cctcttgcag ttgcatccga ctcgtggtct cgctgttcct tgggagggtc tcctctgagt  4560
gattgactgc ccacctcggg ggtctttcat tctcgagcag cttggcgtaa tcatggtcat  4620
agctgttttcc tgtgtgaaat tgttatccgc tcacaattcc acacaacata cgagccggaa  4680
gcataaagtg taaagcctgg ggtgcctaat gagtgagcta actcacatta ttgcgttgc  4740
gctcactgcc cgctttccag tcgggaaacc tgtcgtgcca gctgcattaa tgaatcggcc  4800
aacgcgcggg gagaggcggt ttgcgtattg ggcgctcttc cgcttcctcg ctcactgact  4860
cgctgcgctc ggtcgttcgg ctgcggcgag cggtatcagc tcactcaaag gcggtaatac  4920
ggttatccac agaatcaggg gataacgcag gaaagaacat gtgagcaaaa ggccagcaaa  4980
aggccaggaa ccgtaaaaag gccgcgttgc tggcgttttt ccataggctc cgcccccctg  5040
acgagcatca caaaaatcga cgctcaagtc agaggtggcg aaacccgaca gactataaa  5100
gataccaggc gtttccccct ggaagctccc tcgtgcgctc tcctgttccg acccctgccgc  5160
ttaccggata cctgtccgcc tttctccctt cgggaagcgt ggcgctttct catagctcac  5220
gctgtaggta tctcagttcg gtgtaggtcg ttcgctccaa gctgggctgt gtgcacgaac  5280
cccccgttca gcccgaccgc tgcgccttat ccggtaacta tcgtcttgag tccaacccgg  5340
taagacacga cttatcgcca ctggcagcag ccactggtaa caggattagc agagcgaggt  5400
atgtaggcgg tgctacagag ttcttgaagt ggtggcctaa ctacggctac actagaagaa  5460
cagtatttgg tatctgcgct ctgctgaagc cagttacctt cggaaaaaga gttggtagct  5520
cttgatccgg caaacaaacc accgctggta gcggtggttt ttttgtttgc aagcagcaga  5580
ttacgcgcag aaaaaagga tctcaagaag atcctttgat cttttctacg ggtctgacg  5640
ctcagtggaa cgaaaactca cgttaaggga ttttggtcat gagattatca aaaaggatct  5700
tcacctagat ccttttaaat taaaaatgaa gttttaaatc aatctaaagt atatatgagt  5760
aaacttggtc tgacagttac caatgcttaa tcagtgaggc acctatctca gcgatctgtc  5820
tatttcgttc atccatagtt gcctgactcc ccgtcgtgta gataactacg atacgggagg  5880
gcttaccatc tggccccagt gctgcaatga taccgcgaga cccacgctca ccggctccag  5940
atttatcagc aataaaccag ccagccggaa gggccgagcg cagaagtggt cctgcaactt  6000
```

-continued

```
tatccgcctc catccagtct attaattgtt gccgggaagc tagagtaagt agttcgccag   6060
ttaatagttt gcgcaacgtt gttgccattg ctacaggcat cgtggtgtca cgctcgtcgt   6120
ttggtatggc ttcattcagc tccggttccc aacgatcaag gcgagttaca tgatccccca   6180
tgttgtgcaa aaaagcggtt agctccttcg gtcctccgat cgttgtcaga agtaagttgg   6240
ccgcagtgtt atcactcatg gttatggcag cactgcataa ttctcttact gtcatgccat   6300
ccgtaagatg cttttctgtg actggtgagt actcaaccaa gtcattctga aatagtgta   6360
tgcggcgacc gagttgctct tgcccggcgt caatacggga taataccgcg ccacatagca   6420
gaactttaaa agtgctcatc attggaaaac gttcttcggg gcgaaaactc tcaaggatct   6480
taccgctgtt gagatccagt tcgatgtaac ccactcgtgc acccaactga tcttcagcat   6540
cttttacttt caccagcgtt tctgggtgag caaaaacagg aaggcaaaat gccgcaaaaa   6600
agggaataag ggcgacacgg aaatgttgaa tactcatact cttcctttt caatattatt    6660
gaagcattta tcagggttat tgtctcatga gcggatacat atttgaatgt atttagaaaa    6720
ataaacaaat aggggttccg cgcacatttc cccgaaaagt gccacctgac gtctaagaaa    6780
ccattattat catgacatta acctataaaa ataggcgtat cacgaggccc tttcgtctcg   6840
cgcgtttcgg tgatgacggt gaaaacctct gacacatgca gctcccggag acggtcacag    6900
cttgtctgta agcggatgcc gggagcagac aagcccgtca gggcgcgtca gcgggtgttg    6960
gcgggtgtcg ggctggctt aactatgcgg catcagagca gattgtactg agagtgcacc     7020
atatgcggtg tgaaataccg cacagatgcg taaggagaaa ataccgcatc aggcgccatt   7080
cgccattcag gctgcgcaac tgttgggaag ggcgatcggt gcgggcctct tcgctattac   7140
gccagctggc gaaaggggga tgtgctgcaa ggcgattaag ttgggtaacg ccagggtttt   7200
cccagtcacg acgttgtaaa acgacggcca gtgaattagt actctagctt aagtaacgcc   7260
attttgcaag gcatggaaaa tacataactg agaatagaga agttcaga              7308

SEQ ID NO: 22          moltype = AA  length = 275
FEATURE                Location/Qualifiers
REGION                 1..275
                       note = TCR1367hc - TCRa15
source                 1..275
                       mol_type = protein
                       organism = synthetic construct
SEQUENCE: 22
MKTFAGFSFL FLWLQLDCMS RGEDVEQSLF LSVREGDSSV INCTYTDSSS TYLYWYKQEP    60
GAGLQLLTYI FSNMDMKQDQ RLTVLLNKKD KHLSLRIADT QTGDSAIYFC AESIGSNSGY   120
ALNFGKGTSL LVTPHIQNPD PAVYQLRDSK SSDKSVCLFT DFDSQTNVSQ SKDSDVYITD   180
KTVLDMRSMD FKSNSAVAWS NKSDFACANA FNNSIIPEDT FFPSPESSCD VKLVEKSFET   240
DTNLNFQNLS VIGFRILLLK VAGFNLLMTL RLWSS                              275

SEQ ID NO: 23          moltype = AA  length = 310
FEATURE                Location/Qualifiers
REGION                 1..310
                       note = TCR1367hc - TCRb3
source                 1..310
                       mol_type = protein
                       organism = synthetic construct
SEQUENCE: 23
MGIRLLCRVA FCFLAVGLVD VKVTQSSRYL VKRTGEKVFL ECVQDMDHEN MFWYRQDPGL    60
GLRLIYFSYD VKMKEKGDIP EGYSVSREKK ERFSLILESA STNQTSMYLC ASRGLAGYEQ   120
YFGPGTRLTV TEDLKNVFPP EVAVFEPSEA EISHTQKATL VCLATGFYPD HVELSWWVNG   180
KEVHSGVSTD PQPLKEQPAL NDSRYCLSSR LRVSATFWQN PRNHFRCQVQ FYGLSENDEW   240
TQDRAKPVTQ IVSAEAWGRA DCGFTSESYQ QGVLSATILY EILLGKATLY AVLVSALVLM   300
AMVKRKDSRG                                                          310

SEQ ID NO: 24          moltype = AA  length = 275
FEATURE                Location/Qualifiers
REGION                 1..275
                       note = TCR1367mmc - TCRa15mmc
source                 1..275
                       mol_type = protein
                       organism = synthetic construct
SEQUENCE: 24
MKTFAGFSFL FLWLQLDCMS RGEDVEQSLF LSVREGDSSV INCTYTDSSS TYLYWYKQEP    60
GAGLQLLTYI FSNMDMKQDQ RLTVLLNKKD KHLSLRIADT QTGDSAIYFC AESIGSNSGY   120
ALNFGKGTSL LVTPHIQNPD PAVYQLRDSK SSDKSVCLFT DFDSQTNVSQ SKDSDVYITD   180
KCVLDMRSMD FKSNSAVAWS NKSDFACANA FNNSIIPEDT FFPSSDVPCD VKLVEKSFET   240
DTNLNFQNLS VIGFRILLLK VAGFNLLMTL RLWSS                              275

SEQ ID NO: 25          moltype = AA  length = 310
FEATURE                Location/Qualifiers
REGION                 1..310
                       note = TCR1367mmc - TCRb3mmc
source                 1..310
                       mol_type = protein
                       organism = synthetic construct
SEQUENCE: 25
MGIRLLCRVA FCFLAVGLVD VKVTQSSRYL VKRTGEKVFL ECVQDMDHEN MFWYRQDPGL    60
GLRLIYFSYD VKMKEKGDIP EGYSVSREKK ERFSLILESA STNQTSMYLC ASRGLAGYEQ   120
YFGPGTRLTV TEDLKNVFPP EVAVFEPSKA EIAHTQKATL VCLATGFYPD HVELSWWVNG   180
KEVHSGVCTD PQPLKEQPAL NDSRYCLSSR LRVSATFWQN PRNHFRCQVQ FYGLSENDEW   240
TQDRAKPVTQ IVSAEAWGRA DCGITSASYH QGVLSATILY EILLGKATLY AVLVSALVLM   300
```

```
AMVKRKDSRG                                                            310

SEQ ID NO: 26           moltype = AA  length = 273
FEATURE                 Location/Qualifiers
REGION                  1..273
                        note = TCR1405hc - TCRa8
source                  1..273
                        mol_type = protein
                        organism = synthetic construct
SEQUENCE: 26
MTSIRAVFIF LWLQLDLVNG ENVEQHPSTL SVQEGDSAVI KCTYSDSASN YFPWYKQELG   60
KGPQLIIDIR SNVGEKKDQR IAVTLNKTAK HFSLHITETQ PEDSAVYFCA ARPNSGNTPL  120
VFGKGTRLSV IANIQNPDPA VYQLRDSKSS DKSVCLFTDF DSQTNVSQSK DSDVYITDKT  180
VLDMRSMDFK SNSAVAWSNK SDFACANAFN NSIIPEDTFF PSPESSCDVK LVEKSFETDT  240
NLNFQNLSVI GFRILLLKVA GFNLLMTLRL WSS                               273

SEQ ID NO: 27           moltype = AA  length = 309
FEATURE                 Location/Qualifiers
REGION                  1..309
                        note = TCR1405hc - TCRb4
source                  1..309
                        mol_type = protein
                        organism = synthetic construct
SEQUENCE: 27
MLSLLLLLLG LGSVFSAVIS QKPSRDICQR GTSLTIQCQV DSQVTMMFWY RQQPGQSLTL   60
IATANQGSEA TYESGFVIDK FPISRPNLTF STLTVSNMSP EDSSIYLCSV EQDTNTGELF  120
FGEGSRLTVL EDLKNVFPPE VAVFEPSEAE ISHTQKATLV CLATGFYPDH VELSWWVNGK  180
EVHSGVSTDP QPLKEQPALN DSRYCLSSRL RVSATFWQNP RNHFRCQVQF YGLSENDEWT  240
QDRAKPVTQI VSAEAWGRAD CGFTSESYQQ GVLSATILYE ILLGKATLYA VLVSALVLMA  300
MVKRKDSRG                                                          309

SEQ ID NO: 28           moltype = AA  length = 273
FEATURE                 Location/Qualifiers
REGION                  1..273
                        note = TCR1405mmc - TCRa8mmc
source                  1..273
                        mol_type = protein
                        organism = synthetic construct
SEQUENCE: 28
MTSIRAVFIF LWLQLDLVNG ENVEQHPSTL SVQEGDSAVI KCTYSDSASN YFPWYKQELG   60
KGPQLIIDIR SNVGEKKDQR IAVTLNKTAK HFSLHITETQ PEDSAVYFCA ARPNSGNTPL  120
VFGKGTRLSV IANIQNPDPA VYQLRDSKSS DKSVCLFTDF DSQTNVSQSK DSDVYITDKC  180
VLDMRSMDFK SNSAVAWSNK SDFACANAFN NSIIPEDTFF PSSDVPCDVK LVEKSFETDT  240
NLNFQNLSVI GFRILLLKVA GFNLLMTLRL WSS                               273

SEQ ID NO: 29           moltype = AA  length = 309
FEATURE                 Location/Qualifiers
REGION                  1..309
                        note = TCR1405mmc - TCRb4mmc
source                  1..309
                        mol_type = protein
                        organism = synthetic construct
SEQUENCE: 29
MLSLLLLLLG LGSVFSAVIS QKPSRDICQR GTSLTIQCQV DSQVTMMFWY RQQPGQSLTL   60
IATANQGSEA TYESGFVIDK FPISRPNLTF STLTVSNMSP EDSSIYLCSV EQDTNTGELF  120
FGEGSRLTVL EDLKNVFPPE VAVFEPSKAE IAHTQKATLV CLATGFYPDH VELSWWVNGK  180
EVHSGVCTDP QPLKEQPALN DSRYCLSSRL RVSATFWQNP RNHFRCQVQF YGLSENDEWT  240
QDRAKPVTQI VSAEAWGRAD CGITSASYHQ GVLSATILYE ILLGKATLYA VLVSALVLMA  300
MVKRKDSRG                                                          309

SEQ ID NO: 30           moltype = AA  length = 273
FEATURE                 Location/Qualifiers
REGION                  1..273
                        note = TCR1705hc - TCRa2
source                  1..273
                        mol_type = protein
                        organism = synthetic construct
SEQUENCE: 30
MMKSLRVLLV ILWLQLSWVW SQQKEVEQDP GPLSVPEGAI VSLNCTYSNS AFQYFMWYRQ   60
YSRKGPELLM YTYSSGNKED GRFTAQVDKS SKYISLFIRD SQPSDSATYL CAMSDTGNQF  120
YFGTGTSLTV IPNIQNPDPA VYQLRDSKSS DKSVCLFTDF DSQTNVSQSK DSDVYITDKT  180
VLDMRSMDFK SNSAVAWSNK SDFACANAFN NSIIPEDTFF PSPESSCDVK LVEKSFETDT  240
NLNFQNLSVI GFRILLLKVA GFNLLMTLRL WSS                               273

SEQ ID NO: 31           moltype = AA  length = 322
FEATURE                 Location/Qualifiers
REGION                  1..322
                        note = TCR1705hc - TCRb13
source                  1..322
```

```
                                mol_type = protein
                                organism = synthetic construct
SEQUENCE: 31
MLSPDLPDSA WNTRLLCHVM LCLLLGAVSVA AGVIQSPRHL IKEKRETATL KCYPIPRHDT     60
VYWYQQGPGQ DPQFLISFYE KMQSDKGSIP DRFSAQQFSD YHSELNMSSL ELGDSALYFC    120
ASSFRGGGAN VLTFGAGSRL TVLEDLKNVF PPEVAVFEPS EAEISHTQKA TLVCLATGFY    180
PDHVELSWWV NGKEVHSGVS TDPQPLKEQP ALNDSRYCLS SRLRVSATFW QNPRNHFRCQ    240
VQFYGLSEND EWTQDRAKPV TQIVSAEAWG RADCGFTSES YQQGVLSATI LYEILLGKAT    300
LYAVLVSALV LMAMVKRKDS RG                                             322

SEQ ID NO: 32               moltype = AA    length = 273
FEATURE                     Location/Qualifiers
REGION                      1..273
                                note = TCR1705mmc - TCRa2mmc
source                      1..273
                                mol_type = protein
                                organism = synthetic construct
SEQUENCE: 32
MMKSLRVLLV ILWLQLSWVV SQQKEVEQDP GPLSVPEGAI VSLNCTYSNS AFQYFMWYRQ     60
YSRKGPELLM YTYSSGNKED GRFTAQVDKS SKYISLFIRD SQPSDSATYL CAMSDTGNQF    120
YFGTGTSLTV IPNIQNPDPA VYQLRDSKSS DKSVCLFTDF DSQTNVSQSK DSDVYITDKC    180
VLDMRSMDFK SNSAVAWSNK SDFACANAFN NSIIPEDTFF PSSDVPCDVK LVEKSFETDT    240
NLNFQNLSVI GFRILLLKVA GFNLLMTLRL WSS                                 273

SEQ ID NO: 33               moltype = AA    length = 322
FEATURE                     Location/Qualifiers
REGION                      1..322
                                note = TCR1705mmc - TCRb13mmc
source                      1..322
                                mol_type = protein
                                organism = synthetic construct
SEQUENCE: 33
MLSPDLPDSA WNTRLLCHVM LCLLLGAVSVA AGVIQSPRHL IKEKRETATL KCYPIPRHDT     60
VYWYQQGPGQ DPQFLISFYE KMQSDKGSIP DRFSAQQFSD YHSELNMSSL ELGDSALYFC    120
ASSFRGGGAN VLTFGAGSRL TVLEDLKNVF PPEVAVFEPS KAEIAHTQKA TLVCLATGFY    180
PDHVELSWWV NGKEVHSGVC TDPQPLKEQP ALNDSRYCLS SRLRVSATFW QNPRNHFRCQ    240
VQFYGLSEND EWTQDRAKPV TQIVSAEAWG RADCGITSAS YHQGVLSATI LYEILLGKAT    300
LYAVLVSALV LMAMVKRKDS RG                                             322

SEQ ID NO: 34               moltype = AA    length = 271
FEATURE                     Location/Qualifiers
REGION                      1..271
                                note = 1367_mc - TCRa15mc
source                      1..271
                                mol_type = protein
                                organism = synthetic construct
SEQUENCE: 34
MKTFAGFSFL FLWLQLDCMS RGEDVEQSLF LSVREGDSSV INCTYTDSSS TYLYWYKQEP     60
GAGLQLLTYI FSNMDMKQDQ RLTVLLNKKD KHLSLRIADT QTGDSAIYFC AESIGSNSGY    120
ALNFGKGTSL LVTPHIQNPE PAVYQLKDPR SQDSTLCLFT DFDSQINVPK TMESGTFITD    180
KTVLDMKAMD SKSNGAIAWS NQTSFTCQDI FKETNATYPS SDVPCDATLT EKSFETDMNL    240
NFQNLSVMGL RILLLKVAGF NLLMTLRLWS S                                   271

SEQ ID NO: 35               moltype = AA    length = 304
FEATURE                     Location/Qualifiers
REGION                      1..304
                                note = 1367_mc - TCRb3mc
source                      1..304
                                mol_type = protein
                                organism = synthetic construct
SEQUENCE: 35
MGIRLLCRVA FCFLAVGLVD VKVTQSSRYL VKRTGEKVFL ECVQDMDHEN MFWYRQDPGL     60
GLRLIYFSYD VKMKEKGDIP EGYSVSREKK ERFSLILESA STNQTSMYLC ASRGLAGYEQ    120
YFGPGTRLTV TEDLRNVTPP KVSLFEPSKA EIANKQKATL VCLARGFFPD HVELSWWVNG    180
KEVHSGVSTD PQAYKESNYS YCLSSRLRVS ATFWHNPRNH FRCQVQFHGL SEEDKWPEGS    240
PKPVTQNISA EAWGRADCGI TSASYHQGVL SATILYEILL GKATLYAVLV SGLVLMAMVK    300
KKNS                                                                 304

SEQ ID NO: 36               moltype = AA    length = 269
FEATURE                     Location/Qualifiers
REGION                      1..269
                                note = 1405_mc - TCRa8mc
source                      1..269
                                mol_type = protein
                                organism = synthetic construct
SEQUENCE: 36
MTSIRAVFIF LWLQLDLVNG ENVEQHPSTL SVQEGDSAVI KCTYSDSASN YFPWYKQELG     60
KGPQLIIDIR SNVGEKKDQR IAVTLNKTAK HFSLHITETQ PEDSAVYFCA ARPNSGNTPL    120
VFGKGTRLSV IANIQNPEPA VYQLKDPRSQ DSTLCLFTDF DSQINVPKTM ESGTFITDKT    180
```

```
VLDMKAMDSK SNGAIAWSNQ TSFTCQDIFK ETNATYPSSD VPCDATLTEK SFETDMNLNF    240
QNLSVMGLRI LLLKVAGFNL LMTLRLWSS                                     269

SEQ ID NO: 37           moltype = AA  length = 303
FEATURE                 Location/Qualifiers
REGION                  1..303
                        note = 1405_mc - TCRb4mc
source                  1..303
                        mol_type = protein
                        organism = synthetic construct
SEQUENCE: 37
MLSLLLLLLG LGSVFSAVIS QKPSRDICQR GTSLTIQCQV DSQVTMMFWY RQQPGQSLTL    60
IATANQGSEA TYESGFVIDK FPISRPNLTF STLTVSNMSP EDSSIYLCSV EQDTNTGELF    120
FGEGSRLTVL EDLRNVTPPK VSLFEPSKAE IANKQKATLV CLARGFFPDH VELSWWVNGK    180
EVHSGVSTDP QAYKESNYSY CLSSRLRVSA TFWHNPRNHF RCQVQFHGLS EEDKWPEGSP    240
KPVTQNISAE AWGRADCGIT SASYHQGVLS ATILYEILLG KATLYAVLVS GLVLMAMVKK    300
KNS                                                                 303

SEQ ID NO: 38           moltype = AA  length = 269
FEATURE                 Location/Qualifiers
REGION                  1..269
                        note = 1705_mc - TCRa2mc
source                  1..269
                        mol_type = protein
                        organism = synthetic construct
SEQUENCE: 38
MMKSLRVLLV ILWLQLSWVW SQQKEVEQDP GPLSVPEGAI VSLNCTYSNS AFQYFMWYRQ    60
YSRKGPELLM YTYSSGNKED GRFTAQVDKS SKYISLFIRD SQPSDSATYL CAMSDTGNQF    120
YFGTGTSLTV IPNIQNPEPA VYQLKDPRSQ DSTLCLFTDF DSQINVPKTM ESGTFITDKT    180
VLDMKAMDSK SNGAIAWSNQ TSFTCQDIFK ETNATYPSSD VPCDATLTEK SFETDMNLNF    240
QNLSVMGLRI LLLKVAGFNL LMTLRLWSS                                     269

SEQ ID NO: 39           moltype = AA  length = 316
FEATURE                 Location/Qualifiers
REGION                  1..316
                        note = 1705_mc - TCRb13mc
source                  1..316
                        mol_type = protein
                        organism = synthetic construct
SEQUENCE: 39
MLSPDLPDSA WNTRLLCHVM LCLLGAVSVA AGVIQSPRHL IKEKRETATL KCYPIPRHDT    60
VYWYQQGPGQ DPQFLISFYE KMQSDKGSIP DRFSAQQFSD YHSELNMSSL ELGDSALYFC    120
ASSFRGGGAN VLTFGAGSRL TVEDLRNVT PPKVSLFEPS KAEIANKQKA TLVCLARGFF    180
PDHVELSWWV NGKEVHSGVS TDPQAYKESN YSYCLSSRLR VSATFWHNPR NHFRCQVQFH    240
GLSEEDKWPE GSPKPVTQNI SAEAWGRADC GITSASYHQG VLSATILYEI LLGKATLYAV    300
LVSGLVLMAM VKKKNS                                                   316

SEQ ID NO: 40           moltype = AA  length = 6
FEATURE                 Location/Qualifiers
source                  1..6
                        mol_type = protein
                        organism = Homo sapiens
SEQUENCE: 40
DSSSTY                                                              6

SEQ ID NO: 41           moltype = AA  length = 7
FEATURE                 Location/Qualifiers
source                  1..7
                        mol_type = protein
                        organism = Homo sapiens
SEQUENCE: 41
IFSNMDM                                                             7

SEQ ID NO: 42           moltype = AA  length = 6
FEATURE                 Location/Qualifiers
source                  1..6
                        mol_type = protein
                        organism = Homo sapiens
SEQUENCE: 42
DSASNY                                                              6

SEQ ID NO: 43           moltype = AA  length = 7
FEATURE                 Location/Qualifiers
source                  1..7
                        mol_type = protein
                        organism = Homo sapiens
SEQUENCE: 43
IRSNVGE                                                             7
```

```
SEQ ID NO: 44           moltype = AA   length = 6
FEATURE                 Location/Qualifiers
source                  1..6
                        mol_type = protein
                        organism = Homo sapiens
SEQUENCE: 44
NSAFQY                                                                    6

SEQ ID NO: 45           moltype = AA   length = 6
FEATURE                 Location/Qualifiers
source                  1..6
                        mol_type = protein
                        organism = Homo sapiens
SEQUENCE: 45
TYSSGN                                                                    6

SEQ ID NO: 46           moltype = AA   length = 5
FEATURE                 Location/Qualifiers
source                  1..5
                        mol_type = protein
                        organism = Homo sapiens
SEQUENCE: 46
MDHEN                                                                     5

SEQ ID NO: 47           moltype = AA   length = 6
FEATURE                 Location/Qualifiers
source                  1..6
                        mol_type = protein
                        organism = Homo sapiens
SEQUENCE: 47
SYDVKM                                                                    6

SEQ ID NO: 48           moltype = AA   length = 5
FEATURE                 Location/Qualifiers
source                  1..5
                        mol_type = protein
                        organism = Homo sapiens
SEQUENCE: 48
SQVTM                                                                     5

SEQ ID NO: 49           moltype = AA   length = 7
FEATURE                 Location/Qualifiers
source                  1..7
                        mol_type = protein
                        organism = Homo sapiens
SEQUENCE: 49
ANQGSEA                                                                   7

SEQ ID NO: 50           moltype = AA   length = 5
FEATURE                 Location/Qualifiers
source                  1..5
                        mol_type = protein
                        organism = Homo sapiens
SEQUENCE: 50
PRHDT                                                                     5

SEQ ID NO: 51           moltype = AA   length = 6
FEATURE                 Location/Qualifiers
source                  1..6
                        mol_type = protein
                        organism = Homo sapiens
SEQUENCE: 51
FYEKMQ                                                                    6

SEQ ID NO: 52           moltype = AA   length = 31
FEATURE                 Location/Qualifiers
source                  1..31
                        mol_type = protein
                        organism = Homo sapiens
SEQUENCE: 52
ALAETSYVKV LEYVIKVSAR VRFFFPSLRE A                                       31

SEQ ID NO: 53           moltype = AA   length = 31
FEATURE                 Location/Qualifiers
source                  1..31
                        mol_type = protein
                        organism = Mus musculus
SEQUENCE: 53
AFAETSKMKV LQFFASINKT HPRAYPEKYA E                                       31
```

```
SEQ ID NO: 54            moltype = AA  length = 9
FEATURE                  Location/Qualifiers
source                   1..9
                         mol_type = protein
                         organism = Homo sapiens
SEQUENCE: 54
KVLEFVAKV                                                                    9

SEQ ID NO: 55            moltype = AA  length = 9
FEATURE                  Location/Qualifiers
source                   1..9
                         mol_type = protein
                         organism = Homo sapiens
SEQUENCE: 55
KVLEYLAKV                                                                    9
```

The invention claimed is:

1. A method of manufacturing a T cell receptor (TCR), or a derivative or fragment thereof that binds to MAGE-A1 antigen, wherein the TCR, or the derivative or fragment thereof that binds to MAGE-A1 antigen is selected from the group consisting of:
   a TCR or derivative or fragment thereof that comprises (i) an alpha chain comprising complementarity-determining regions (CDRs) having the amino acid sequences of SEQ ID NO: 40, 41, and 1; and (ii) a beta chain comprising CDRs having the amino acid sequences of SEQ ID NO: 46, 47, and 4,
   a TCR or derivative or fragment thereof that comprises (i) an alpha chain comprising CDRs having the amino acid sequences of SEQ ID NO: 42, 43, and 2; and (ii) a beta chain comprising CDRs having the amino acid sequences of SEQ ID NO: 48, 49, and 5, and a TCR or derivative or fragment thereof that comprises (i) an alpha chain comprising CDRs having the amino acid sequences of SEQ ID NO: 44, 45, and 3; and (ii) a beta chain comprising CDRs having the amino acid sequences of SEQ ID NO: 50, 51, and 6.
wherein the method comprises:
   a) providing a suitable host cell;
   b) providing a genetic construct encoding the TCR or the derivative or fragment thereof that binds to MAGE-A1 antigen;
   c) introducing into said suitable host cell said genetic construct; and
   d) expressing said genetic construct by said suitable host cell.

2. The method of claim 1, further comprising purifying the TCR from the host cell and reconstituting the translated TCRs in a T-cell.

\* \* \* \* \*